(12) United States Patent
Zhou et al.

(10) Patent No.: US 8,722,896 B2
(45) Date of Patent: May 13, 2014

(54) PROKINETICIN RECEPTOR ANTAGONISTS AND USES THEREOF

(75) Inventors: Qun-Yong Zhou, Irvine, CA (US); Jia-Da Li, Irvine, CA (US); Qi Huang, Moor Park, CA (US)

(73) Assignee: The Regents of the University of California, Oakland, CA (US)

( * ) Notice: Subject to any disclaimer, the term of this patent is extended or adjusted under 35 U.S.C. 154(b) by 127 days.

(21) Appl. No.: 13/140,314

(22) PCT Filed: Dec. 16, 2009

(86) PCT No.: PCT/US2009/068304
§ 371 (c)(1),
(2), (4) Date: Aug. 30, 2011

(87) PCT Pub. No.: WO2010/077976
PCT Pub. Date: Jul. 8, 2010

(65) Prior Publication Data
US 2012/0035149 A1   Feb. 9, 2012

Related U.S. Application Data

(60) Provisional application No. 61/138,433, filed on Dec. 17, 2008, provisional application No. 61/219,226, filed on Jun. 22, 2009.

(51) Int. Cl.
*C07C 233/02* (2006.01)
*C07D 213/36* (2006.01)

(52) U.S. Cl.
USPC .......................... 546/329; 564/164

(58) Field of Classification Search
USPC .......................... 546/329; 564/164
See application file for complete search history.

(56) References Cited

U.S. PATENT DOCUMENTS

| 4,320,061 | A | 3/1982 | Ohlendorf et al. |
|---|---|---|---|
| 4,749,786 | A | 6/1988 | Cesa et al. |
| 5,120,758 | A | 6/1992 | Satoh |
| 5,554,606 | A | 9/1996 | Betts et al. |
| 7,041,690 | B2 | 5/2006 | Finzel et al. |
| 7,109,186 | B2 | 9/2006 | Walker et al. |
| 2006/0235018 | A1 | 10/2006 | Coats et al. |
| 2008/0045535 | A1 | 2/2008 | Coats et al. |
| 2008/0085858 | A1 | 4/2008 | Harada et al. |
| 2009/0143377 | A1 | 6/2009 | Ng et al. |

FOREIGN PATENT DOCUMENTS

| WO | 2007/067511 | 6/2007 |
|---|---|---|
| WO | 2009/000163 | 12/2008 |

OTHER PUBLICATIONS

Sekiya, et al. Document No. 113:190945, retrieved from CAPLUS. Nov. 23, 1990.*

* cited by examiner

*Primary Examiner* — Shawquia Young
(74) *Attorney, Agent, or Firm* — Fish & Tsang, LLP

(57) ABSTRACT

Contemplated compounds, compositions, and methods of prokineticin antagonists are presented where a prokineticin antagonist is used in the treatment and prevention of various conditions and disorders, and especially type II diabetes.

12 Claims, 7 Drawing Sheets

PROKINETICIN RECEPTOR ANTAGONISTS AND USES THEREOF

This application claims priority to our copending U.S. provisional applications with the Ser. Nos. 61/138,433 and 61/219,226, which were filed Dec. 17, 2008 and Jun. 22, 2009, respectively, and which are incorporated by reference herein.

This invention was made with government support under grant MH067753 awarded by the National Institute of Health. The government may have certain rights in the invention.

FIELD OF THE INVENTION

The field of the invention is directed to compounds and compositions that include a prokineticin antagonist and methods therefor.

BACKGROUND OF THE INVENTION

Prokineticins are regulatory peptides that are thought to exert signaling activity via two highly conserved G protein-coupled receptors (GPCR), the prokineticin receptor 1 (PKR1) and the prokineticin receptor 2 (PKR2). Mature human prokineticins (PK1 and PK2) contain 86 and 81 amino acids, respectively, and are among the largest known ligands for all GPCRs. PK1 and PK2 share about 45% amino acid identity within and among several distinct species, and a sequence alignment readily suggests that numerous PKs exhibit complete conservation of the first six amino acids and the 10 cysteine residues predicted to form five pairs of disulfide bonds. Substitution or addition of any of the six amino acid residues in the N-terminus rendered the human PK1 inactive, and studies with chimeric proteins have shown the critical role of the cysteine-rich domain for bioactivity, although certain residue changes in the C-terminus were tolerable to at least some degree. Intriguingly, two of the N-terminus mutants with either substitution or addition of only a single amino acid resulted in mutant PKs that possessed antagonist activity, further indicating the importance of the N-terminal six residues in binding to and activating PKRs.

Over the last few years, a spectrum of biological functions ranging from development to adult physiology has been assigned to prokineticins. For example, prokineticins were reported as regulators of smooth muscle contractility in a study that used recombinant PK1 and PK2 to stimulate the contraction of guinea pig ileum. The role of PKs in gastric and colonic contractility has also been investigated, and histological studies revealed that PKR1 is also expressed on myenteric plexus neurons and colocalizes with a small subset of NOS synthetase-expressing neurons. Thus, PK may regulate gastrointestinal motility directly via activating smooth muscle cells, and indirectly via modulating the activities of enteric neurons. In another example, various studies have indicated the involvement of the PKs/PKRs in nociception. Among other data, intraplantar injection of recombinant PK2 caused a strong and localized hyperalgesia by reducing the nociceptive thresholds to thermal and mechanical stimuli, and systemic injection of frog PK2 homolog into rats induced hyperalgesia to tactile and thermal stimuli. Mice lacking the PKR1 gene were recently reported to exhibit impaired pain perception to various stimuli, including noxious heat, mechanical, capsaicin, and protons.

In yet another example, PK2 was reported to have a regulatory function in sleep regulation, circadian rhythm and stress response. It was observed that PK2 mRNA in the suprachiasmatic nucleus (SCN) displays dramatic circadian rhythmicity under light/dark and constant dark conditions and so suggests the potential regulatory function of PK2 for the circadian clock. Subsequently, multiple lines of evidence have supported the role of PK2 as a prominent output molecule for the SCN circadian clock. Furthermore, the receptor for PK2 is expressed in virtually all known primary SCN targets, indicating that these SCN targets can respond to oscillatory PK2 signal from the SCN. WO2007/067511 describes various compounds that are useful in the treatment or prevention of neurological and psychiatric disorders in which prokineticin receptors are involved, and especially for modulation of circadian rhythm and treatment of sleep disorders.

More recently, the role of PK2 in the regulation of anxiety and depression-related behaviors has also been investigated. For example, intracerebroventricular (ICV) infusion of PK2 increased anxiety behavior as assessed by elevated plus maze and light/dark box. ICV delivery of PK2 also led to increased depression-like behaviors in the tests of forced swimming and learned helplessness. Conversely, mice lacking the PK2 gene (PK2$^{-/-}$ mice) displayed significantly reduced anxiety and depression-like behaviors. Furthermore, PK2$^{-/-}$ mice show impaired responses to exposure to new environments in terms of locomotor activity, arousal, body temperature and food intake. These studies strongly suggest that PK2 signaling also plays a critical role in stress response and anxiety, and depression-related behaviors.

In still further known functions, prokineticins have been reported as potent modulators for angiogenesis, hematopoiesis, and neurogenesis. For example, PK1 was identified as a molecule that was capable of inducing proliferation of primary bovine adrenal-cortex-derived capillary endothelial (ACE) cells, and delivery of PK1 in ovary elicited potent angiogenesis and cyst formation, while the angiogenic effect is absent when delivered to cornea or skeletal muscles. PK1 and PK2 also drastically promoted the differentiation of mouse and human bone marrow cells into the monocyte/macrophage lineage, and PK2 promoted the survival and differentiation of granulocytic lineages in cultures of the human or mouse hematopoietic stem cells. Detailed expression analyses indicate that both PKR1 and PKR2 are expressed in the hematopoietic stem cells. Still further, PK2 has also been reported as regulator of neurogenesis for adult mammalian brain, and PK2 appears to function as a chemoattractant for SVZ-derived neuronal progenitors.

Consequently, prokineticin-mediated signaling has been the focus for certain methods and compositions for modulation of angiogenesis (e.g., U.S. Pat. App. No. 2004/0235732), and compositions and methods to modulate angiogenesis. For example, U.S. Pat. No. 7,323,334 teaches use of prokineticin receptor antagonists in the modulation of receptor signaling.

Therefore, while numerous compositions and methods related to prokineticin-mediated signaling have been described, there is still a need to explore and provide further compositions and methods for heretofore unknown uses.

SUMMARY OF THE INVENTION

The present invention is directed to various compounds, compositions, and methods of prokineticin antagonists, and particularly small molecule non-protein prokineticin antagonists. More particularly, the compounds and compositions described herein are particularly useful in the treatment and prevention of type II diabetes and diabetic conditions and symptoms of type II diabetes.

In one aspect of the inventive subject matter, contemplated compounds have a structure according to Formula 1

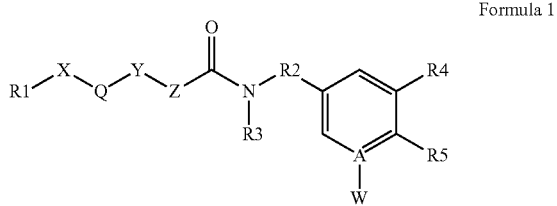

Formula 1 wherein R1 is an optionally substituted aryl, optionally substituted heteroaryl, or an optionally substituted aryl with a fused heterocyclic ring; X and Y are independently lower alkyl; Q is NH or NR6, wherein R6 is lower alkyl; Z is CH2 or CHR7, wherein R7 is lower alkyl; or Q and Z are covalently coupled to each other to form a heterocyclic 4- to 6-membered ring in which Q is N and Z is CH; R2 is lower alkylene; R3 is H, lower alkyl, or alkaryl; A is N or C; W is H, or halogen, or W is null where A is N; and R4 and R5 are independently alkoxy, or are covalently coupled to each other to form an optionally substituted heterocyclic 6- or 7-membered ring with at least one oxygen atom. Most preferably, the heterocyclic ring is not a morpholine ring.

In especially preferred aspects of the inventive subject matter, R1 is optionally substituted phenyl, optionally substituted indolyl, or optionally substituted indolinyl, and/or X and Y are CH2. It is also preferred that X and Y are covalently coupled to each other to form a pyrrolidine ring, a piperidine ring, a piperazine ring, a thiomorpholine ring, or a morpholine ring. While not limiting to the inventive subject matter, it is further generally preferred that R3 is an optionally branched lower alky, and/or that R4, R5, W, and the phenyl ring to which R4, R5, and W are covalently coupled form an optionally halogenated benzodioxepin ring. Most typically, R2 is CH2, and/or W is Cl or F.

In another aspect of the inventive subject matter, a pharmaceutical composition for treatment of a condition associated with a dysfunction or dysregulation of a prokineticin receptor is contemplated that comprising a compound according to Formula I, and a pharmaceutically acceptable carrier. Most preferably, the compound is present in a dosage unit for oral administration in an amount effective to treat or prevent a condition associated with a dysfunction or dysregulation of a prokineticin receptor, and it is particularly preferred that the condition is diabetes mellitus.

Therefore, the inventors also contemplate use of a compound according to Formula I in the manufacture of a medicament for diagnosis or treatment of a condition associated with a dysfunction of a prokineticin receptor. Most typically, the condition is diabetes mellitus, a sleep disorder, ischemic stroke, gastrointestinal mobility disorder, pain disorder, an anxiety disorder, or a mood disorder.

In a still further especially preferred aspect, the inventors also contemplate a method of treating, or preventing type II diabetes that includes a step of administering a prokineticin antagonist at a concentration effective to treat or prevent type II diabetes. Most preferably, the prokineticin antagonist is a compound according to Formula I Various objects, features, aspects and advantages of the inventive subject matter will become more apparent from the following detailed description of preferred embodiments, along with the accompanying drawing figures in which like numerals represent like components.

DETAILED DESCRIPTION OF THE INVENTION

Figure 1:
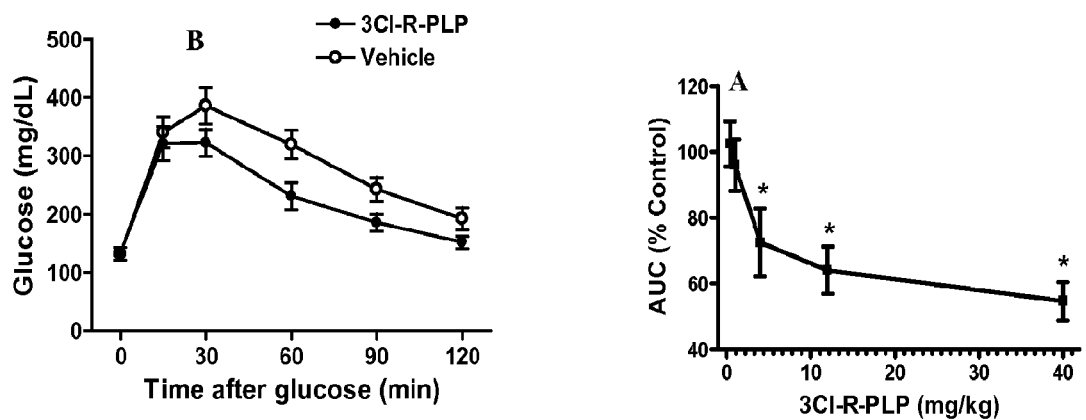
FIG. 1 is a graph depicting (Panel A) the in vivo effect of an exemplary contemplated compound on glucose clearance in a glucose tolerance test and (Panel B) a dose dependent effect of the compound.

The inventors have surprisingly discovered that prokineticin receptors and/or ligands (and particularly antagonists) for the prokineticin receptors can be used to treat, prevent, and/or manage type II diabetes, pre-diabetes, diabetic conditions, and/or symptoms of diabetes. Most preferably, contemplated methods and compositions are drawn to pharmacological intervention that targets prokineticin ligand/receptor interactions (e.g., via a small molecule inhibitor and/or antagonist, antibodies against prokineticin receptors, soluble proteins/receptors of prokineticin ligand binding, and/or antibodies against prokineticin ligands, etc.), either in a single agent therapy or as a component in a combination therapy with other (preferably commercially available) treatment agents against type II diabetes.

In further contemplated aspects of the inventive subject matter, it should be appreciated that contemplated compounds and compositions may indeed be used for all conditions and/or disorders that are associated with a dysregulation and/or dysfunction of the prokineticin receptor (unless specified otherwise, the term prokineticin receptor refers to PKR1 and PKR2). For example, suitable conditions and disorders include type II diabetes, sleep disorders, pain disorders, gastrointestinal mobility disorder, an anxiety disorder, or a mood disorder, and/or ischemic stroke. Therefore, and viewed from a different perspective, it should also be noted that contemplated compounds and compositions may also be used for diagnosis of conditions and/or disorders that are associated with a dysregulation and/or dysfunction of the prokineticin receptor, and it is especially contemplated that in such use the compounds will have a label that is radiologically detectable (e.g., alpha- or beta-particle emitter, NMR-detectable label, or PET or SPECT-detectable label).

Viewed from yet another perspective, the present inventive subject matter is directed to various compounds that modulate (e.g., inhibit or reduce) the prokineticin receptor-ligand interaction, and/or that directly or indirectly affect the receptor or ligand and so interfere with signal transduction. Exemplary compounds will therefore include amino acid derivatives, and especially the compounds discussed herein, which act as antagonists of prokineticin receptors. Consequently, the inventors also contemplate pharmaceutical compositions comprising these compounds, and the use of these compounds and compositions in the prevention or treatment of such diseases in which prokineticin receptors are involved.

Contemplated Compounds

In one aspect of the inventive subject matter, prokineticin inhibitors are contemplated that can generally be characterized as amino acid derivatives, where the amino acid may be an alpha-, beta-, delta-, gamma- (or even higher) amino acid and in which the amino acid may be linear or cyclic. Most typically, the amino acid will have a 'left-hand' modification and a 'right-hand' modification, and exemplary compounds are described as follows:

In one aspect of the inventive subject matter, contemplated compounds have a structure according to Formula A

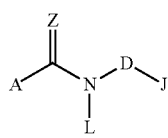

Formula A where A is an amino alkylene group, with or without substituents on the amino group. In certain preferred aspects, A is

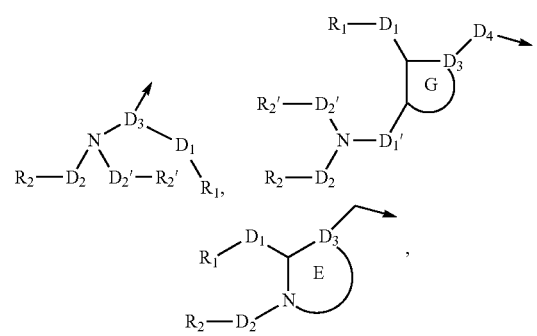

where R1, R2, and R2' are independently hydrogen, aryl, substituted aryl, heteroaryl, substituted heteroaryl, naphthyl, substituted naphthyl, fused bicyclic heteroaryl, or substituted fused bicyclic heteroaryl, and where D1, D1', D2, D2', D3, and D4 are independently a covalent bond or a $C_{1-8}$ alkylene, optionally substituted with one or more substituents.

The term "substituted" as used herein refers to a replacement of an atom or chemical group (e.g., H, NH2, or OH) with a functional group, and particularly contemplated functional groups include nucleophilic groups (e.g., —NH2, —OH, SH, —NC, etc.), electrophilic groups (e.g., C(O)OR, C(X) OH, etc.), polar groups (e.g., —OH), non-polar groups (e.g., aryl, alkyl, alkenyl, alkynyl, etc.), ionic groups (e.g., NH3+), and halogens (e.g., —F, —Cl), and all chemically reasonable combinations thereof. Thus, the term "functional group" as used herein refers to a nucleophilic group (e.g., —NH2, —OH, SH, —NC, —CN etc.), an electrophilic group (e.g., C(O)OR, C(X)OH, C(Halogen)OR, etc.), a polar group (e.g., —OH), a non-polar group (e.g., aryl, alkyl, alkenyl, alkynyl, etc.), an ionic group (e.g., NH3+), and a halogen.

E is preferably a nitrogen containing non-aromatic optionally substituted heterocyclic ring, with the basic nitrogen placed at β, γ, or δ position to the carbonyl group, and with the cyclic ring sized 3-7 members (unsubstituted or substituted). For example, suitable heterocyclic rings include pyrrolidine, piperidine, morpholine, thiomorpholine, piperazine, hydropyrimidine, hydropyridazine, hydrooxazine, oxazolidine, thiozolidine, imadazolidine, pyrozolidine, azetidine, azepine, diazepine, and rings having the following structures:

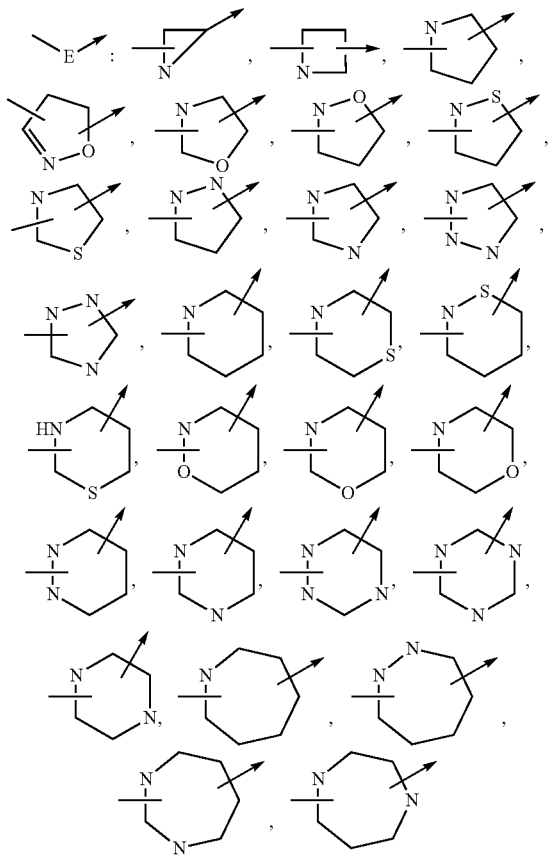

G is preferably a non-aromatic carbocyclic or non-aromatic heterocyclic ring, and most preferably a three to seven membered ring. D is a covent bond or an optionally substituted $C_{1-8}$ alkylene, and Z is preferably O, S, NRz (with Rz being hydrogen, or lower alkyl (C1-C6)).

L is preferably hydrogen, C1-12 alkyl, which is linear or branched, unsubstituted or substituted with one or more substituents selected from alkoxyl (C1-6), halogen, alkylsulfide (C1-6), alkylsulfoxide (C1-6), alkenyl, alkynyl, cyano, nitro, cyclic alkyl, cyclic alkenyl, cyclic alkynyl, phenyl, substituted phenyl, heteroaromatics (substituents may also be J as defined below). L may further be C3-7 cycloalkyl, which is unsubstituted or substituted with one or more substituents selected from alkoxyl (C1-6), halogen, alkylsulfide (C1-6), alkylsulfoxide (C1-6), alkenyl, alkynyl, cyano, nitro, cyclic alkyl, cyclic alkenyl, cyclic alkynyl, phenyl, substituted phenyl, heteroaromatics, substituted or unsubstituted (substituents may also be J as defined below). J is preferably hydrogen, or any of the following structures:

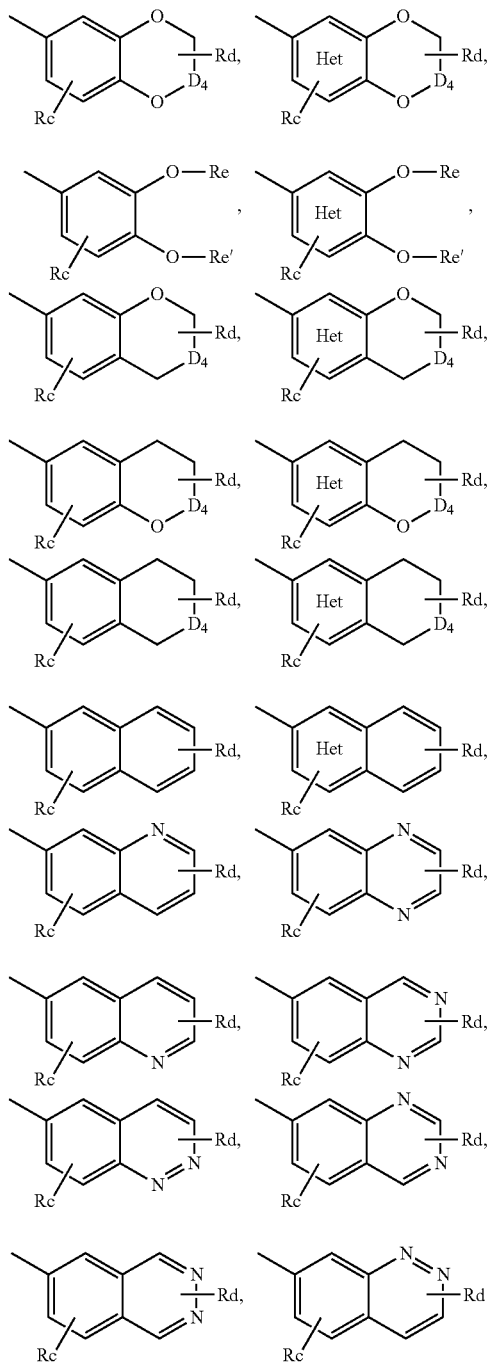

where Rc and Rd are independently hydrogen, halogen, alkyl (C1-6), cyano, hydroxy, alkoxy (C1-6), hydrosulfide, alkylsulfide(C1-6), nitro, amino, alkylamino (C1-6), substituted alkyl; where Het is a 5 or 6 membered heteroaryl (e.g., thiophene, thiazole, oxazole, pyridine, pyridazine, pyrimidine, pyrazine, 1,2,3-triazine, etc.), and where D4 is a covalent bond or $C_{1-8}$ alkylene.

Still further contemplated compounds will have a structure according to Formula B:

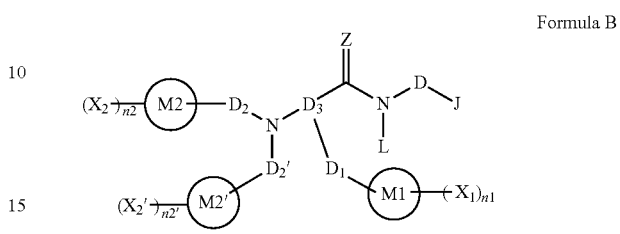

Formula B where M1, M2, and M2' are independently a covalent bond, a phenyl, a heteroaryl (e.g., pyridine, thiophene, furane, pyrimidine, pyrazine, or pyridazine), a naphthyl, a bicyclic heteroaryl (e.g., indole, benzofurane, benzophiophene, benzimidazole, quinoline, isoquinoline, quinazoline, indoline, dihydrobenzofurane, or benzimidazoline). X1, X2, and X2' are independently hydrogen, halogen, hydroxyl, amino, alkylamino ($C_{1-6}$, linear, branched, or cyclic ($C_{3-6}$)), nitro, cyano, azide, optionally substituted $C_{1-8}$ alkyl (e.g., substituted with hydroxyl, nitro, hydrosulfide, amino, etc.), alkylamino ($C_{1-6}$), alkoxyl ($C_{1-6}$), halogen, cyano, alkylsulfide ($C_{1-6}$), carboxyl, optionally substituted $C_{2-6}$ alkenyl (e.g., substituted with $C_{1-6}$ alkyl, $C_{3-6}$ cycloalkyl, phenyl, cyano), alkoxyl ($C_{1-8}$), optionally substituted tetrazolyl, thienyl, thiazolyl, benzothienyl, pyrazolyl, or imidazolyl. D1, D2, D2', and D3 are independently a covalent bond, an optionally substituted $C_{1-8}$ alkylene, an alkenyl ($C_2$-$C_6$), an alkynyl ($C_2$-$C_6$), an alkoxyl ($C_1$-$C_6$), an alkylsulfidyl ($C_{1-6}$), an alkylsulfoxidyl ($C_{1-6}$), or an azidyl, and where the remaining substituents are as defined above.

Still further contemplated compounds will have a structure according to Formula C:

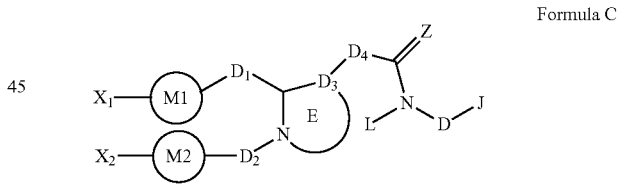

Formula C where D4 is selected from a covalent bond, an optionally substituted $C_{1-8}$ alkylene, and where E is preferably a nitrogen containing 3-7 membered non-aromatic heterocyclic ring, with the basic nitrogen placed at β, γ, or δ position to the carbonyl group (e.g., pyrrolidine, piperidine, morpholine, thiomorpholine, piperazine, hydropyrimidine, hydropyridazine, hydroxazine, oxazolidine, thiozolidine, isoxazolidine, isothiozolidine, oxazoline, isoxazoline, isothioxazolin, imadazolidine, pyrozolidine, azeridine, azetidine, azepine, diazepine, etc.). E therefore also includes the structures below:

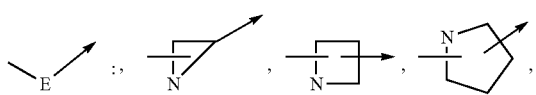

-continued

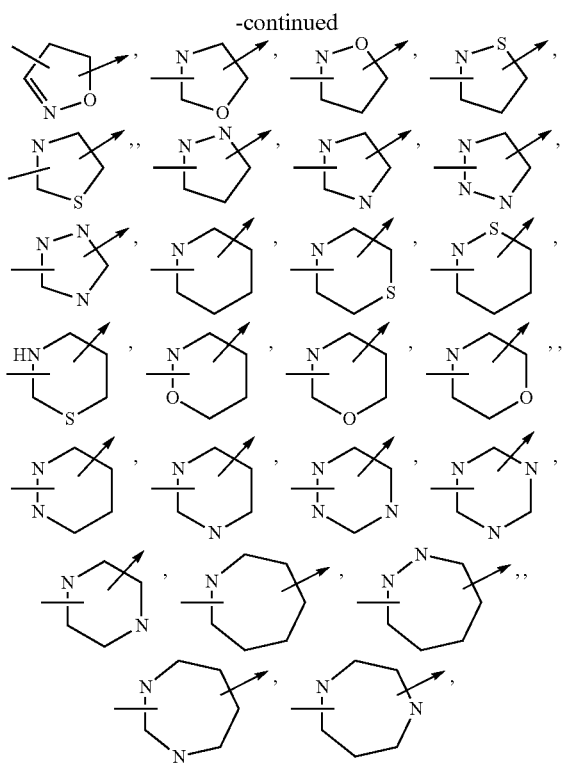

and where the remaining substituents are as defined above.

Yet further contemplated compounds include those according to Formula D:

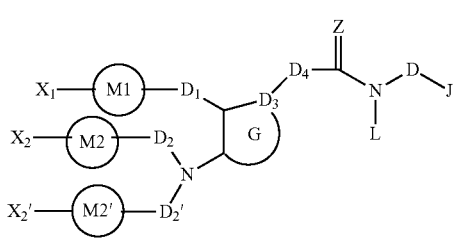

Formula D where G is a three to seven membered non-aromatic carbocyclic or non-aromatic heterocyclic ring, and preferably has a structure as shown below:

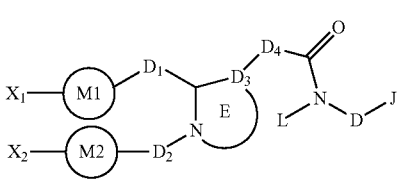

in which D7 is a covalent bond or an optionally substituted lower alkylene (C1-C6), and where HET is a 3-7 membered non-aromatic cyclic moiety which may contain one or more heteroatoms (e.g., oxygen; nitrogen; and sulfur).

Additionally contemplated compounds include those according to the Formula E

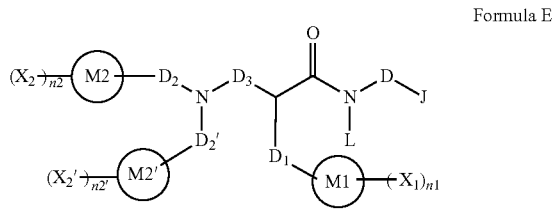

Formula E where M1 and M2 are independently a covalent bond, M2' is phenyl, X1 and X2 are hydrogen, and both n1 and n2 are 1 and where the remaining substituents are as defined above. Further contemplated compounds include those in which M1 and M2 are direct links, M2' is pyridyl, X1 and X2 are hydrogen, and both n1 and n2 are 1, and where the remaining substituents are as defined above; and those wherein D2, D2' and D3 are direct links, M2 and M2' are direct links, M1 is phenyl, X2 and X2' are hydrogen, and n1 and n2=1, and where the remaining substituents are as defined above; and those wherein D2, D2' and D3 are direct links, M2 and M2' are direct links, M1 is pyridyl, X2 and X2' are hydrogen, and n1 and n2=1, and where the remaining substituents are as defined above; and those wherein D2, D2' and D3 are direct links, M2 and M2' are direct links, M1 is indolyl, X2 and X2' are hydrogen, and n1 and n2=1, and where the remaining substituents are as defined above; and those wherein D2, D2' and D3 are direct links, M2 and M2' are direct links, M1 is benzimidazolyl, X2 and X2' are hydrogen; and n1 and n2=1, and where the remaining substituents are as defined above; and those wherein D2, D2' and D3 are direct links, M2 and M2' are direct links, M1 is benzofuranyl, X2 and X2' are hydrogen; and n1 and n2=1, and where the remaining substituents are as defined above; and those wherein D2, D2' and D3 are direct links, M1, M2 and M2' are direct links, X1, X2 and X2' are hydrogens, and where n1, n2, and n2' are 1, and where the remaining substituents are as defined above;

Further contemplated compounds include those according to Formula C':

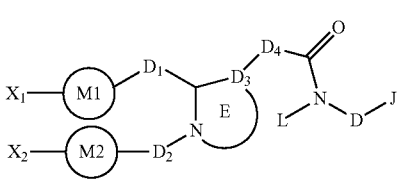

Formula C' wherein D1, M1 are direct link, X1 is hydrogen, M2 is phenyl, and where the remaining substituents are as defined above; and those wherein D1, M1 are direct link, X1 is hydrogen, M2 is pyridyl, and where the remaining substituents are as defined above; and those wherein D1, M1 are direct link, X1 is hydrogen, M2 is indolyl, and where the remaining substituents are as defined above; and those wherein D1, M1 are direct link, X1 is hydrogen, M2 is benzimidazolyl, and where the remaining substituents are as defined above; and those wherein D1, M1 are direct link, X1 is hydrogen, M2 is benzofuranyl and where the remaining substituents are as defined above; and those wherein M2 is direct link, X2 is hydrogen, M1 is phenyl, and where the remaining substituents are as defined above; and those wherein M2 is direct link, X2 is hydrogen, M1 is pyridyl, and where the remaining substituents are as defined above; and those wherein M2 is direct link, X2 is hydrogen, M1 is indolyl, and where the remaining substituents are as defined above; and those wherein M2 is direct link, X2 is hydrogen, M1 is benzimidazolyl, and where the remaining substituents are as defined above; and those wherein M2 is direct link, X2 is hydrogen, M1 is benzofuranyl, and where the remaining substituents are as defined above.

Yet further contemplated compounds include those of Formula D':

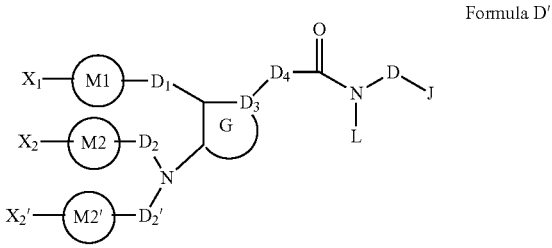

Formula D' wherein D1, D2, M1, M2 are all direct links, X1, and X2 are hydrogen, M2' is phenyl, and where the remaining substituents are as defined above; and those wherein D1, D2, M1, M2 are all direct links, X1 and X2 are hydrogen, M2' is pyridyl, and where the remaining substituents are as defined above; and those wherein D1, D2, M1, M2 are all direct links, X1 and X2 are hydrogen, M2' is indole, and where the remaining substituents are as defined above; and those wherein D1, D2, M1, M2 are all direct links, X1 and X2 are hydrogen, M2' is benzimidazolyl, and where the remaining substituents are as defined above; and those wherein D1, D2, M1, M2 are all direct links, X1 and X2 are hydrogen, M2' is benzofuranyl, and where the remaining substituents are as defined above; and those wherein D2, D2', M2, M2' are all direct links, X2, X2' are hydrogen, M1 is phenyl, and where the remaining substituents are as defined above; and those wherein D2, D2', M2, M2' are all direct links, X2, X2' are hydrogen, M1 is pyridyl, and where the remaining substituents are as defined above; and those wherein D2, D2', M2, M2' are all direct links, X2, X2' are hydrogen, M1 is benzimidazolyl, and where the remaining substituents are as defined above; and those wherein D2, D2', M2, M2' are all direct links, X2, X2' are hydrogen, M1 is benzofuranyl, and where the remaining substituents are as defined above.

In especially contemplated aspects of the inventive subject matter, contemplated compounds will have a structure according to Formula 1

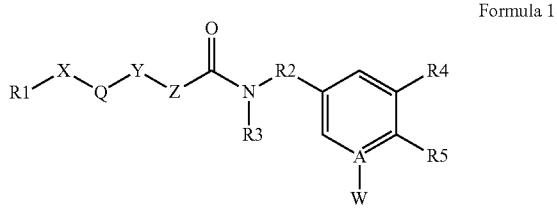

Formula 1 where R1 is an optionally substituted aryl, optionally substituted heteroaryl, or an optionally substituted aryl with a fused heterocyclic ring; X and Y are independently lower alkyl; Q is NH or NR6, wherein R6 is lower alkyl; Z is CH2 or CHR7, wherein R7 is lower alkyl; or Q and Z are covalently coupled to each other to form a heterocyclic 4- to 6-membered ring in which Q is N and Z is CH; R2 is lower alkylene; R3 is H, lower alkyl, or alkaryl; A is N or C; W is H, or halogen, or W is null where A is N; and R4 and R5 are independently alkoxy, or are covalently coupled to each other to form an optionally substituted heterocyclic 6- or 7-membered ring with at least one oxygen atom.

In especially preferred aspects, R1 is optionally substituted phenyl, optionally substituted indolyl, or optionally substituted indolinyl. It is also particularly preferred that X and Y are CH2, or that X and Y are covalently coupled to each other to form a pyrrolidine ring, a piperidine ring, a piperazine ring, a thiomorpholine ring, or a morpholine ring. Additionally, or alternatively R3 is an optionally branched lower alkyl, and/or R4, R5, W, and the phenyl ring to which R4, R5, and W are covalently coupled form an optionally halogenated benzodioxepin ring. Most typically, but not necessarily, R2 is CH2, and/or W is Cl or F. Still further particularly preferred compounds are presented in the table preceding the claims.

Certain compounds contemplated herein may comprise one or more asymmetric centers, and therefore exist in different enantiomeric forms. It should be recognized that all enantiomeric forms of contemplated compounds are specifically contemplated herein. Similarly, where contemplated compounds exhibit optical activity and/or have stereoisomers, all isomeric forms are contemplated herein. Furthermore, where double bonds distinguish a Z-form from an E-form (or cis- from trans-), both isomers are contemplated.

Still further, it should be recognized that the compounds according to the inventive subject matter may also be isotopically-labeled. Examples of suitable isotopes $^{2}H$, $^{3}H$, $^{13}C$, $^{14}C$, $^{15}N$, $^{18}O$, $^{17}O$, $^{18}F$, or $^{36}Cl$. Certain isotopically-labeled compounds of the inventive subject matter, for example those into which $^{14}C$ or $^{3}H$ is incorporated, may be useful in drug and/or substrate tissue distribution assays. On the other hand, substitution with non-radioactive isotopes (e.g., $^{2}H$ or $^{13}C$) can afford certain therapeutic advantages resulting from greater metabolic stability, for example increased in vivo half-life or reduced dosage requirements and, hence, may be preferred in some circumstances.

Contemplated compounds may be prepared as pharmaceutically acceptable salt(s), which especially include salts of acidic or basic groups which may be present in the contemplated compounds. For example, contemplated compounds that are basic in nature may form a wide variety of salts with various inorganic and organic acids. Suitable acids will provide pharmacologically acceptable anions, including chloride, bromide, iodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate[1,1'-methylene-bis-(2-hydroxy-3-naphthoate)]anions. Similarly, compounds that are acidic in nature may form base salts with various pharmacologically acceptable cations, and especially suitable cations include alkali metal or alkaline earth metal ions (e.g., sodium and potassium cations).

It is still further especially contemplated that compounds according to the inventive subject matter may also be prepared as prodrugs, and all known manners and types of prodrugs are considered suitable for use herein, so long as such prodrug will increase the concentration of the drug (or metabolite of the prodrug) at a target organ or target cell.

For example, where the compounds have a free amino, amido, hydroxy, thio, or carboxylic group, it is contemplated that such groups can be employed to covalently and releasably bind a moiety that converts the drug into a prodrug. Therefore, prodrugs particularly include those in which contemplated compounds forms an ester, amide, or disulfide bond with another cleavable moiety. Such moieties may assist in organ or cell-specific delivery of the drug. For instance, a carboxyl group can be derivatized to form an amide or alkyl ester, which may include an ether, amine-, and/or carboxylic acid group. Free hydroxy groups may be derivatized using hemisuccinates, phosphate esters, dimethylaminoacetates, and phosphoryloxymethyloxycarbonyls, as outlined in D. Fleisher, R. Bong, B. H. Stewart, Advanced Drug Delivery 40 Reviews (1996) 19, 115. Carbamate prodrugs of hydroxy and amino groups are also included, as are carbonate prodrugs and sulfate esters of hydroxy groups. Derivatization of hydroxy groups as (acyloxy)methyl and (acyloxy)ethyl-ethers, wherein the acyl group may be an alkyl ester (optionally substituted), or where the acyl group is an amino acid ester are also contemplated (Prodrugs of this type are described in R. P. Robinson et al., J. Medicinal Chemistry (1996) 39:p. 10).

Still further, it should also be recognized that contemplated compounds may be metabolized in a cell or extracellular compartment, and that such metabolites may exhibit the same or different pharmacological effect. For example, contemplated compounds may be phosphorylated and thus be more active than the parent compound. On the other hand, reduction or glycosylation may affect bioavailability of contemplated compounds. Consequently, contemplated compounds will not only include those as described above, but also include metabolites thereof.

Contemplated Pharmaceutical Compositions

Based on the inventors' discovery of biological activity of contemplated compounds, it is generally contemplated that the compounds according to the inventive subject matter may be formulated for treatment of various diseases associated with dysregulation and/or dysfunction of PK receptors and/or overexpression of such receptors. Therefore, and among other contemplated uses, the inventors especially contemplate that pharmaceutical compositions comprising contemplated compounds may be effective for the treatment or prevention of type II diabetes, wherein contemplated pharmaceutical compositions comprise a therapeutically effective amount of contemplated compounds (or pharmaceutically acceptable salt, hydrate, or prodrug thereof), and a pharmaceutically acceptable carrier. For example, in one aspect of the inventive subject matter, contemplated compositions are formulated for treatment of type II diabetes. Viewed from a different perspective, it should be appreciated that type II diabetes and/or symptoms thereof can be prevented or treated by administration of a prokineticin antagonist (wherein suitable antagonists include those than bind to the PK receptor, disrupt and/or prevent PK receptor-ligand interaction, or even bind to a PK receptor ligand). Alternatively, or additionally, contemplated compositions may be formulated for treatment of non-diabetic conditions and include those associated with smooth muscle contraction, pain perception, inflammation, sleep disorders, stress, and neurologic/psychiatric disorders.

It is particularly preferred that contemplated compounds are included in a composition that is formulated with one or more non-toxic pharmaceutically acceptable carriers. Suitable pharmaceutical compositions are preferably formulated for oral administration in solid or liquid form, or for parenteral injection. Thus, it should be appreciated that pharmaceutical compositions according to the inventive subject matter may be administered to humans and other animals using various routes, including orally, rectally, parenterally, intraperitoneally, vaginally, or topically.

For example, suitable pharmaceutical compositions for injection preferably comprise pharmaceutically acceptable sterile aqueous or nonaqueous solutions, dispersions, emulsions, or suspensions, as well as sterile powders for reconstitution into sterile injectable solutions or dispersions prior to use. Examples of suitable aqueous and nonaqueous carriers, diluents, solvents, or vehicles include water, ethanol, polyols (e.g., glycerol, propylene glycol, polyethylene glycol, etc.), and suitable mixtures thereof, oils, and injectable organic esters (e.g., ethyl oleate). Contemplated compositions may also contain various inactive ingredients, including preservatives, wetting agents, emulsifying agents, and/or dispersing agents. Sterility may be ensured by inclusion of antibacterial and/or antifungal agents (e.g., paraben, phenol sorbic acid, chlorobutanol, etc.). Where appropriate, osmotically active agents may be included (e.g., sugars, sodium chloride, etc.).

Alternatively, contemplated compositions may be formulated into solid dosage forms for oral administration, and may therefore be capsules, tablets, pills, powders, and granules. In preferred solid dosage forms, contemplated compound are mixed with at least one of a pharmaceutically acceptable excipient or carrier (e.g., sodium citrate or dicalcium phosphate), a filler or extender (e.g., starch, lactose, sucrose, glucose, mannitol, or silicic acid), a binder (e.g., carboxymethylcellulose, alginates, gelatin, polyvinylpyrrolidone, sucrose, etc.), a humectant (e.g., glycerol), a disintegrating agent (e.g., agar-agar, calcium carbonate, potato or tapioca starch, alginic acid, certain silicates, or sodium carbonate), a solution retarding agent (e.g., paraffin), an absorption accelerator (e.g., quaternary ammonium compound), a wetting agents (e.g., cetyl alcohol and glycerol monostearate), and absorbents (e.g., kaolin, or bentonite clay), and a lubricant (e.g., talc, calcium stearate, magnesium stearate, solid polyethylene glycols, sodium lauryl sulfate).

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. Contemplated compositions may further be formulated to release the active ingredient(s) only, or preferentially, in a certain part of the intestinal tract, optionally, in a delayed manner. Examples of embedding compositions which can be used include polymeric substances and waxes. Contemplated compounds may also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, liquid dosage forms may contain inert diluents commonly used in the art (e.g., water, or other solvent, solubilizing agents), emulsifiers (e.g., ethyl alcohol, isopropyl alcohol, ethyl carbonate, ethyl acetate, benzyl alcohol, benzyl benzoate, propylene glycol, 1,3-butylene glycol, dimethyl formamide), oils (and in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions may also include adjuvants such as wetting agents, emulsifying and suspending agents, sweetening, flavoring, and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound. Compounds according to the inventive subject matter can also be administered in form of liposomes, which may be unilamellar, oligolamellar, or polylamellar. Contemplated compositions in liposome form may further contain stabilizers, preservatives, excipients, etc. Preferred lipids for liposome formation include phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

Actual dosage levels of contemplated compounds in pharmaceutical compositions according to the inventive subject matter may be varied so as to obtain an amount of contemplated compound(s) that is effective to achieve the desired therapeutic response for a particular patient, composition, and mode of administration. Thus, the selected dosage level will depend upon various factors, including the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. Generally, dosage levels of about 0.01 mg to about 500 mg, more preferably of about 0.5 mg to about 50 mg of contemplated compound per kilogram of body weight per day are administered orally to a mammalian patient. If desired, the effective daily dose may be divided into multiple doses for purposes of administration, e.g., two to four separate doses per day.

It should still further be appreciated that contemplated pharmaceutical compositions may also include additional pharmaceutically active compounds, and especially contemplated additional pharmaceutically active compounds include anti-diabetic agents, which may act on insulin production, insulin release, insulin sensitivity, and glucose uptake into a cell. Still other suitable active agents include anti-inflammatory agents, drugs that stimulate or modify metabolism, neurologically active drugs, and/or analgesic drugs. Of course, it should be recognized that additional pharmaceutically active compounds may be included in the same pharmaceutical composition, or may be administered separately, and a person of ordinary skill in the art will readily determine schedule and route of suitable co-administration of the additional pharmaceutically active compounds. It should still further be appreciated that contemplated compositions may also include metabolites and/or prodrug forms of contemplated compounds, and that all compounds may be present in racemic mixture or sterochemically pure (or partially purified) form.

Exemplary Routes of Synthesis

Synthesis of the compound of Formula A can be accomplished through a variety of methods, and in accord with its structural subcategory. In general, structure I can be broken down into two main precursors, an amino acid II and an amine III, which could be a primary or secondary amine, as depicted in Scheme 1.

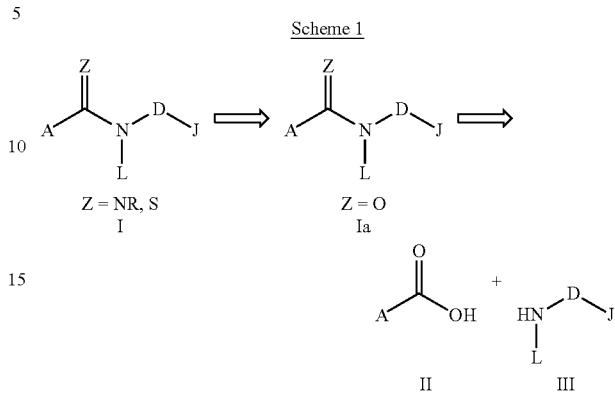

Amine III is usually prepared from alkylation of an alkyl amine L-NH2 (IIIa) with an arylcarboaldehyde (IIIb) under reductive amination conditions, such as sodium triacetoxy borohydride in the presence of acetic acid as reagents and in an appropriate solvent such as dichloroethane (Tetrahedron Letters, 1990, 5595), as in Scheme 2.

Amino acid II is subcategorized into cyclic amino acid as defined in Formula A which contains E or G, or linear amino acid, all of which bearing an arylalkyl substituent on the amino group or a neighboring atom. When the arylalkyl group is substituted on the amino group of the amino acid, usually the connection is made via a reductive amination step with a desired aldehyde under the common reagents such as sodium triacetoxy borohydride in the presence of acetic acid and in an appropriate solvent such as dichloroethane (Tetrahedron Letters, 1990, 5595), as shown in Scheme 3.

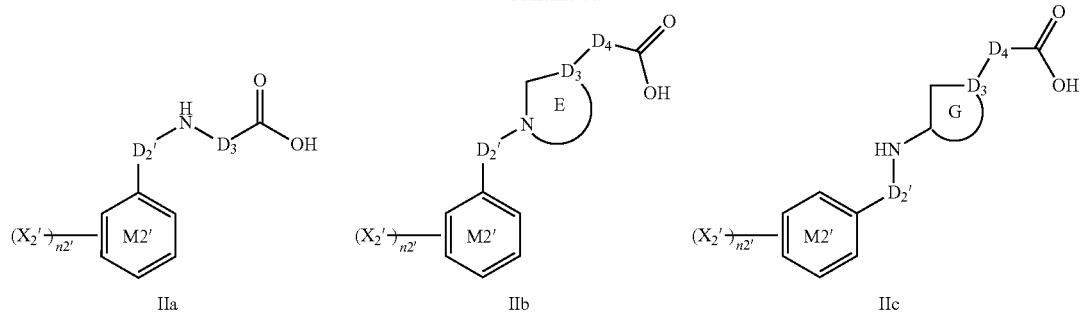

IIa    IIb    IIc

Thus, the final molecule Ia can then be coupled together with amino acid II and amine III under the usual amide coupling conditions, using EDAC/HOBt or HOAt as coupling reagents, with/without DMAP, in a desired solvent such as DCM, or THF, or DMF. (Scheme 4)

Scheme 4

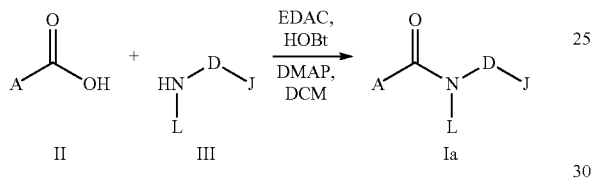

II    III    Ia

Alternatively, Compound III may be coupled with an appropriately protected (Boc, Fmoc, or CBZ, etc) amino acid to form amide IX. Then releasing the amino group via a deprotection procedure was followed by a second reductive amination of the amino group with a desired aldehyde to give Compound Ia, as presented in Scheme 5.

Scheme 5

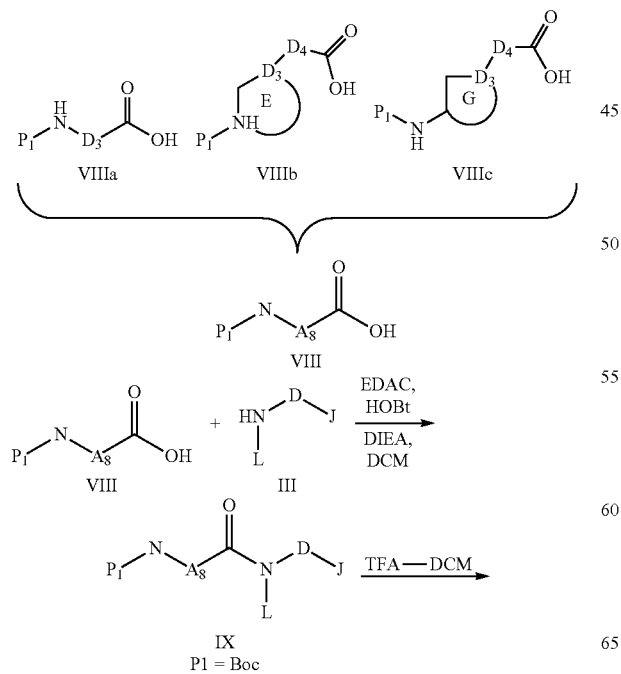

VIIIa    VIIIb    VIIIc

VIII

VIII + III → IX
P1 = Boc

A substituted amino acid precursor such as IIa and IIc can also be prepared via reductive amination between a ketoacid (or ester) and a properly substituted amine, as depicted in Scheme 6.

Scheme 6

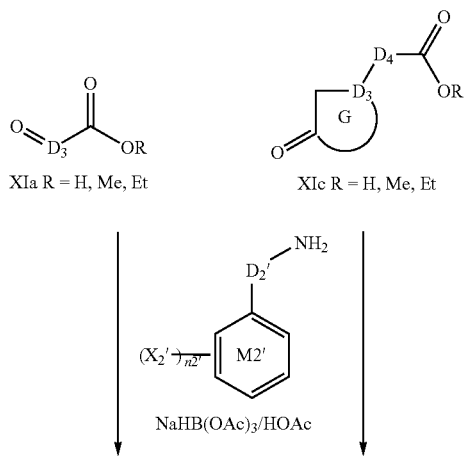

XIa R = H, Me, Et    XIc R = H, Me, Et

NaHB(OAc)3/HOAc

-continued

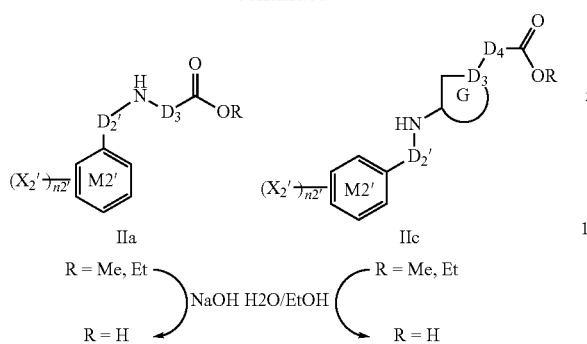

Specifically, alkylamine is alkylated with arylcarboaldehyde 1 under reductive amination conditions. The resulting secondary amine was then coupled with a Boc protected β-proline 4 to give amide 5, the Boc group is then removed via treatment of TFA to give 6. Second reductive amination with the desired arylcarboaldehyde 7 afforded the final desired compound 8, as in Scheme 7.

Scheme 7

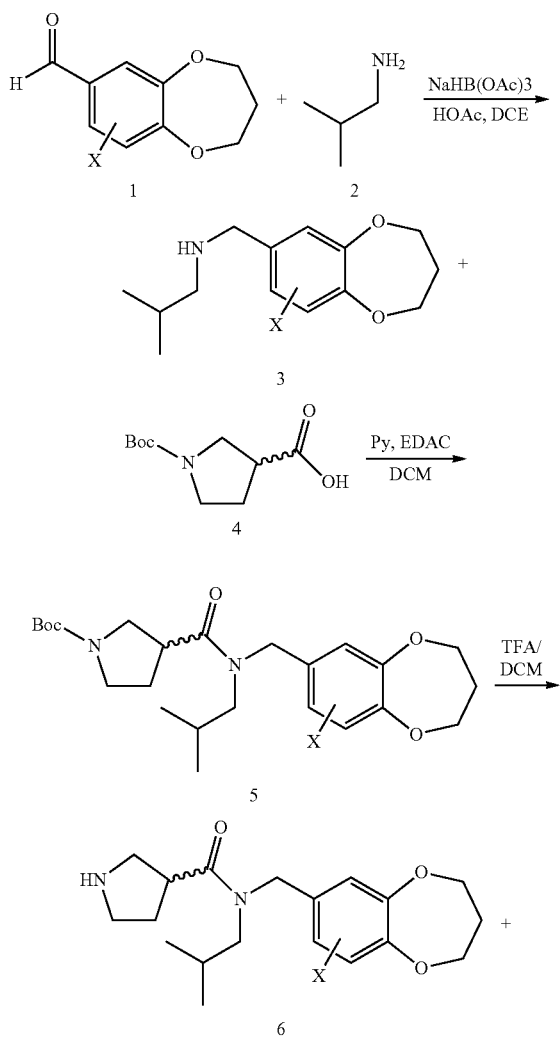

-continued

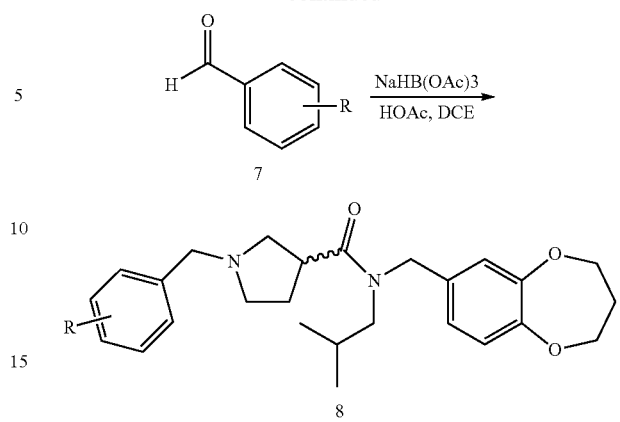

Some selection of starting aldehyde 1 is not readily available commercially. The following are examples of some are made with commercially available starting materials. As described in Scheme 8, halogenated secondary amine 13 was prepared from hydrolysis of starting monoether 9, followed by dioxepine ring formation to give the benzodioxepine-carboaldehyde 12, which leads to the desired amine 13.

Scheme 8

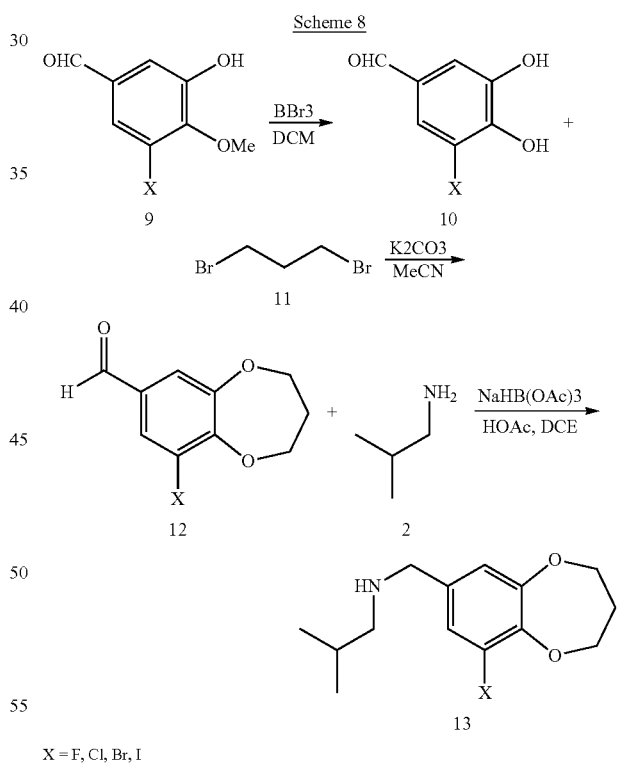

X = F, Cl, Br, I

Exemplary Synthesis of Contemplated Compounds

It should generally be appreciated that contemplated compounds may be prepared from various precursors following numerous routes (either individually, serially, or in parallel fashion, or even using combinatorial synthetic strategies).

The following is therefore only provided as exemplary guidance for starting materials, conditions, and synthesis of selected compounds.

Example 1

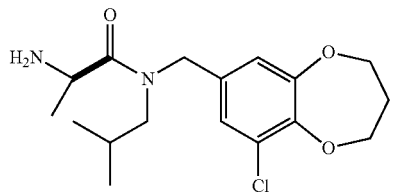

(+)-(2S)-2-Amino-N-(9-chloro-3,4-dihydro-2H-1,5-benzodioxepin-7-ylmethyl)-N-isobutylpropanamide Step 1: 3-chloro-4,5-dihydroxy benzaldehyde: A solution of 19.1 g 3-chloro-4-hydroxy-5-methoxy benzaldehyde in dichloromethane (1600 ml) was cooled in ice water bath. Boron tribromide (53.8 g) in dichloromethane (80 ml) were added and the mixture was stirred for two hours at ambient temperature and then was concentrated. The residue was cooled again with ice water bath and precipitated with ice-cold aqueous hydrochloric acid (1N, 500 ml). Solid residue was received upon filtration, then washed with ice water (500 ml) and dried in the air to obtain 19.3 g crude product of 3-chloro-4,5-dihydroxy benzaldehyde, which was used for the following step.

Step 2: 9-chloro-3,4-dihydro-2H-1,5-benzodioxepine-7-carbaldehyde: A mixture of 3-chloro-4,5-dihydroxy benzaldehyde (4.15 g), of 1,3-dibromopropane (4.71 g, 0.92 eq.) and potassium carbonate (8.28 g, 2.5 eq.) in acetonitrile (160 ml) was heated to 60° C. overnight. The mixture was allowed to cool to room temperature and filtered. The filtrate was concentrated under reduced pressure. The residue was purified by flash chromatography on silica (20% ethyl acetate in hexanes) to give the product as a white crystal. MS (m+1)=212.1

Step 3: N-(9-chloro-3,4-dihydro-2H-1,5-benzodioxepin-7-ylmethyl)-2-methylpropan-1-amine: To an ice cold mixture of 9-chloro-3,4-dihydro-2H-1,5-benzodioxepine-7-carbaldehyde (2.07 g) and of isobutylamine (7.5 ml 8 eq.) were combined in 1,2-dichloroethane (75 ml) and cooled in ice water bath. Acetic acid (5.68 ml) was then added and followed by sodium triacetoxyborohydride (2.75 g, 1.4 eq.). The mixture was allowed to stir at room temperature overnight. It was partitioned with aqueous K2CO3 (75 mL, 1.5M). The aqueous layer was extracted with of dichloromethane (75 ml×2). The organic layers were combined, washed with brine, dried over sodium sulfate, and concentrated. The residue was purified by flash column chromatography (10-100% ethyl acetate in hexanes) gave the desired amine as a light yellow oil: MS (m+1)=270.2.

Step 4: (+)-(2S)-2-(Methylpropan-2-yl)oxycarbonylamino-N-(9-chloro-3,4-dihydro-2H-1,5-benzodioxepin-7-ylmethyl)-N-isobutylpropanamide: A mixture of N-(9-chloro-3,4-dihydro-2H-1,5-benzodioxepin-7-ylmethyl)-2-methylpropan-1-amine (100 mg), Boc-L-alanine (70 mg), EDAC (100 mg), and DMAP (60 mg) in DCM (8 ml) was stirred overnight. The reaction mixture was partitioned between EtOAc and water (8 ml each×3). The organic layers were combined, washed with brine, dried over anhydrous sodium sulfate, and concentrated under reduced pressure. The residue was purificatied by flash chromatography on silica (33% EtOAc in hexane), which yielded (+)-(2S)-2-(Methylpropan-2-yl)oxycarbonylamino-N-(9-chloro-3,4-dihydro-2H-1,5-benzodioxepin-7-ylmethyl)-N-isobutylpropanamide as a resin: MS (m+1)=441.1. The chiral integrity of this compound was not examined.

Step 5: (+)-(2S)-2-Amino-N-(9-chloro-3,4-dihydro-2H-1,5-benzodioxepin-7-ylmethyl)-N-isobutylpropanamide: The above product was dissolved in DCM (2.5 ml) and TFA (2.5 ml) was added. After stirring for one hour at room temperature, the reaction mixture was concentrated under reduced pressure. The residue was partitioned between dichloromethane (5 ml), and aqueous Na2CO3 (Sat., 10 ml). The aqueous layer was extracted with 5 ml of dichloromethane twice. After washing with Brine, the combined organic layers were dried with anhydrous sodium sulfate and concentrated under reduced pressure to yield a resin: MS (m+1)=341.1; H NMR (500 MHz, CDCl3) 0.95 (m, 6H), 1.35 (dd, 3H), 2.00 (m, 1H), 2.25 (m, 2H), 2.90 (q, 1H), 3.05 (q, 1H), 3.15 (q, 1H), 3.60 (q, 1H), 3.70 (d, 1H), 3.90 (d, 1H), 4.15 (d, 1H), 4.25 (m, 2H), 4.40-5.35 (m, 2H), 6.7-7.0 (m, 2H). The chiral integrity of this compound was not examined.

Example 2

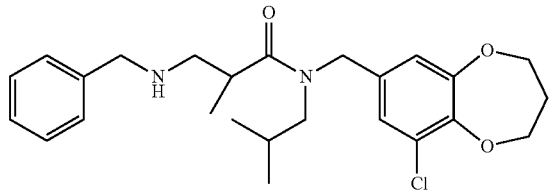

(±)-2-Methyl-3-(benzylamino)-N-(9-chloro-3,4-dihydro-2H-1,5-benzodioxepin-7-ylmethyl)-N-isobutylpropanamide Step 1: (±)-2-Methyl-3-[(2-methylpropan-2-yl)oxycarbonylamino]propanoic acid: A mixture of (±)-2-Methyl-3-aminopropanoic acid (700 mg), di-tert-butyl pyrocarbonate (2.219 g), and triethylamine (1.375 g) in DCM (200 ml) was stirred over night in room temperature. The solvent was evaporated in vac and the solid residue was used for the next step.

Step 2: (±)-2-Methyl-3-(methylpropan-2-yl)oxycarbonylamino-N-(9-chloro-3,4-dihydro-2H-1,5-benzodioxepin-7-ylmethyl)-N-isobutylpropanamide: The mixture of N-(9-chloro-3,4-dihydro-2H-1,5-benzodioxepin-7-ylmethyl)-2-methylpropan-1-amine (600 mg), (±)-2-Methyl-3-[(2-methylpropan-2-yl)oxycarbonylamino]propanoic acid (200 mg), 1-ethyl-3-(3-dimethylaminopropyl)-carbodiimide hydrochloride (475 mg) and of dimethyl aminopyridine (284 mg) in DCM (30 ml) was stirred overnight. The reaction mixture was partitioned between ethyl acetate and water (30 mL each). The aqueous layer was extracted with EtOAc (30 mL×2). The combined organic layer was washed with brine, dried over anhydrous sodium sulfate, and concentrated under reduced pressure. The residue was purified by flash chromatography on silica (33% ethyl acetate in hexane) to give (±)-2-Methyl-3-(methylpropan-2-yl)oxycarbonylamino-N-(9-chloro-3,4-dihydro-2H-1,5-benzodioxepin-7-ylmethyl)-N-isobutylpropanamide as a resin: MS (m+1)=455.5.

Step 3: (±)-2-Methyl-3-amino-N-(9-chloro-3,4-dihydro-2H-1,5-benzodioxepin-7-ylmethyl)-N-isobutylpropanamide: The above (±)-2-Methyl-3-(methylpropan-2-yl)oxycarbonylamino-N-(9-chloro-3,4-dihydro-2H-1,5-benzodioxepin-7-ylmethyl)-N-isobutylpropanamide was dissolved in dichloromethane (3 ml) and treated with trifluoroacetic acid (3 ml). After stirring for two hours at room temperature, the reaction mixture was concentrated under reduced pressure. The residue was partitioned between dichloromethane (10 mL) and aq. sodium carbonate (sat., 10 mL). The aqueous layer was extracted with dichloromethane (10 ml×2). After washing with brine, the organic layer was dried with anhydrous sodium sulfate and concentrated under reduced pressure to yield a resin: MS (m+1)=355.5.

Step 4: (±)-2-Methyl-3-(benzylamino)-N-(9-chloro-3,4-dihydro-2H-1,5-benzodioxepin-7-ylmethyl)-N-isobutylpropanamide: The mixture of (±)-2-Methyl-3-amino-N-(9-chloro-3,4-dihydro-2H-1,5-benzodioxepin-7-ylmethyl)-N-isobutylpropanamide (85 mg), of benzaladehyde (20 mg), of glacial acetic acid (90 μl), and sodium triacetoxyborohydride (51 mg) in dichloromethane (5 ml) was stirred overnight. After the addition of aq. Na2CO3 (1N, 10 mL), the mixture was extracted with 5 ml of ethyl acetate three times. Organic layers were combined, washed with brine (20 ml), dried over anhydrous sodium sulfate, and concentrated. The residue was purified via flash chromatography on silica (20-50% ethyl acetate in hexane) and yielded (±)-2-Methyl-3-(benzylamino)-N-(9-chloro-3,4-dihydro-2H-1,5-benzodioxepin-7-ylmethyl)-N-isobutylpropanamide as a resin: MS (m+1)= 445.2; H NMR (500 MHz, CDCl3) 0.95 (m, 6H), 1.20 (dd, 3H), 2.00 (m, 1H), 2.25 (m, 2H), 2.60 (q, 1H), 2.70 (m, 1H), 2.90 (m, 1H), 3.05 (m, 1H), 3.15 (m, 1H), 3.35 (q, 1H), 3.80 (m, 2H), 4.15 (m, 2H), 4.30 (m, 2H), 4.55 (m, 2H), 6.7-7.0 (m, 2H), 7.2-7.4 (m, 5H).

Example 3

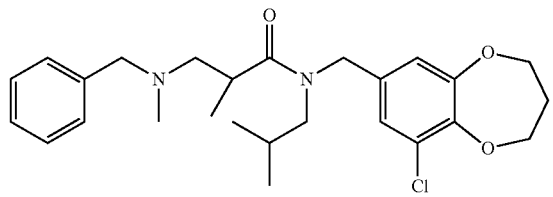

(±)-2-Methyl-3-(benzyl(methyl)amino)-N-(9-chloro-3,4-dihydro-2H-1,5-benzodioxepin-7-ylmethyl)-N-isobutylpropanamide Step 1: (±)-2-Methyl-3-(benzyl(methyl)amino)-N-(9-chloro-3,4-dihydro-2H-1,5-benzodioxepin-7-ylmethyl)-N-isobutylpropanamide: A mixture of (±)-2-Methyl-3-(benzylamino)-N-(9-chloro-3,4-dihydro-2H-1,5-benzodioxepin-7-ylmethyl)-N-isobutylpropanamide (26 mg), paraformaldehye (16 mg), glacial acetic acid (90 μl) and sodium triacetoxyborohydride (26 mg) was dissolved in tetrahydrofuran (5 ml), and stirred overnight. The mixture was partitioned between aq. potassium carbonate (1N, 10 mL) and ethyl acetate (15 ml). The organic layer was concentrated and the residue was purified by flash chromatography on silica (40% ethyl acetate in hexane) to yield a resin: MS (m+1)= 459.2; H NMR (500 MHz, CDCl3) 0.95 (m, 6H), 2.00 (m, 1H), 2.05 (m, 1H), 2.25 (m, 2H), 2.30 (m, 3H), 2.55 (t, 1H), 2.65 (t, 1H), 2.90 (m, 1H), 3.05 (d, 1H), 3.25 (d, 1H), 3.60 (m, 2H), 4.15 (m, 2H), 4.35 (m, 2H), 4.50 (m, 2H), 6.6-7.0 (m, 2H), 7.0-7.5 (m, 5H).

Example 4

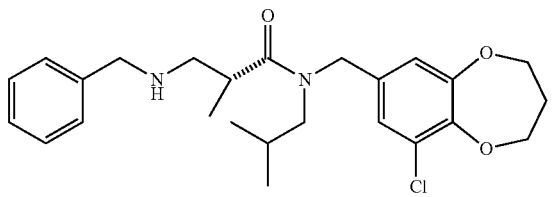

(−)-(2R)-2-Methyl-3-(benzylamino)-N-(9-chloro-3,4-dihydro-2H-1,5-benzodioxepin-7-ylmethyl)-N-isobutylpropanamide Employing a similar procedure as described for Examples 1 and 2, starting with the commercial available (−)-(2R)-2-Methyl-3-aminopropanoic acid, the title compound was obtained as a resin: MS (m+1)=445.2; H NMR (500 MHz, CDCl3) 0.95 (m, 6H), 1.20 (dd, 3H), 2.00 (m, 1H), 2.25 (m, 2H), 2.60 (q, 1H), 2.70 (m, 1H), 2.90 (m, 1H), 3.05 (m, 1H), 3.15 (m, 1H), 3.35 (q, 1H), 3.80 (m, 2H), 4.15 (m, 2H), 4.30 (m, 2H), 4.55 (m, 2H), 6.7-7.0 (m, 2H), 7.2-7.4 (m, 5H).

Example 5

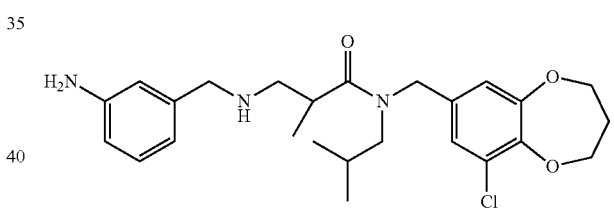

(±)-2-Methyl-3-((2-amino)benzylamino)-N-(9-chloro-3,4-dihydro-2H-1,5-benzodioxepin-7-ylmethyl)-N-isobutylpropanamide Step 1: (±)-2-Methyl-3-((2-nitro)benzylamino)-N-(9-chloro-3,4-dihydro-2H-1,5-benzodioxepin-7-ylmethyl)-N-isobutylpropanamide: A mixture of (±)-2-Methyl-3-amino-N-(9-chloro-3,4-dihydro-2H-1,5-benzodioxepin-7-ylmethyl)-N-isobutylpropanamide (94 mg), 3-nitrobenzaldehyde (40 mg), glacial acetic acid (90 μl), and sodium triacetoxyborohydride (78 mg) in dichloromethane (5 ml) was stirred overnight. The reaction mixture was partitioned between aq. K2CO3 (1N, 10 mL) and ethyl acetate (5 ml). The aqueous was washed with EtOAc (5 mL×2). Organic layers were combined, washed with brine, dried with anhydrous sodium sulfate, and concentrated. The residue was purified by flash chromatography on silica (20-50% ethyl acetate in hexane) and yielded (±)-2-Methyl-3-((2-nitro)benzylamino)-N-(9-chloro-3,4-dihydro-2H-1,5-benzodioxepin-7-ylmethyl)-N-isobutylpropanamide as a resin: MS (m+1)= 490.3.

Step 2: (±)-2-Methyl-3-((2-amino)benzylamino)-N-(9-chloro-3,4-dihydro-2H-1,5-benzodioxepin-7-ylmethyl)-N- isobutylpropanamide: A mixture of (±)-2-Methyl-3-((2-nitro)benzylamino)-N-(9-chloro-3,4-dihydro-2H-1,5-benzodioxepin-7-ylmethyl)-N-isobutylpropanamide (80 mg), ammonium chloride (53 mg), and zinc powder (106 mg) in 6 ml of EtOH—H2O (9-10) was stirred overnight, and then filtered through a layer of zeolite. The filtercake was rinsed with methanol (5 ml×3), and the combined filtrate was concentrated under reduced pressure. The residue was then partitioned between of dichloromethane and saturated aq. sodium bicarbonate (6 ml each). The aqueous layer was then extracted with dichloromethane (6 ml). The organic layer was washed with brine and then concentrated to yield (±)-2-Methyl-3-((2-amino)benzylamino)-N-(9-chloro-3,4-dihydro-2H-1,5-benzodioxepin-7-ylmethyl)-N-isobutylpropanamide as a resin: MS (m+1)=460.3; 1H NMR (500 MHz, CDCl3) 0.95 (m, 6H), 1.15 (dd, 3H), 2.00 (m, 1H), 2.25 (m, 2H), 2.60 (q, 1H), 2.70 (q, 1H), 2.90 (m, 1H), 3.05 (m, 1H), 3.10 (m, 1H), 3.20 (q, 1H), 3.35 (q, 1H), 3.45 (q, 1H), 3.70 (m, 2H), 4.25 (m, 2H), 4.35 (m, 2H), 4.55 (m, 2H), 6.6-7.2 (m, 4H), 6.8-7.0 (m, 2H).

Example 6

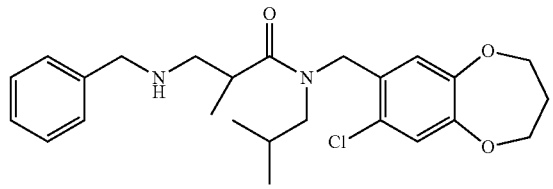 [SMILES: CC(C)CN(Cc1cc2c(cc1Cl)OCCCO2)C(=O)C(C)CNCc1ccccc1]

(±)-2-Methyl-3-(benzylamino)-N-(8-chloro-3,4-dihydro-2H-1,5-benzodioxepin-7-ylmethyl)-N-isobutyl propanamide Employing the same procedure as described for Examples 1 and 2, starting with 6-chloro-1,3-benzodioxole-5-carboxaldehyde (6-chloropiperonal), the title compound was obtained as a resin: MS (m+1)=445.2; 1H NMR (500 MHz, CDCl3) 0.95 (m, 6H), 1.45 (dd, 3H), 2.00 (m, 1H), 2.30 (m, 2H), 2.90 (q, 1H), 3.00 (m, 1H), 3.10 (m, 1H), 3.25 (m, 1H), 3.45 (q, 1H), 3.55 (m, 1H), 4.20 (m, 2H), 4.30 (m, 2H), 4.55 (q, 2H), 5.00 (d, 2H), 6.7-7.1 (m, 2H), 7.4-7.7 (m, 5H).

Example 7

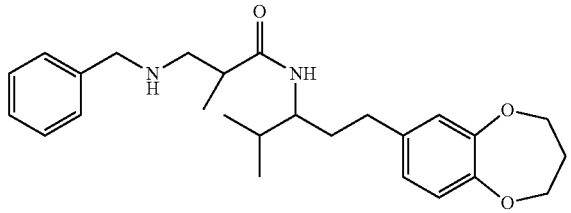 [SMILES: CC(CNCc1ccccc1)C(=O)NC(CCc1ccc2c(c1)OCCCO2)C(C)C]

(±)-2-Methyl-3-(benzylamino)-N-[(3,4-dihydro-2H-1,5-benzodioxepin-7-yl)-4-methylpentan-3-yl]propanamide)

Step 1: 1-(3,4-dihydro-2H-1,5-benzodioxepine-7-yl)-4-methyl-1-penten-3-one: The MeOH (5 mL) solution of 3,4-dihydro-2H-1,5-benzodioxepine-7-carbaldehyde (445 mg) and 3-methyl-2-butanone (195 mg) was treated with aq. sodium hydroxide (1N, 1 ml) and the mixture was stirred for 24 hours. The reaction was partitioned between 10 ml water and 40 ml ethyl acetate. The organic layer was then sequentially washed with aq. hydrochloric acid (1N, 20 ml), water (20 ml), and Brine (20 ml) and then concentrated under reduced pressure. The residue was purified with flash chromatography on silica (33% ethyl acetate in hexane) to give the desired product as a white crystal.

Step 2: 1-(3,4-dihydro-2H-1,5-benzodioxepine-7-yl)-4-methyl-1-penten-3-one oxime: 145 mg 1-(3,4-dihydro-2H-1,5-benzodioxepine-7-yl)-4-methyl-1-penten-3-one was dissolved in methanol (20 ml), along with hydroxylamine hydrocholoride (244 mg) and sodium acetate (480 mg) and stirred in room temperature overnight. The reaction mixture was evaporated and the residue was dissolved in ethyl acetate (30 ml). After washing with 30 mL water and 30 mL Brine and drying with anhydrous sodium sulfate, the organic layer was concentrated under reduced pressure to yield crude product (M+1=262.1), that was used for next reaction.

Step 3: (±)-1-(3,4-dihydro-2H-1,5-benzodioxepine-7-yl)-4-methylpentan-3-ylamine: The above product was dissolved in ethanol (20 ml) and suspended with Pd—C (10%, 60 mg). The hydrogenation was carried in a hydrogen balloon for 3 hrs at room temperature. The reaction mixture was then filtered through a layer of zeolite and the filtercake was rinsed with 10 ml of methanol three times. The combined filtrate was concentrated to give the desired product (M+1=250.1) without further purification.

Step 4: (±)-2-Methyl-3-[(2-methylpropan-2-yl)oxycarbonylamino]-N-[(3,4-dihydro-2H-1,5-benzodioxepin-7-yl)-4-methylpentan-3-yl]propanamide: 50 mg of (±)-1-(3,4-dihydro-2H-1,5-benzodioxepine-7-yl)-4-methylpentan-3-ylamine was mixed with of (±)-2-Methyl-3-[(2-methylpropan-2-yl)oxycarbonylamino]propanoic acid (25 mg), 1-ethyl-3-(3-dimethylaminopropyl)-carbodiimide hydrochloride (53 mg), and DMAP (33 mg) in dichloromethane (5 ml) and stirred overnight. Water (5 ml) was added, and the reaction mixture was extracted with ethyl acetate (5 ml three times). The organic layer was washed with brine, dried over anhydrous sodium sulfate and concentrated under reduced pressure. Purification by flash chromatography on silica (20% ethyl acetate in hexane) yielded a resin: MS (m+1)=435.6.

Step 5: (±)-2-Methyl-3-amino-N-[(3,4-dihydro-2H-1,5-benzodioxepin-7-yl)-4-methylpentan-3-yl]propanamide: The above product was dissolved in dichloromethane (2.5 ml) and trifluoroacetic acid (2.5 ml) was added. After stirring for one hour at room temperature, the reaction mixture was concentrated under reduced pressure. The residual was partitioned between dichloromethane and aq. sodium carbonate (sat., 5 ml each). The aqueous layer was extracted with 5 ml of dichloromethane twice. After washing with Brine, the organic layer was dried with anhydrous sodium sulfate and concentrated under reduced pressure to yield a resin: MS (m+1)=335.6.

Step 6: (±)-2-Methyl-3-(benzylamino)-N-[(3,4-dihydro-2H-1,5-benzodioxepin-7-yl)-4-methylpentan-3-yl]propanamide: 21 mg (±)-2-Methyl-3-amino-N-[(3,4-dihydro-2H-1,5-benzodioxepin-7-yl)-4-methylpentan-3-yl]propanamide, benzaladehyde (6.6 mg), glacial acetic acid (90 μl), and sodium triacetoxyborohydride (19 mg) were mixed in dichloromethane (5 ml) and stirred overnight. After addition of aq. potassium carbonate (1N, 10 mL), the mixture was extracted with ethyl acetate (5 ml three times). Organic layers were combined, washed with brine, dried over anhydrous sodium sulfate, then concentrated in vacuo. Purification by flash chromatography on silica (20% ethyl acetate in hexane) yielded (±)-2-Methyl-3-(benzylamino)-N-[(3,4-dihydro-2H-1,5-benzodioxepin-7-yl)-4-methylpentan-3-yl]propanamide as a resin: MS (m+1)=425.6; H NMR (500 MHz, CDCl3) 0.95 (m, 6H), 1.25 (d, 3H), 1.32 (m, 2H), 1.60 (m, 1H), 1.83 (m, 1H), 2.11 (s, 1H), 2.14 (s, 1H), 2.23 (m, 2H), 2.48 (m, 1H), 2.57 (m, 1H), 2.86 (m, 2H), 3.86 (m, 1H), 3.93 (m, 1H), 4.23 (m, 4H), 6.7-7.0 (m, 3H), 7.3-7.5 (m, 5H).

Example 8

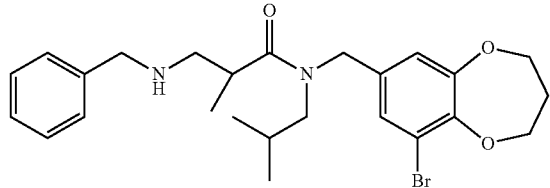 [SMILES: CC(C)CN(Cc1cc(Br)c2c(c1)OCCCO2)C(=O)C(C)CNCc1ccccc1]

(±)-2-Methyl-3-(benzylamino)-N-(9-bromo-3,4-dihydro-2H-1,5-benzodioxepin-7-ylmethyl)-N-isobutylpropanamide Employing the same procedure as described for Examples 1 and 2, starting with 3-bromo-4-hydroxy-5-methoxy benzaldehyde, the title compound was obtained as a resin: MS (m+1)=489.3; 1H NMR (500 MHz, CDCl3) 0.95 (m, 6H), 1.20 (dd, 3H), 2.00 (m, 1H), 2.25 (m, 2H), 2.85 (m, 1H), 2.90 (m, 1H), 3.15 (m, 1H), 3.20 (m, 1H), 3.30 (m, 1H), 3.50 (q, 1H), 3.70 (m, 2H), 4.25 (m, 2H), 4.30 (m, 2H), 4.55 (m, 2H), 6.7-7.1 (m, 2H), 7.2-7.5 (m, 5H).

Example 9

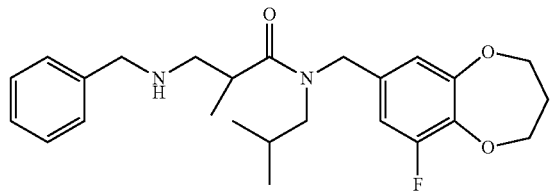 [SMILES: CC(C)CN(Cc1cc(F)c2c(c1)OCCCO2)C(=O)C(C)CNCc1ccccc1]

(±)-2-Methyl-3-(benzylamino)-N-(9-fluoro-3,4-dihydro-2H-1,5-benzodioxepin-7-ylmethyl)-N-isobutylpropanamide Employing the same procedure as described for Examples 1 and 2, starting with 3-fluoro-4-hydroxy-5-methoxy benzaldehyde, the title compound was obtained as a resin: MS (m+1)=429.3; 1H NMR (500 MHz, CDCl3) 0.95 (m, 6H), 1.20 (dd, 3H), 2.00 (m, 1H), 2.25 (m, 2H), 2.60 (q, 1H), 2.70 (m, 1H), 2.90 (m, 1H), 3.05 (m, 1H), 3.15 (m, 1H), 3.35 (q, 1H), 3.80 (m, 2H), 4.25 (m, 2H), 4.30 (m, 2H), 4.55 (m, 2H), 6.6-6.8 (m, 2H), 7.2-7.4 (m, 5H).

Example 10

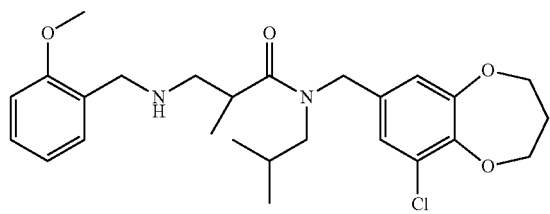 [SMILES: COc1ccccc1CNCC(C)C(=O)N(Cc1cc(Cl)c2c(c1)OCCCO2)CC(C)C]

(±)-2-Methyl-3-((2-methoxy)benzylamino)-N-(9-chloro-3,4-dihydro-2H-1,5-benzodioxepin-7-ylmethyl)-N-isobutylpropanamide Employing the same procedure as described for example 2, starting with 2-methoxy benzaldehyde, the title compound was obtained as a resin: MS (m+1)=475.3; H NMR (500 MHz, CDCl3) 0.95 (m, 6H), 1.15 (dd, 3H), 2.05 (m, 1H), 2.25 (m, 2H), 2.55 (q, 1H), 2.65 (q, 1H), 2.90 (m, 1H), 3.05 (m, 1H), 3.20 (m, 1H), 3.25 (m, 1H), 3.80 (m, 2H), 3.90 (d, 3H), 4.25 (m, 2H), 4.35 (m, 2H), 4.55 (m, 2H), 6.7-7.0 (m, 2H), 6.9-7.3 (m, 4H).

Example 11

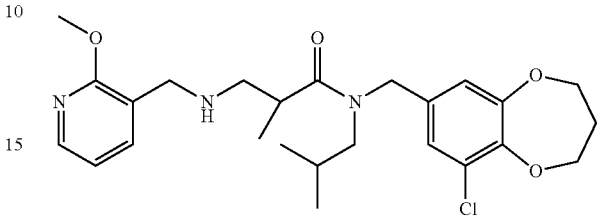

(±)-2-Methyl-3-((2-methoxypyridin-3-ylmethyl)amino)-N-(9-chloro-3,4-dihydro-2H-1,5-benzodioxepin-7-ylmethyl)-N-isobutylpropanamide Employing the same procedure as described for example 2, starting with 2-Methoxy-3-pyridinecarboxaldehyde, the title compound was obtained as a resin: MS (m+1)=476.3; H NMR (500 MHz, CDCl3) 0.95 (m, 6H), 1.20 (dd, 3H), 2.05 (m, 1H), 2.25 (m, 2H), 2.55 (q, 1H), 2.65 (q, 1H), 2.90 (m, 1H), 3.05 (m, 1H), 3.20 (m, 1H), 3.25 (q, 1H), 3.75 (m, 2H), 4.00 (d, 3H), 4.25 (m, 2H), 4.35 (m, 2H), 4.55 (m, 2H), 6.7-7.0 (m, 2H), 6.8-8.1 (m, 3H).

Example 12

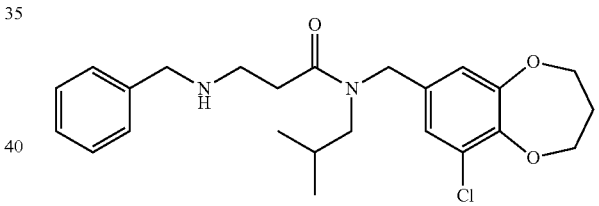

3-(Benzylamino)-N-(9-chloro-3,4-dihydro-2H-1,5-benzodioxepin-7-ylmethyl)-N-isobutylpropanamide Step 1: N-(9-chloro-3,4-dihydro-2H-1,5-benzodioxepin-7-ylmethyl)-N-isobutyl 3-[(2-methylpropan-2-yl)oxycarbonylamino]propanamide: A mixture of N-(9-chloro-3,4-dihydro-2H-1,5-benzodioxepin-7-ylmethyl)-2-methylpropan-1-amine (140 mg), 3-[(2-methylpropan-2-yl)oxycarbonylamino]propanoic acid (Boc-beta-alanine, 98 mg), of 1-ethyl-3-(3-dimethylaminopropyl)carbodiimide hydrochloride (163 mg), and of dimethyl aminopyridine (113 mg) in dichloromethane (10 ml) was stirred overnight. The mixture was concentrated under reduced pressure. Desired compound [N-(9-chloro-3,4-dihydro-2H-1,5-benzodioxepin-7-ylmethyl)-N-isobutyl 3-[(2-methylpropan-2-yl)oxycarbonylamino]propanamide] was isolated by flash chromatography on silica (100% dichloromethane) as a resin: MS (m+1)=441.3.

Step 2: 3-Amino-N-(9-chloro-3,4-dihydro-2H-1,5-benzodioxepin-7-ylmethyl)-N-isobutyl propanamide: The Boc protecting group of N-(9-chloro-3,4-dihydro-2H-1,5-benzodioxepin-7-ylmethyl)-N-isobutyl 3-[(2-methylpropan-2-yl)oxycarbonylamino]propanamide (144 mg) was removed by treating with trifluoroacetic acid in dichloromethane (50%, 10 ml) to yield 3-amino-N-(9-chloro-3,4-dihydro-2H-1,5-benzodioxepin-7-ylmethyl)-N-isobutylpropanamide (111 mg) as a resin.

Step 3: 3-Benzylamino N-(9-chloro-3,4-dihydro-2H-1,5-benzodioxepin-7-ylmethyl)-N-isobutyl-propanamide: The mixture of 3-Amino-N-(9-chloro-3,4-dihydro-2H-1,5-benzodioxepin-7-ylmethyl)-N-isobutyl-propanamide (54 mg), of benzaladehyde (17 mg), glacial acetic acid (90 µl), and of sodium triacetoxyborohydride (67 mg) in DCM (5 ml) was stirred overnight. To the reaction were added distilled water (3 ml) and then aq. potassium carbonate (2M, 5 ml). The mixture was extracted with ethyl acetate (10 ml×2). Organic layers were combined, washed with 40 ml of brine and concentrated. The residue was purified via preparative thin layer chromatography (TLC) on silica (10% MeOH in DCM)) to give the product as a resin: MS (m+1)=431.3; 1H NMR (500 MHz, CDCl3) 0.95 (m, 6H), 1.35 (s, 1H), 2.00 (m, 1H), 2.25 (m, 2H), 2.60 (t, 1H), 2.70 (t, 1H), 2.95 (t, 1H), 3.00 (t, 1H), 3.10 (d, 1H), 3.25 (d, 1H), 3.85 (d, 2H), 4.25 (d, 2H), 4.35 (m, 2H), 4.50 (d, 2H), 6.6-7.0 (m, 2H), 7.1-7.6 (m, 5H).

Example 13

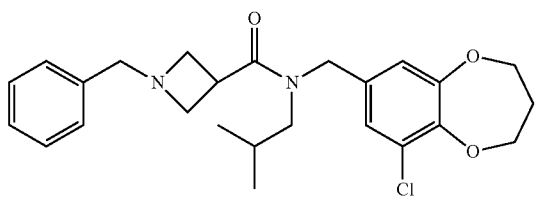 [SMILES: CC(C)CN(Cc1cc(Cl)c2c(c1)OCCCO2)C(=O)C1CN(Cc2ccccc2)C1]

1-Benzyl-N-(9-chloro-3,4-dihydro-2H-1,5-benzodioxepin-7-ylmethyl)-N-isobutyl azetidine-3-carboxamide Step 1: 40 mg of N-(9-chloro-3,4-dihydro-2H-1,5-benzodioxepin-7-ylmethyl)-2-methylpropan-1-amine was combined with 28 mg of 1-benzyl-azetidine-3-carboxylic acid in 5 ml dichloromethane. 38 mg of 1-ethyl-3-(3-dimethylaminopropyl)carbodiimide hydrochloride and 26 mg of dimethyl aminopyridine were added. The reaction solution was stirred at room temperature overnight. 5 ml of water was added and the mixture was extracted with 5 ml ethyl acetate three times. The organic layer was washed with saturated sodium bicarbonate, water and brine, dried over anhydrous sodium phosphate and concentrated under reduced pressure. The product was purified by column chromatography using 75% ethyl acetate in hexane as a resin: MS (m+1)=443.3; 1H NMR (500 MHz, CDCl3) 0.95 (m, 6H), 1.95 (m, 1H), 2.05 (m, 1H), 2.25 (m, 2H), 2.95 (d, 1H), 3.00 (d, 1H), 3.40 (m, 1H), 3.45 (m, 1H), 3.50 (m, 1H), 3.65 (m, 2H), 3.75 (m, 2H), 4.25 (m, 2H), 4.35 (m, 2H), 4.50 (s, 1H), 6.5-7.0 (m, 2H), 7.1-7.4 (m, 5H).

Example 14

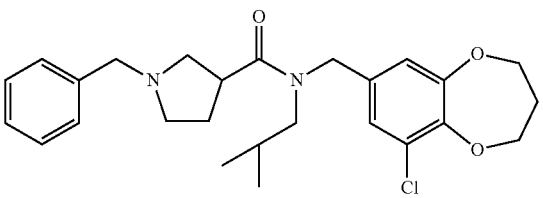 [SMILES: CC(C)CN(Cc1cc(Cl)c2c(c1)OCCCO2)C(=O)C1CCN(Cc2ccccc2)C1]

(±)-1-Benzyl-N-(9-chloro-3,4-dihydro-2H-1,5-benzodioxepin-7-ylmethyl)-N-isobutyl pyrrolidine-3-carboxamide Step 1: (±)-1-Benzyl-N-(3,4-dihydro-2H-1,5-benzodioxepin-7-ylmethyl)-N-isobutylpyrrolidine-3-carboxamide:

The above amine product, N-(9-chloro-3,4-dihydro-2H-1,5-benzodioxepin-7-ylmethyl)-2-methylpropan-1-amine (807 mg, 3 mmole) was combined with 1-Benzyl-pyrrolidine-3-carboxylic acid (615 mg, 3 mmole) in 50 ml dichloromethane. 1-ethyl-3-(3-dimethylaminopropyl)carbodiimide hydrochloride (764 mg, 4 mmole) and dimethyl aminopyridine (562 mg, 4 mmole) were added. The reaction solution was stirred at room temperature overnight. 50 ml of water was added and the mixture was extracted with 50 ml ethyl acetate three times. The organic layer was washed with saturated sodium bicarbonate, water and brine, dried over anhydrous sodium sulfate and concentrated under reduced pressure. The product was purified by column chromatography using 50-75% ethyl acetate in hexane. MS (m+1)=457.3; H NMR (500 MHz, CDCl3) 0.95 (m, 6H), 2.00 (m, 1H), 2.05 (m, 1H), 2.15 (m, 1H), 2.25 (m, 1H), 2.55 (m, 1H), 2.65 (m, 1H), 2.90 (m, 1H), 3.00 (m, 1H), 3.10 (d, 1H), 3.15 (m, 1H), 3.25 (d, 1H), 3.40 (m, 1H), 3.75 (m, 2H), 4.30 (m, 4H), 4.45 (s, 1H), 4.55 (d, 1H), 6.6-7.0 (m, 2H), 7.2-7.5 (m, 5H).

Example 15

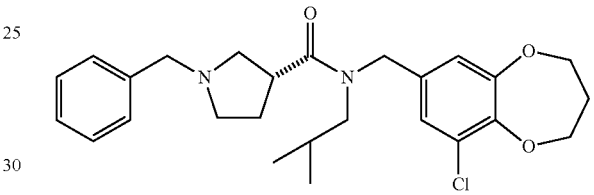

(3R)-1-Benzyl-N-(9-chloro-3,4-dihydro-2H-1,5-benzodioxepin-7-ylmethyl)-N-isobutyl pyrrolidine-3-carboxamide Step 1 (3R)-1-tert-butoxycarbonyl-N-(9-chloro-3,4-dihydro-2H-1,5-benzodioxepin-7-ylmethyl)-N-isobutyl pyrrolidine-3-carboxamide: A mixture of N-(9-chloro-3,4-dihydro-2H-1,5-benzodioxepin-7-ylmethyl)-2-methylpropan-1-amine (1,594 mg), (R)-Pyrrolidine-1,3-dicarboxylic acid 1-tert-butyl ester 1,270 mg, 1-ethyl-3-(3-dimethylaminopropyl)carbodiimide hydrochloride (1,480 mg), dimethyl aminopyridine (1,030 mg) in 110 ml dichloromethane was stirred at room temperature overnight. After addition of water (75 mL), the mixture was extracted with ethyl acetate (100 mL 3). The organic layer was washed with saturated sodium bicarbonate, water and brine, dried over anhydrous sodium sulfate and concentrated under reduced pressure. The product was purified by column chromatography on silica (33-50% ethyl acetate in hexane) and received as an oil: MS (m+1)=467.3.

Step 2: (3R)—N-(9-chloro-3,4-dihydro-2H-1,5-benzodioxepin-7-ylmethyl)-N-isobutyl pyrrolidine-3-carboxamide: The above product was dissolved in dichloromethane (20 ml), then trifluoroacetic acid (20 ml) was added. The mixture was stirred for one hour at room temperature. After the evaporation of the volatiles under reduced pressure, the residue was partitioned between dichloromethane (20 ml) and aq. sodium bicarbonate (sat., 40 mL). The aqueous was extracted with 50 ml of dichloromethane twice. The organic layer was combined, dried with anhydrous sodium sulfate and concentrated under reduced pressure to yield a lightly reddish oil: MS (m+1)=367.3.

Step 3. (3R)-1-Benzyl-N-(9-chloro-3,4-dihydro-2H-1,5-benzodioxepin-7-ylmethyl)-N-isobutyl pyrrolidine-3-carboxamide: A mixture of (3R)—N-(9-chloro-3,4-dihydro-2H-

1,5-benzodioxepin-7-ylmethyl)-N-isobutyl pyrrolidine-3-carboxamide (1,090 mg), benzaladehyde (944 mg), glacial acetic acid (1.8 ml), and sodium triacetoxyborohydride (1,090 mg) in 50 ml dichloromethane was stirred overnight. Upon addition of aq. potassium carbonate (1N, 60 mL), the mixture was extracted with ethyl acetate (60 ml×2). Organic layers were combined, washed with brine and concentrated. Flash chromatography on silica (33-75% ethyl acetate in hexane) gave the product as a resin: MS (m+1)=457.3; 1H NMR (500 MHz, CDCl3) 0.95 (m, 6H), 2.00 (m, 1H), 2.05 (m, 1H), 2.15 (m, 1H), 2.25 (m, 1H), 2.55 (m, 1H), 2.65 (q, 1H), 2.90 (m, 1H), 3.00 (m, 1H), 3.10 (d, 1H), 3.15 (m, 1H), 3.25 (d, 1H), 3.40 (m, 1H), 3.75 (m, 2H), 4.30 (m, 4H), 4.45 (s, 1H), 4.55 (d, 1H), 6.6-7.0 (m, 2H), 7.2-7.5 (m, 5H).

Example 16

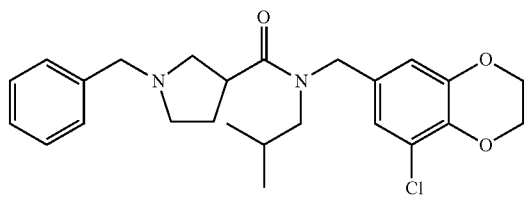 [SMILES: CC(C)CN(Cc1cc(Cl)c2c(c1)OCCO2)C(=O)C1CCN(Cc2ccccc2)C1]

(±)-1-Benzyl-N-(8-chloro-2,3-dihydro-1,4-benzodioxin-6-ylmethyl)-N-isobutyl pyrrolidine-3-carboxamide This compound was prepared in the same manner as described for example 14 from commercially available 8-chloro-2,3-dihydro-1,4-benzodioxine-6-carbaldehyde. The product was obtained as a resin: MS (m+1)=443.3; 1H NMR (500 MHz, CDCl3) 0.95 (m, 6H), 2.00 (m, 1H), 2.05 (m, 1H), 2.15 (m, 1H), 2.25 (m, 1H), 2.55 (m, 1H), 2.65 (q, 1H), 2.90 (m, 1H), 3.00 (m, 1H), 3.10 (m, 1H), 3.20 (m, 1H), 3.25 (d, 1H), 3.40 (m, 1H), 3.70 (m, 2H), 4.30 (m, 2H), 4.40 (m, 2H), 4.50 (m, 2H), 6.5-6.9 (m, 2H), 7.2-7.5 (m, 5H).

Example 17

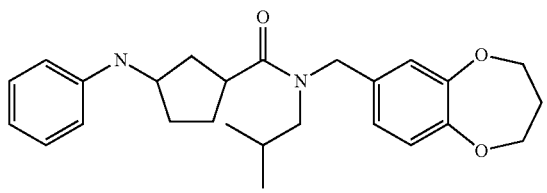 [SMILES: CC(C)CN(Cc1ccc2c(c1)OCCCO2)C(=O)C1CCC(Nc2ccccc2)C1]

(±)-N-(3,4-dihydro-2H-1,5-benzodioxepin-7-ylmethyl)-N-isobutyl-3-(phenylamino)cyclopentanecarboxamide Step 1: 3-Oxo-cyclopentanecarboxylic acid benzyl ester: The mixture of 3-oxo-cyclopentanecarboxylic acid (750 mg), of benzyl alcohol (633 mg), 1-ethyl-3-(3-dimethylaminopropyl)carbodiimide hydrochloride 1 (680 mg), and of 1-hydroxybenzotriazole (350 mg) in 50 ml tetrahydrofuran was stirred overnight. After addition of aq. Sodium bicarbonate (sat. 25 mL), the reaction mixture was extracted with of ethyl acetate (50 ml×2). The organic layer was washed with brine, dried with anhydrous sodium sulfate and concentrated to yield 3-oxo-cyclopentanecarboxylic acid benzyl ester as oil.

Step 2: 3-Phenylaminocyclopentanecarboxylic acid benzyl ester: The mixture of 3-oxocyclopentanecarboxylic acid benzyl ester (150 mg), aniline (75 mg), glacial acetic acid (200 µL), and sodium triacetoxyborohydride (230 mg) in DCM (20 mL) was stirred overnight. Upon the addition of aq. potassium carbonate (1M, 30 mL), the mixture was extracted with ethyl acetate (30 ml×2). Organic layers were combined, washed with brine, and concentrated. Flash chromatography on silica (50% ethyl acetate in hexane) gave the product as an oil: MS (m+1)=282.3.

Step 3: 3-Phenylaminocyclopentanecarboxylic acid: Benzyl ester of 3-phenylaminocyclopentanecarboxylic acid (65 mg) was dissolved in tetrahydrofuran (5 mL) and aq. hydrochloride (6N, 5 mL). The mixture was stirred at room temperature overnight. The solvent was removed in vacuo to yield the hydrochloric salt of the desired product, which was used for the next reaction without further purification.

Step 4: (±)-N-(3,4-dihydro-2H-1,5-benzodioxepin-7-ylmethyl)-N-isobutyl-3-(phenylamino)cyclopentanecarboxamide: The mixture of N-(9-chloro-3,4-dihydro-2H-1,5-benzodioxepin-7-ylmethyl)-2-methylpropan-1-amine (17 mg), 3-phenylaminocyclopentanecarboxylic acid (15 mg), 1-ethyl-3-(3-dimethylaminopropyl)carbodiimide hydrochloride (20 mg), and N,N-dimethyl-4-aminopyridine (12 mg) in 5 ml dichloromethane was stirred at room temperature overnight. After addition of water (5 mL), the mixture was extracted with ethyl acetate (10 ml×2). The organic layer was washed with brine, dried over anhydrous sodium sulfate, and concentrated under reduced pressure. Preparative thin layer chromatography on silica (33% ethyl acetate in hexane) gave the product as a resin: MS (m+1)=423.3; H NMR (500 MHz, CDCl3) 0.95 (m, 6H), 1.30 (m, 4H), 1.75 (m, 2H), 1.90 (m, 1H), 1.95 (m, 1H), 2.15 (m, 1H), 2.30 (m, 1H), 2.65 (m, 2H), 3.00 (m, 1H), 4.00 (m, 2H), 4.40 (m, 2H), 4.15 (m, 4H), 5.20 (s, 1H), 6.6-6.8 (m, 3H), 7.1-7.6 (m, 5H).

Example 18

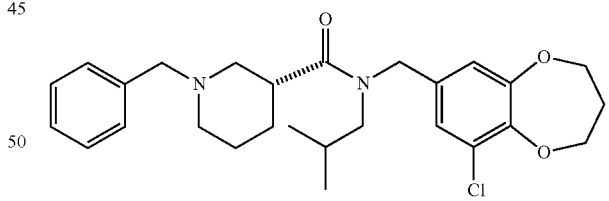

(3R)-1-Benzyl-N-(9-chloro-3,4-dihydro-2H-1,5-benzodioxepin-7-ylmethyl)-N-isobutyl piperidine-3-carboxamide This compound was prepared in the same manner as described for example 14 starting from commercially available (R)-Piperidine-1,3-dicarboxylic acid 1-tert-butyl ester (N-boc-nipecotic acid). The product was obtained as a resin: MS (m+1)=471.3; 1H NMR (500 MHz, CDCl3) 0.95 (m, 6H), 1.65 (m, 1H), 1.75 (m, 1H), 1.80 (m, 1H), 1.90 (m, 1H), 2.00 (m, 1H), 2.25 (m, 2H), 2.45 (d, 1H), 2.80 (m, 1H), 3.00 (m, 1H), 3.10 (d, 1H), 3.20 (d, 1H), 3.55 (m, 1H), 3.65 (m, 1H), 3.75 (d, 1H), 3.80 (m, 1H), 4.30 (m, 4H), 4.4-4.6 (m, 2H), 6.6-7.0 (m, 2H), 7.0-7.5 (m, 5H).

Example 19

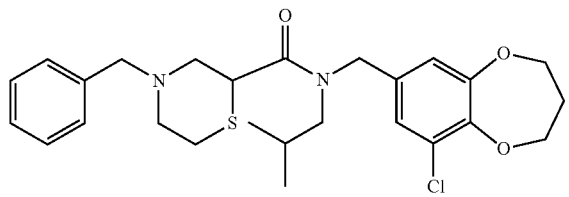 [SMILES: CC(C)CN(Cc1cc(Cl)c2c(c1)OCCCO2)C(=O)C1CN(Cc2ccccc2)CCS1]

(±)-4-Benzyl-N-(9-chloro-3,4-dihydro-2H-1,5-benzodioxepin-7-ylmethyl)-N-isobutyl thiomorpholine-2-carboxamide Step 1 (±)-4-tert-butoxycarbonyl-N-(9-chloro-3,4-dihydro-2H-1,5-benzodioxepin-7-ylmethyl)-N-isobutyl thiomorpholine-2-carboxamide: The mixture of N-(9-chloro-3,4-dihydro-2H-1,5-benzodioxepin-7-ylmethyl)-2-methylpropan-1-amine (150 mg), thiomorpholine-2,4-dicarboxylic acid 4-tert-butyl ester (137 mg), 1-ethyl-3-(3-dimethylaminopropyl)carbodiimide hydrochloride (138 mg), and dimethyl aminopyridine (92 mg) in dichloromethane (15 ml) was stirred at room temperature overnight. After the addition of water (10 ml), the mixture was extracted with 10 ml ethyl acetate three times. The organic layer was washed with saturated sodium bicarbonate, water and brine, dried over anhydrous sodium sulfate and concentrated under reduced pressure. The crude was purified by column chromatography on silica (20-33% ethyl acetate in hexane) to give the desired product as a resin: MS (m+1)=499.4.

Step 2: (±)-N-(9-chloro-3,4-dihydro-2H-1,5-benzodioxepin-7-ylmethyl)-N-isobutyl thiomorpholine-2-carboxamide: The above product was dissolved in 2.5 ml dichloromethane, and 2.5 ml of trifluoroacetic acid was added. The mixture was stirred for one hour at room temperature. After the evaporation of the volatiles under reduced pressure, the residue was partitioned between dichloromethane and aq. sodium bicarbonate (sat., 10 mL ea). The aqueous was extracted with dichloromethane (10 ml×2). The combined organic layer was dried with anhydrous sodium sulfate and concentrated under reduced pressure to yield a colorless oil: MS (m+1)=399.2.

Step 3. (±)-4-Benzyl-N-(9-chloro-3,4-dihydro-2H-1,5-benzodioxepin-7-ylmethyl)-N-isobutylthiomorpholine-2-carboxamide: The mixture of (±)-N-(9-chloro-3,4-dihydro-2H-1,5-benzodioxepin-7-ylmethyl)-N-isobutyl thiomorpholine-2-carboxamide (40 mg), benzaladehyde (32 mg), glacial acetic acid (0.072 ml), and sodium triacetoxyborohydride (36 mg) in 5 ml dichloromethane was stirred overnight. After addition of aq. potassium carbonate (2M, 10 mL), the mixture was extracted with 5 ml of ethyl acetate twice. Organic layers were combined, washed with brine and concentrated. Flash chromatography on silica (10-30% ethyl acetate in hexane) gave the product as a resin: MS (m+1)= 489.4; 1H NMR (500 MHz, CDCl3) 0.95 (m, 6H), 2.00 (m, 1H), 2.25 (m, 1H), 2.30 (m, 1H), 2.45 (m, 1H), 2.65 (m, 1H), 2.75 (m, 1H), 3.00 (m, 1H), 3.10 (m, 1H), 3.20 (m, 1H), 3.35 (q, 1H), 3.6 (m, 2H), 3.80 (m, 1H), 3.95 (d, 1H), 4.15 (m, 1H), 4.30 (m, 4H), 4.85 (q, 1H), 6.7-7.0 (m, 2H), 7.2-7.4 (m, 5H).

Example 20

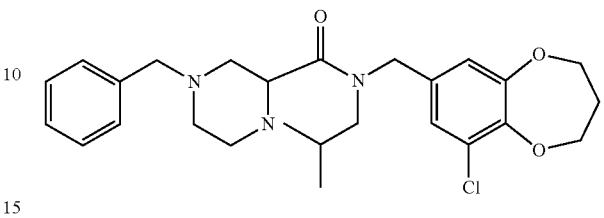

(±)-4-Benzyl-N-(9-chloro-3,4-dihydro-2H-1,5-benzodioxepin-7-ylmethyl)-N-isobutyl piperazine-2-carboxamide Step 1 (±)-4-Benzyl-N-(9-chloro-3,4-dihydro-2H-1,5-benzodioxepin-7-ylmethyl)-N-isobutyl piperazine-2-carboxamide: The mixture of N-(9-chloro-3,4-dihydro-2H-1,5-benzodioxepin-7-ylmethyl)-2-methylpropan-1-amine (84 mg), 4-benzyl-piperazine-1,2-dicarboxylic acid 1-tert-butyl ester (100 mg), 1-ethyl-3-(3-dimethylaminopropyl)carbodiimide hydrochloride (90 mg), and dimethyl aminopyridine (53 mg) in dichloromethane (8 ml) was stirred at room temperature overnight. After addition of water (8 ml) the reaction mixture was extracted with ethyl acetate (8 ml×3). The organic layers were combined, washed with saturated sodium bicarbonate, water and brine, dried over anhydrous sodium sulfate and concentrated under reduced pressure. The crude product was purified by column chromatography on silica (20% ethyl acetate in hexane) to give a resin: MS (m+1)= 572.4.

Step 2: (±)-4-benzyl-N-(9-chloro-3,4-dihydro-2H-1,5-benzodioxepin-7-ylmethyl)-N-isobutyl piperazine-2-carboxamide: The above product was dissolved in dichloromethane (2.5 ml) then treated with trifluoroacetic acid (2.5 ml). The mixture was stirred for one hour at room temperature. After the evaporation of volatiles under reduced pressure, the residue was dissolved in dichloromethane (5 ml), washed with saturated aq. sodium bicarbonate solution (6 ml). The aqueous was extracted with dichloromethane (5 ml×2). The organic layers were combined, dried with anhydrous sodium sulfate and concentrated under reduced pressure to yield colorless resin: MS (m+1)=472.4; 1H NMR (500 MHz, CDCl3) 0.90 (m, 6H), 1.95 (m, 1H), 2.00 (m, 1H), 2.05 (m, 1H), 2.15 (m, 1H), 2.25 (m, 1H), 2.80 (m, 1H), 2.90 (m, 1H), 2.95 (m, 1H), 3.00 (m, 1H), 3.10 (m, 1H), 3.20 (m, 1H), 3.50 (m, 1H), 3.60 (m, 1H), 3.85 (m, 2H), 4.30 (m, 4H), 4.45 (m, 1H), 4.55 (t, 1H), 6.7-6.9 (m, 2H), 7.2-7.4 (m, 5H).

Selected Experiments Using Contemplated Compounds

In vitro $Ca^{2+}$ Mobilization Assay

An aequorin-based luminescent assay for calcium mobilization was used to measure mobilization of intracellular $Ca^{2+}$ (Bullock et al., Mol Pharmacol 65, 582-588, 2004). Chinese hamster ovary (CHO) cells stably expressing photoprotein aequorin and recombinant PKR1 or PKR2 were tested by this method. Briefly, the cells were charged in Opti-MEM (Invitrogen) containing 8 μM of coelenterazine cp at 37° C. for 2 hours. Cells were detached by brief typsinization and maintained in Hank's Balanced Salt Solution (HBSS) plus 10 mM HEPES (pH7.5) and 0.1% BSA at about $5\times10^5$ cells/ml. Luminescence measurements were made using a Berthold luminometer.

All compounds were diluted in HBSS plus 10 mM HEPES (pH7.5) and 0.1% BSA. To test the agonist activity, 100 µl of cells were injected into the tubes with 20 µl of compounds. For antagonist assays, 80 µl cells were incubated in the tubes with 20 µl different concentrations of antagonists at room temperature for 20 minutes, and then 100 µl of recombinant PK2 were injected. The IC50 obtained from the assays were then converted to Ki values using the formula: $IC50/(1+[PK2]/EC50_{PK2})$.

In Vivo Delivery of PK2 Antagonist Improved Performance in the Glucose Tolerance Test (GTT)

The compound (3R)-1-Benzyl-N-(9-chloro-3,4-dihydro-2H-1,5-benzodioxepin-7-ylmethyl)-N-isobutyl pyrrolidine-3-carboxamide (3Cl-R-PLP) was dissolved in PEG-400 and then resuspended in water with 8% final concentration of PEG-400.8% PEG-400 in water without drug was used as vehicle. Mice were fed with regular chow. Drug or vehicle was gavaged to mice that were fasted overnight. Two hours later, glucose (2 g/kg of body weight) was injected i.p. and whole venous blood obtained from the tail vein at 0, 15, 30, 90 and 120 min after the injection was measured for glucose by using an automatic glucometer (one Touch, Lifescan, Daly, Calif.). Exemplary results are shown in FIG. 1 where Panel (A) shows that 3Cl-R-PLP at 4 mg/kg of body weight improved glucose clearance significantly in GTT. Panel (B) shows the dose-dependent effect of 3Cl-R-PLP on the performance in GTT at the concentrations of 0, 1, 4, 12, and 40 mg/kg of body weight.

Figure 2:
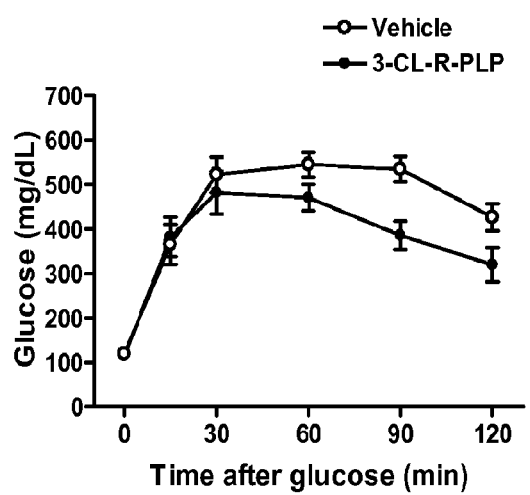
FIG. 2 is a graph depicting the in vivo effect of the exemplary compound on glucose clearance in a glucose tolerance test in a diet-induced hyperglycemia model.

In Vivo Delivery of PK2 Antagonist Improved Performance in GTT on Mice Fed with High-Fat Diet High fat diet was fed to mice for 8 weeks to induced diet-induced hyperglycemia. GTT test was carried out as described earlier. 3Cl-R-PLP (40 mg/kg body weight) significantly improved glucose clearance in GTT test in these diet-induced hyperglycemia models as can be seen from FIG. 2.

Figure 3:
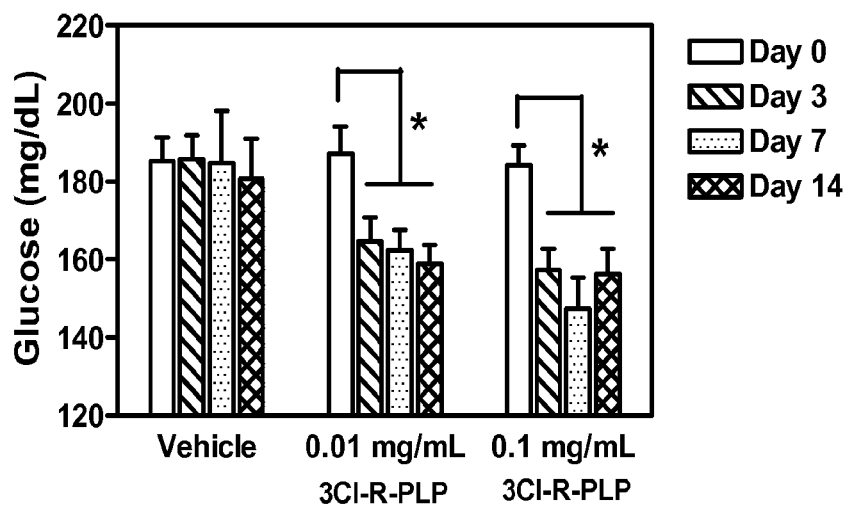
FIG. 3 is a graph depicting the in vivo effect of the exemplary compound on circulating glucose levels in a diet-induced hyperglycemia model.

Glucose-Lowering Effect of Chronic PK2 Antagonist in Diet-Induced Diabetes Models Diet-induced diabetes models were created by feeding with high-fat diet for 8 weeks. These mice developed glucose intolerance and hyperglycemia. 3Cl-R-PLP was dissolved in drinking water and given to mice for two weeks. Circulating glucose levels were measured 3, 7 and 14 days after 3Cl-R-PLP treatment. 3Cl-R-PLP at concentration of 0.1 and 0.01 mg/ml effectively decreased the glucose levels as can be taken from FIG. 3.

Glucose-Lowering Effect of Chronic PK2 Antagonist in db/db Models

Figure 4:
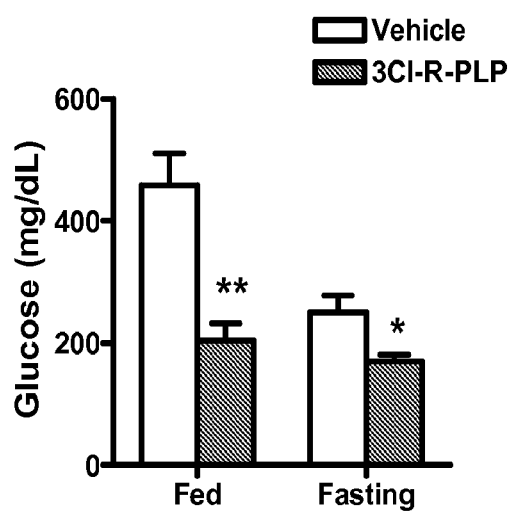
FIG. 4 is a graph depicting the in vivo effect of the exemplary compound on glucose levels under fed and fasting conditions in a diet-induced hyperglycemia model.

Db/db mice are commonly used as genetic models of type II diabetes. 10-week old db/db mice were treated with 3Cl-R-PLP (0.1 mg/mL in drinking water) or vehicle for 2 weeks. The figure below shows that 3Cl-R-PLP treatment significantly decreased glucose levels in db/db mice under both fed and fasting conditions as is shown in FIG. 4.

Figure 5:
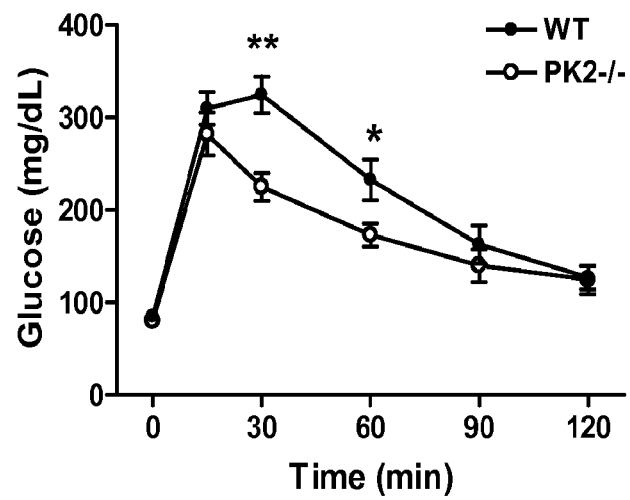
FIG. 5 is a graph depicting the in vivo effect of the exemplary compound on glucose clearance in a glucose tolerance test in PK2-deficient mice (PK2–/–) and wild type (WT) control mice.

PK2-Deficient Mice have Enhanced Glucose Clearance Abilities and are Resistant to Diet-Induced Hyperglycemia GTT test was carried out in PK2-deficient mice (PK2–/–) and wild type (WT) control mice that were fed with regular chows. As shown in the figure below, PK2-deficient mice exhibited enhanced ability to clear glucose delivered by i.p., compared to WT controls. Results are shown in FIG. 5.

Figure 6:
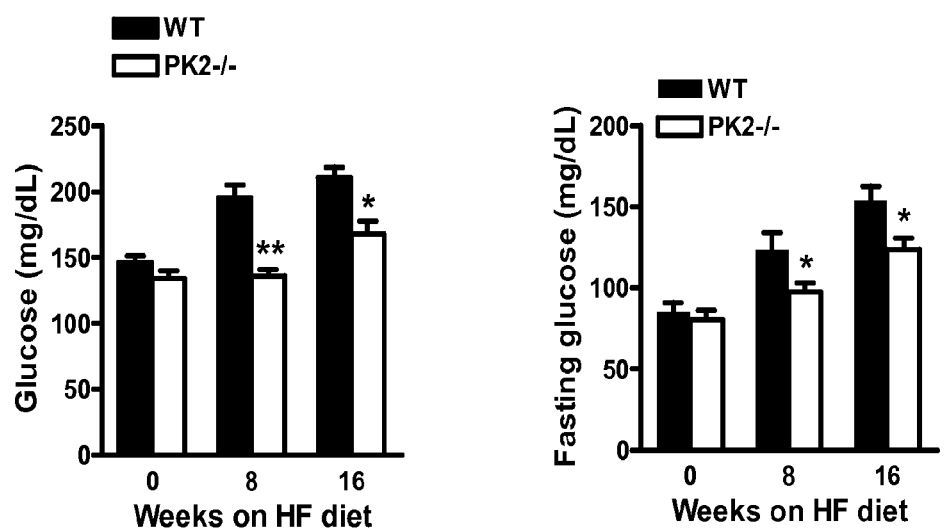
FIG. 6 is a graph depicting the in vivo effect of the exemplary compound on the sensitivity to diet-induced hyperglycemia by feeding with high fat (HF) diets in PK2-deficient mice (PK2–/–) and wild type (WT) control mice under fed and fasting conditions.

PK2-deficient mice and wild type control mice were then tested for their sensitivities to diet-induced hyperglycemia by feeding with high fat (HF) diets for 8 or 16 weeks. In contrast to wild type mice, PK2-deficient mice exhibited significant resistance to diet-induced hyperglycemia as is readily evident from FIG. 6.

Figure 7:
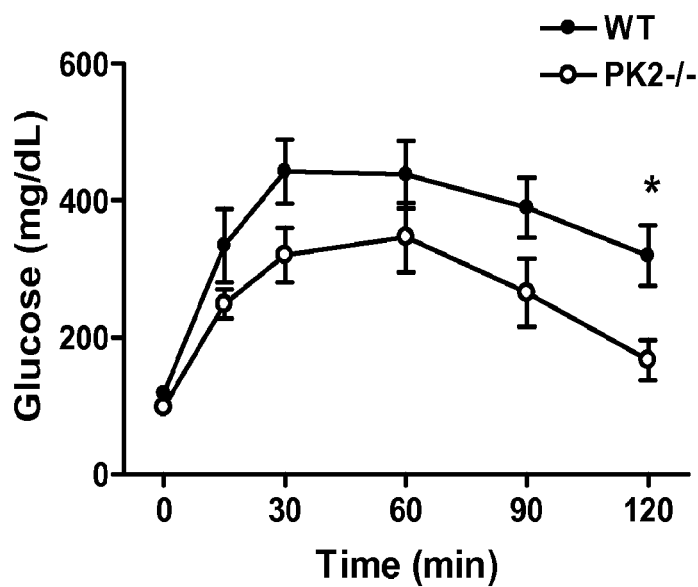
FIG. 7 is a graph depicting the in vivo effect of the exemplary compound on glucose clearance in a glucose tolerance test in PK2-deficient mice (PK2–/–) and wild type (WT) control mice previously maintained on a high fat diet.

GTT tests were also carried out in PK2-deficient mice and wild type control mice that were fed for high fat diet for 8 weeks. As with feeding with regular chows, PK2-deficient mice possessed enhanced capabilities to clear glucose delivered by i.p. Typical results are shown in FIG. 7.

PK2 Administration Reduced Glucose Clearance and Circulating Insulin Level

Figure 8:
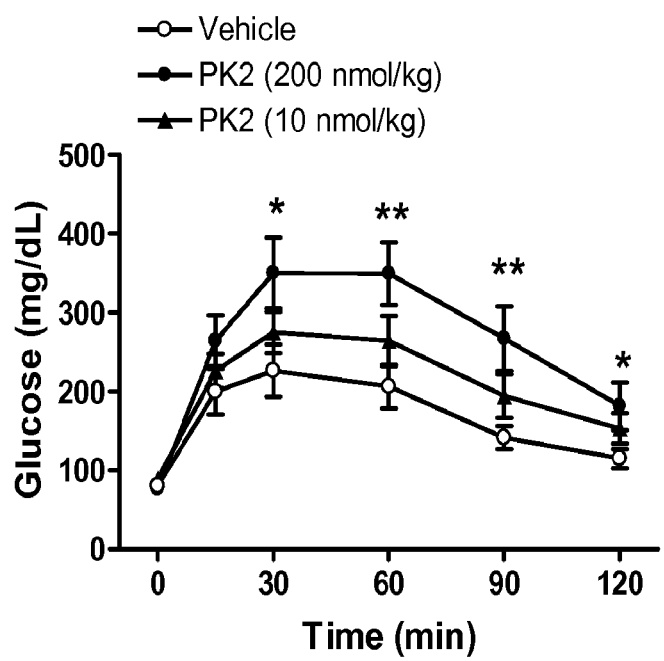
FIG. 8 is a graph depicting the in vivo effect of PK2 administration on glucose clearance in a glucose tolerance test in PK2-deficient mice (PK2–/–) and wild type (WT) control mice.

The inventors next tested the effect of PK2 administration on the performance of GTT test in wild type mice. As shown in the figure below, PK2 at doses of 10 nmol/kg and 200 nmol/kg significantly reduced the rate of glucose clearance as can be seen from FIG. 8. This is consistent with observations that PK2-deficient mice have enhanced glucose clearance abilities.

Figure 9:
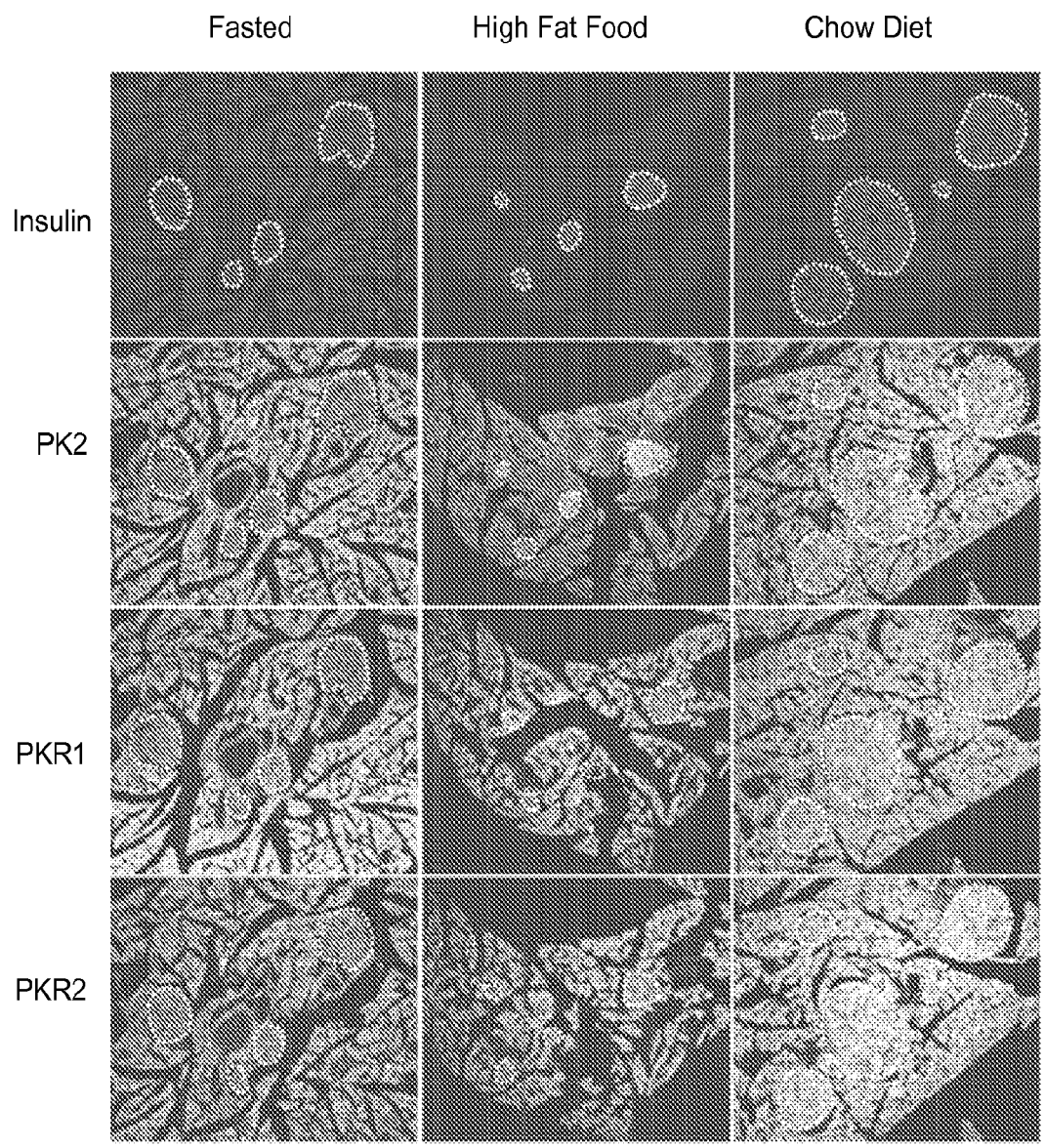
FIG. 9 is a collection of photomicrographs of pancreas sections immuno-stained with antibodies against insulin, PKR1, and PKR2 from fasted mice, mice fed with high fat diet, and mice fed with chow diet.
Figure 10:
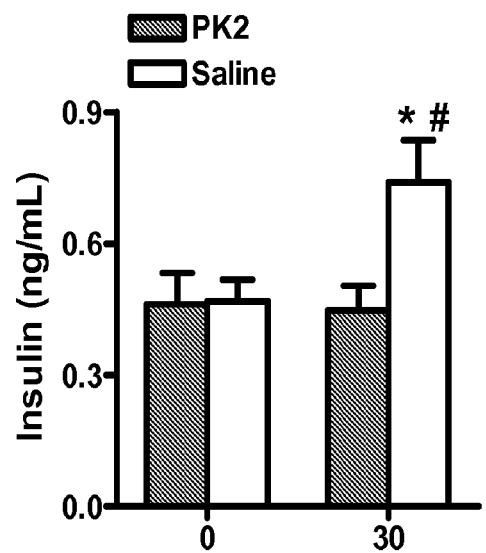
FIG. 10 is a graph depicting the in vivo effect of PK2 administration on insulin secretion in PK2-deficient mice (PK2–/–) and wild type (WT) control mice.
Figure 11:
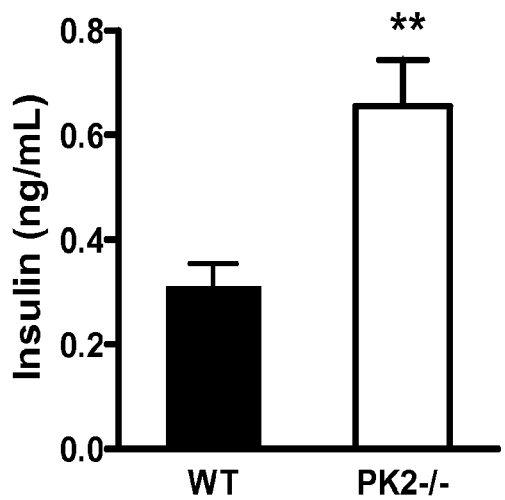
FIG. 11 is a graph depicting the in vivo effect of PK2 administration on insulin secretion in PK2-deficient mice.

The above observations demonstrated a critical role of PK2 signaling in glucose homeostasis. To understand whether insulin is directly involved, the inventors examined whether PK2 and/or its two cognate receptors, PKR1 and PKR2, are expressed in pancreas beta cells. In situ hybridization with mouse pancreas sections indicated that PK2, along with both PKR1 and PKR2 are expressed in pancreas islets (circled) that were also insulin immuno-positive as is shown in the photomicrographs of FIG. 9. This expression pattern suggested that PK2 signaling may directly regulate the insulin secretion from pancreas beta cells. Delivery of glucose by i.p. significantly increased circulating insulin levels (30 min). The inventors tested whether this glucose-induced insulin secretion was inhibited by PK2. As can be seen from FIG. 10, administration of PK2 significantly inhibited glucose-induced elevation of insulin in circulation. Consistent with the inhibitory effect of PK2 on insulin secretion, PK2-deficient mice have increased circulating insulin level. It is likely that at least some of glucose-lowering effects of PK2 antagonists were due to their abilities to increase insulin secretion as depicted in FIG. 11.

Figure 12:
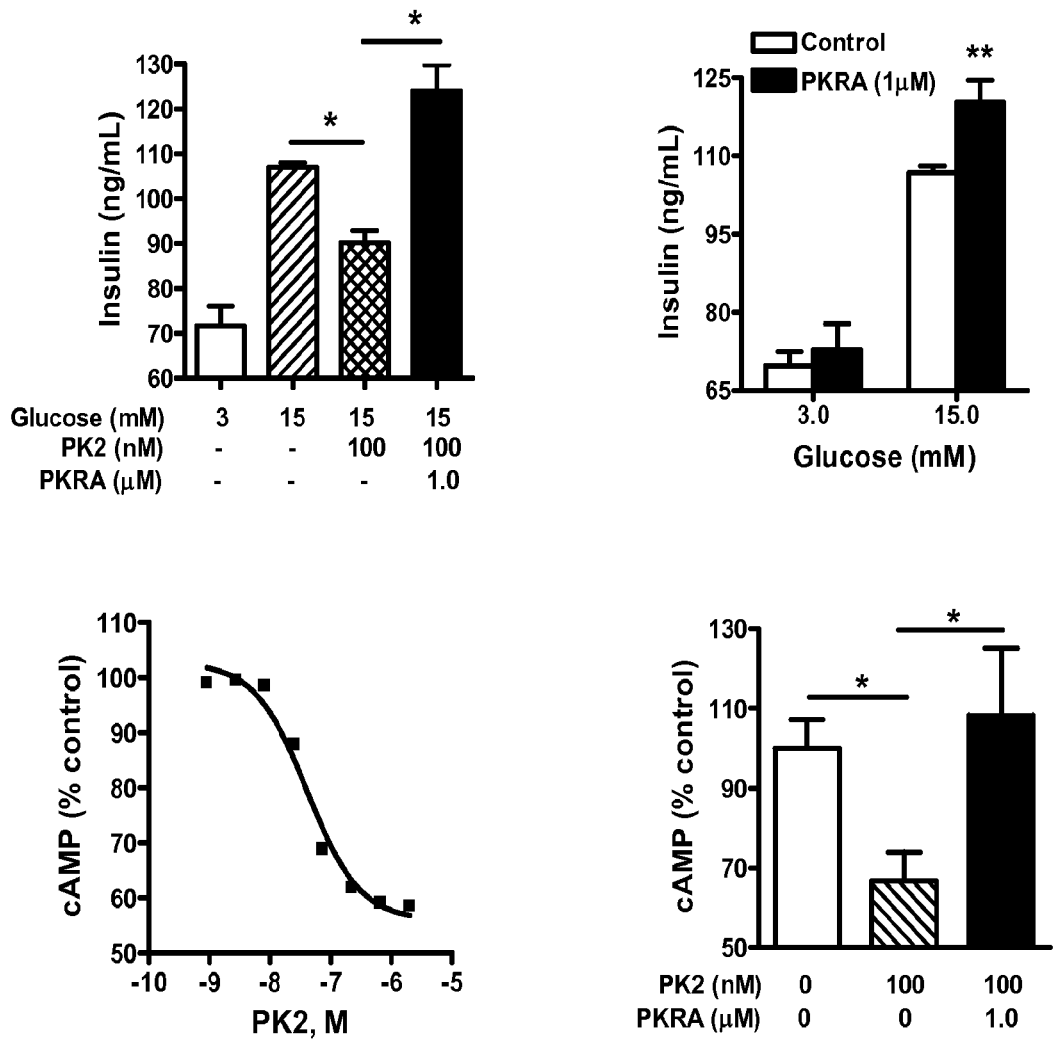
FIG. 12 is a graph depicting various in vitro effects of PK2 and contemplated compounds on insulin secretion (Panels A and B) and cAMP levels (Panels C and D) in MIN6 cells.

PK2 Signaling Inhibits Insulin Secretion Via Modulating Camp Level in the β-Cell Like MIN6 Cells To investigate the direct effects of PK2 on the insulin secretion, the inventors performed a glucose-stimulated insulin secretion on β-cell like MIN6 cells. As shown in Panel (A) of FIG. 12, addition of PK2 significantly suppressed the insulin secretion induced by 15 mM of glucose in MIN6 cells. PK2 receptor antagonist 4Ind-3Cl-R-BMA (PKRA) at 1 µM completely reversed the inhibitory effect of PK2 on glucose-stimulated insulin secretion (Panel (A)). In fact, the insulin levels from the cells treated with a combination of 4Ind-3Cl-R-BMA and PK2 were even higher than those stimulated with 15 mM of glucose only, suggesting that 4Ind-3Cl-R-BMA also blocked the insulinostatic effect of endogenous PK2. To specifically test the effects of endogenous PK2, the inventors treated MIN6 cells with 4Ind-3Cl-R-BMA along with low and high concentrations of glucose. As shown in Panel B of FIG. 12, 4Ind-3Cl-R-BMA alone enhanced the high glucose-stimulated insulin secretion but not basal insulin secretion in MIN6 cells under low glucose, implying that the endogenous PK2 may be released by high glucose from β-cells and then functioned locally as a paracrine or autocrine factor. As PK2 receptors have been reported coupling to Gi or Gq proteins, the inventors examined the possible signaling transduction of PK2 receptor in MIN6 cells. Whereas PK2 didn't elicit cytosolic calcium mobilization in MIN6 cells, it significantly inhibited forskolin-induced cAMP levels in MIN6 cells (Panel C of FIG. 12), which was antagonized by the PK2 receptor antagonist 4Ind-3Cl-R-BMA (Panel D of FIG. 12). These results indicated that PK2 signaling was coupled to Gi pathway in n-cells which may mediate its insulinostatic effect.

Exemplary Compounds and Inhibition Data for PKR2 and PKR12

The following compounds were prepared using the above synthetic routes and protocols by varying the starting materials, reagents or conditions used. The requisite reagents were either commercially available, described in the literature, or readily synthesized by one skilled in the art. The potency of these compounds in antagonizing PK2-stimulated calcium mobilization were tested in Chinese hamster ovary (CHO) cells that stably express recombinant PKR1 or PKR2.

| Structure | Compound Name | Mass Ion (M + 1) | Ki for PKR2 (nM) | Ki for PKR1 (nM) |
|---|---|---|---|---|
| 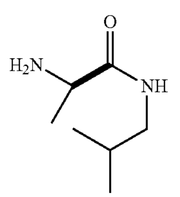 | (+)-(2S)-2-Amino-N-isobutylpropanamide | 145.1 | | 9840 |
| 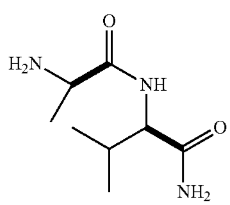 | N-[(2S)-2-Aminopropanoyl]-(2S)-valylamide | 188.2 | | 183 |
| 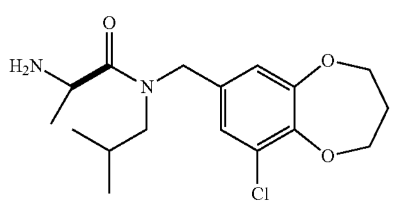 | (+)-(2S)-2-Amino-N-(9-chloro-3,4-dihydro-2H-1,5-benzodioxepin-7-ylmethyl)-N-isobutylpropanamide | 341.1 | | 427 |
| 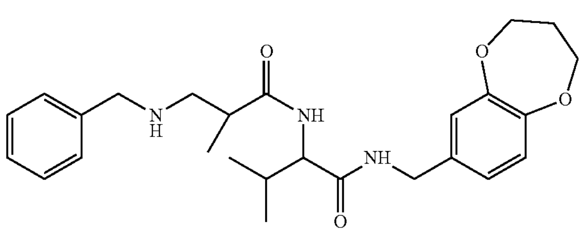 [SMILES: CC(CNCc1ccccc1)C(=O)NC(C(=O)NCc1ccc2c(c1)OCCCO2)C(C)C] | N-[(±)-2-Methyl-3-benzylaminopropanoyl]-(±)-valyl-(3,4-dihydro-2H-1,5-benzodioxepin-7-ylmethyl)amide | 454.3 | | 1422 |
| 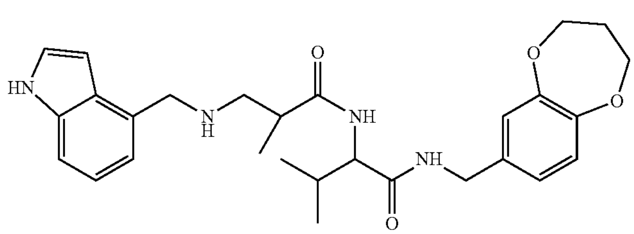 [SMILES: CC(CNCc1cccc2[nH]ccc12)C(=O)NC(C(=O)NCc1ccc2c(c1)OCCCO2)C(C)C] | N-[(±)-2-Methyl-3-(indol-4ylmethyl)aminopropanoyl]-(±)-valyl-(3,4-dihydro-2H-1,5-benzodioxepin-7-ylmethyl)amide | 493.3 | | 248 |

-continued

| Structure | Compound Name | Mass Ion (M + 1) | Ki for PKR2 (nM) | Ki for PKR1 (nM) |
|---|---|---|---|---|
| 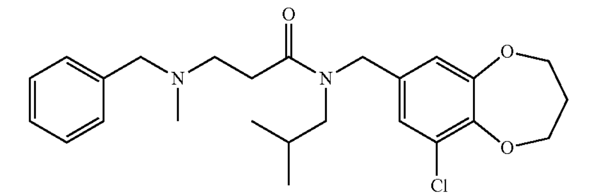 [SMILES: CC(C)CN(Cc1cc(Cl)c2c(c1)OCCCO2)C(=O)CCN(C)Cc1ccccc1] | 3-(Benzyl(methyl)amino)-N-(9-chloro-3,4-dihydro-2H-1,5-benzodioxepin-7-ylmethyl)-N-isobutylpropanamide | 431.3 | 272 | |
| 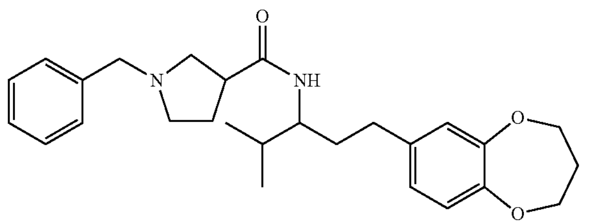 [SMILES: CC(C)C(CCc1ccc2c(c1)OCCCO2)NC(=O)C1CCN(Cc2ccccc2)C1] | (±)-1-Benzyl-N-(3,4-dihydro-2H-1,5-benzodioxepin-7-yl-α-isopropyl-propyl)-pyrrolidine-3-carboxamide | 437.2 | 2100 | |
| 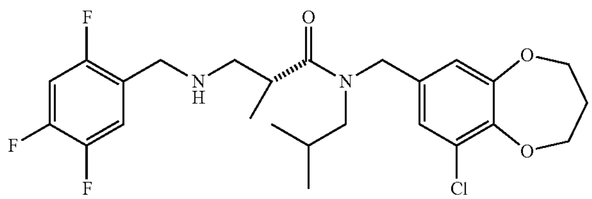 | (−)-(2R)-2-Methyl-3-((2,4,5-trifluoro)benzylamino)-N-(9-chloro-3,4-dihydro-2H-1,5-benzodioxepin-7-ylmethyl)-N-isobutylpropanamide | 499.3 | 13.3 | 258 |
| 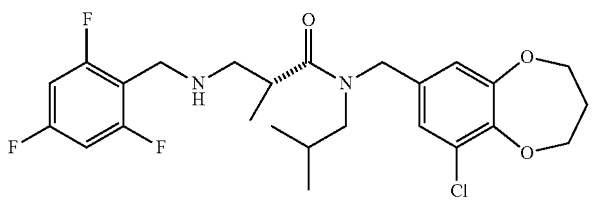 | (−)-(2R)-2-Methyl-3-((2,4,6-trifluoro)benzylamino)-N-(9-chloro-3,4-dihydro-2H-1,5-benzodioxepin-7-ylmethyl)-N-isobutylpropanamide | 499.3 | 9.02 | 138 |
| 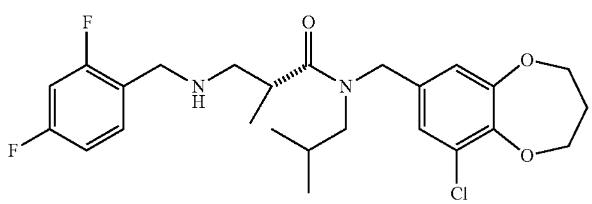 | (−)-(2R)-2-Methyl-3-((2,4-difluoro)benzylamino)-N-(9-chloro-3,4-dihydro-2H-1,5-benzodioxepin-7-ylmethyl)-N-isobutylpropanamide | 481.3 | 6.2<br>8.5<br>12.8 | 123 |
| 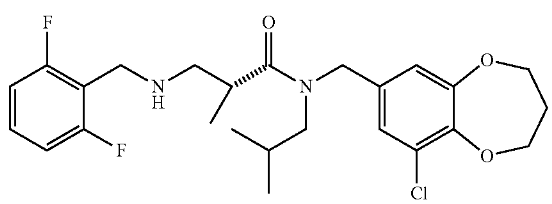 | (−)-(2R)-2-Methyl-3-((2,6-difluoro)benzylamino)-N-(9-chloro-3,4-dihydro-2H-1,5-benzodioxepin-7-ylmethyl)-N-isobutylpropanamide | 481.3 | 9.84<br>8.58 | 121 |
| 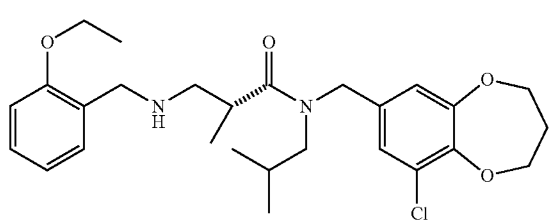 | (−)-(2R)-2-Methyl-3-((2-ethoxy)benzylamino)-N-(9-chloro-3,4-dihydro-2H-1,5-benzodioxepin-7-ylmethyl)-N-isobutyl propanamide | 489.2 | 7.18 | |

-continued

| Structure | Compound Name | Mass Ion (M + 1) | Ki for PKR2 (nM) | Ki for PKR1 (nM) |
|---|---|---|---|---|
| 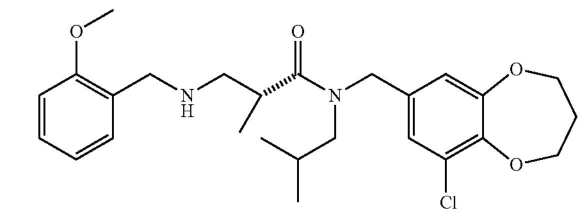 | (−)-(2R)-2-Methyl-3-((2-methoxy)benzylamino)-N-(9-chloro-3,4-dihydro-2H-1,5-benzodioxepin-7-ylmethyl)-N-isobutylpropanamide | 475.2 | 1.35 | 8.76 |
| 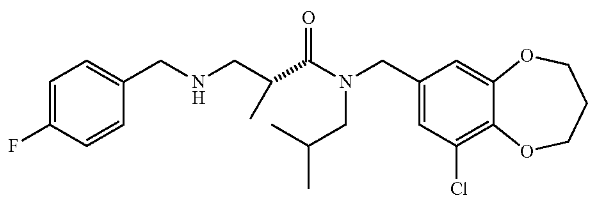 | (−)-(2R)-2-Methyl-3-((4-fluoro)benzylamino)-N-(9-chloro-3,4-dihydro-2H-1,5-benzodioxepin-7-ylmethyl)-N-isobutylpropanamide | 463.3 | 1.62 5.36 | |
| 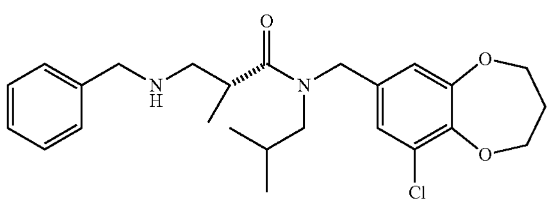 | (−)-(2R)-2-Methyl-3-(benzylamino)-N-(9-chloro-3,4-dihydro-2H-1,5-benzodioxepin-7-ylmethyl)-N-isobutylpropanamide | 445.2 | 4.92 1.40 | 32.4 73.2 |
| 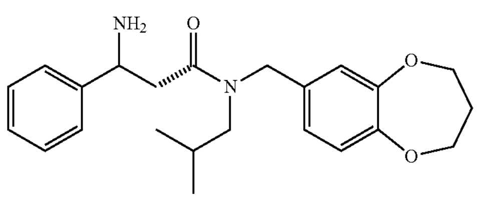 | (−)-(2R)-N-(3,4-dihydro-2H-1,5-benzodioxepin-7-ylmethyl)-N-isobutyl-3-amino-3-phenylpropanamide | 382.3 | 1162 | |
| 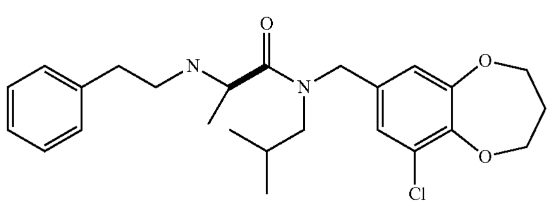 | (−)-(2S)-N-(9-chloro-3,4-dihydro-2H-1,5-benzodioxepin-7-ylmethyl)-N-isobutyl-2-(phenethylamino)propanamide | 445.2 | 934 | |
| 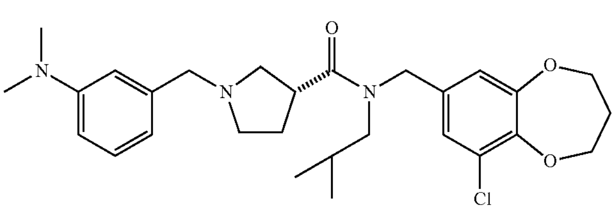 | (−)-(3R)-1-((3-Dimethylamino)benzyl)-N-(9-chloro-3,4-dihydro-2H-1,5-benzodioxepin-7-ylmethyl)-N-isobutylpyrrolidine-3-carboxamide | 500.5 | 38.4 | 71.8 |
| 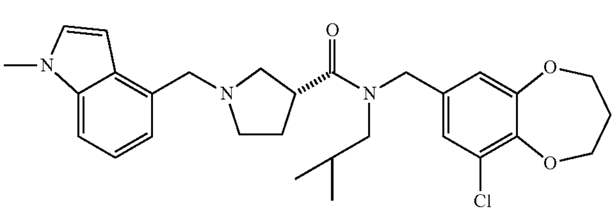 | (−)-(3R)-1-(1-Methyl-indol-4-ylmethyl)-N-(9-chloro-3,4-dihydro-2H-1,5-benzodioxepin-7-ylmethyl)-N-isobutylpyrrolidine-3-carboxamide | 510.2 | 3.68 | 3.64 6.50 |

-continued

| Structure | Compound Name | Mass Ion (M + 1) | Ki for PKR2 (nM) | Ki for PKR1 (nM) |
|---|---|---|---|---|
| 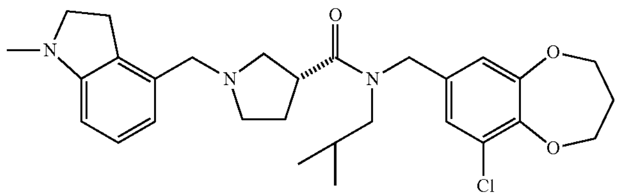 | (−)-(3R)-1-(1-Methyl-indol-4-ylmethyl)-N-(9-chloro-3,4-dihydro-2H-1,5-benzodioxepin-7-ylmethyl)-N-isobutylpyrrolidine-3-carboxamide | 512.3 | 2.92 | 8.82 |
| 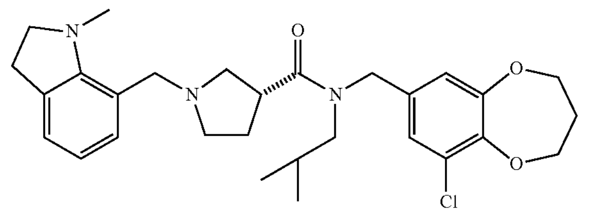 | (−)-(3R)-1-(1-Methyl-indol-7-ylmethyl)-N-(9-chloro-3,4-dihydro-2H-1,5-benzodioxepin-7-ylmethyl)-N-isobutylpyrrolidine-3-carboxamide | 512.3 | 20.0 | 54.0 |
| 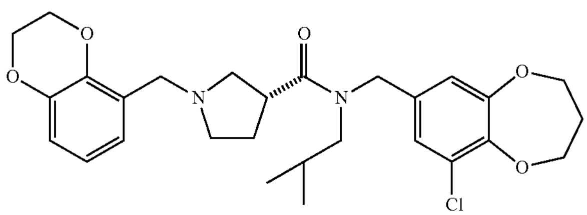 | (−)-(3R)-1-(2,3-Dihydro-1,4-benzodioxin-5-ylmethyl)-N-(9-chloro-3,4-dihydro-2H-1,5-benzodioxepin-7-ylmethyl)-N-isobutylpyrrolidine-3-carboxamide | 515.2 | 6.88 5.68 | 12.2 |
| | (−)-(3R)-1-(2,3-Dihydro-1-benzofuran-7-ylmethyl)-N-(9-chloro-3,4-dihydro-2H-1,5-benzodioxepin-7-ylmethyl)-N-isobutylpyrrolidine-3-carboxamide | 501.3 | 5.16 | 61.2 |
| | (−)-(3R)-1-(2,3-Dihydro-1-benzofuran-7-ylmethyl)-N-(9-chloro-3,4-dihydro-2H-1,5-benzodioxepin-7-ylmethyl)-N-isobutylpyrrolidine-3-carboxamide | 499.3 | 3.72 | 9.42 |
| 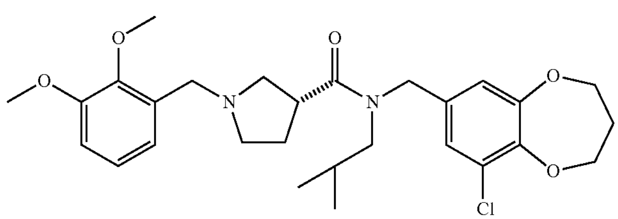 | (−)-(3R)-1-(2,3-Dimethoxybenzyl)-N-(9-chloro-3,4-dihydro-2H-1,5-benzodioxepin-7-ylmethyl)-N-isobutylpyrrolidine-3-carboxamide | 517.3 | 43.4 | 173 |
| 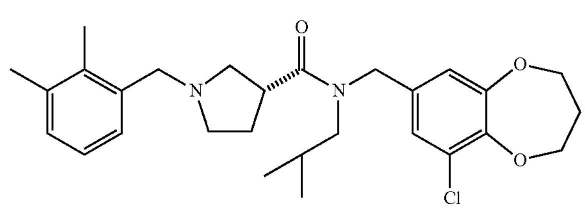 | (−)-(3R)-1-(2,3-Dimethylbenzyl)-N-(9-chloro-3,4-dihydro-2H-1,5-benzodioxepin-7-ylmethyl)-N-isobutylpyrrolidine-3-carboxamide | 485.4 | 1.89 | 11.6 |

-continued

| Structure | Compound Name | Mass Ion (M + 1) | Ki for PKR2 (nM) | Ki for PKR1 (nM) |
|---|---|---|---|---|
| 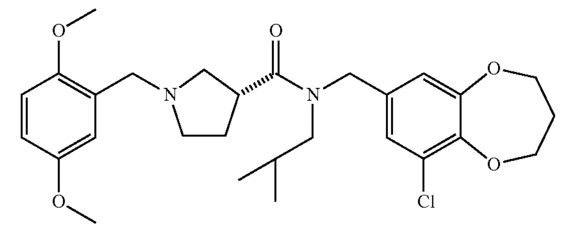 | (−)-(3R)-1-(2,5-Dimethoxybenzyl)-N-(9-chloro-3,4-dihydro-2H-1,5-benzodioxepin-7-ylmethyl)-N-isobutylpyrrolidine-3-carboxamide | 517.3 | 7.32 | 47.8 |
| | (−)-(3R)-1-(2-Aminobenzyl)-N-(9-chloro-3,4-dihydro-2H-1,5-benzodioxepin-7-ylmethyl)-N-isobutylpyrrolidine-3-carboxamide | 472.4 | 31.5 38.7 | |
| | (−)-(3R)-1-(2-Aminobenzyl)-N-(9-chloro-3,4-dihydro-2H-1,5-benzodioxepin-7-ylmethyl)-N-isobutylpyrrolidine-3-carboxamide | 486.4 | 65.1 | |
| 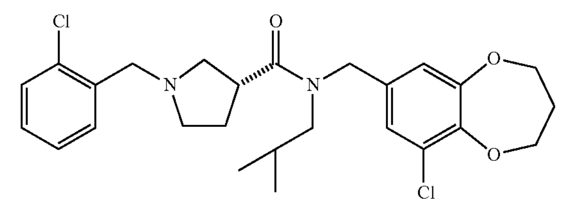 | (−)-(3R)-1-(2-Chlorobenzyl)-N-(9-chloro-3,4-dihydro-2H-1,5-benzodioxepin-7-ylmethyl)-N-isobutylpyrrolidine-3-carboxamide | 491.0 | 38.9 | |
| 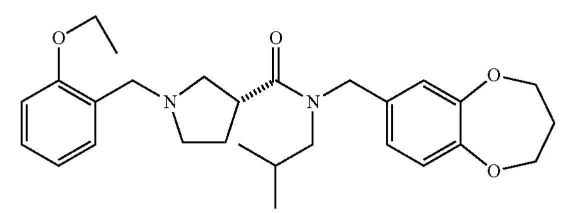 | (−)-(3R)-1-(2-Ethoxybenzyl)-N-(3,4-dihydro-2H-1,5-benzodioxepin-7-ylmethyl)-N-isobutylpyrrolidine-3-carboxamide | 467.3 | 18.7 | |
| 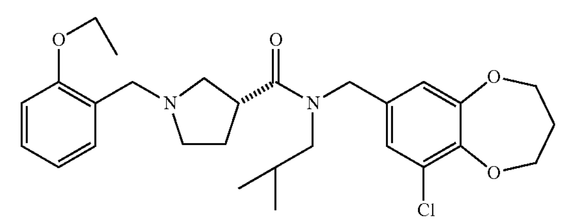 | (−)-(3R)-1-(2-Ethoxybenzyl)-N-(9-chloro-3,4-dihydro-2H-1,5-benzodioxepin-7-ylmethyl)-N-isobutylpyrrolidine-3-carboxamide | 501.5 | 8.77 | |
| 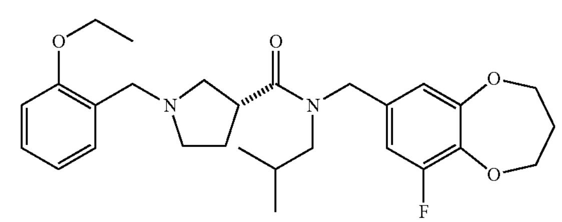 | (−)-(3R)-1-(2-Ethoxybenzyl)-N-(9-fluoro-3,4-dihydro-2H-1,5-benzodioxepin-7-ylmethyl)-N-isobutylpyrrolidine-3-carboxamide | 485.4 | 4.0 | |

-continued

| Structure | Compound Name | Mass Ion (M + 1) | Ki for PKR2 (nM) | Ki for PKR1 (nM) |
|---|---|---|---|---|
| 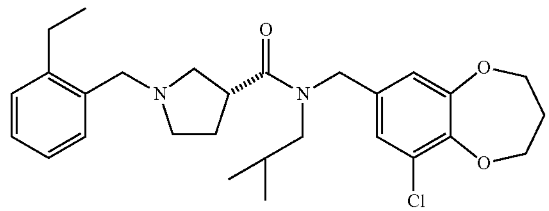 | (−)-(3R)-1-(2-Ethylbenzyl)-N-(9-chloro-3,4-dihydro-2H-1,5-benzodioxepin-7-ylmethyl)-N-isobutylpyrrolidine-3-carboxamide | 485.2 | 13.7 | |
| 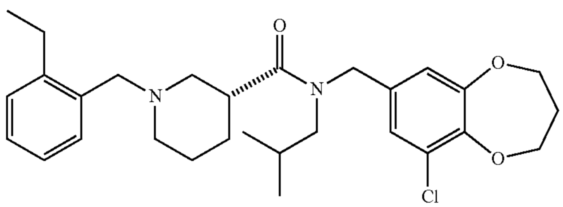 [SMILES: CCc1ccccc1CN1CCC[C@@H](C(=O)N(Cc2cc(Cl)c3c(c2)OCCCO3)CC(C)C)C1] | (−)-(3R)-1-(2-Ethylbenzyl)-N-(9-chloro-3,4-dihydro-2H-1,5-benzodioxepin-7-ylmethyl)-N-isobutylpiperidine-3-carboxamide | 499.5 | 92.4 | |
| 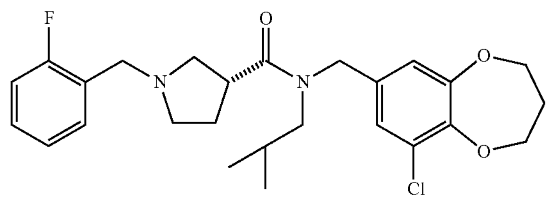 | (−)-(3R)-1-(2-Flurobenzyl)-N-(9-chloro-3,4-dihydro-2H-1,5-benzodioxepin-7-ylmethyl)-N-isobutylpyrrolidine-3-carboxamide | 475.7 | 12.2 | 37.2 |
| 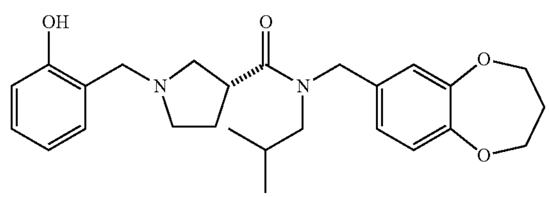 [SMILES: CC(C)CN(Cc1ccc2c(c1)OCCCO2)C(=O)[C@@H]1CCN(Cc2ccccc2O)C1] | (−)-(3R)-1-(2-Hydroxybenzyl)-N-(3,4-dihydro-2H-1,5-benzodioxepin-7-ylmethyl)-N-isobutylpyrrolidine-3-carboxamide | 439.4 | 60.5 | |
| 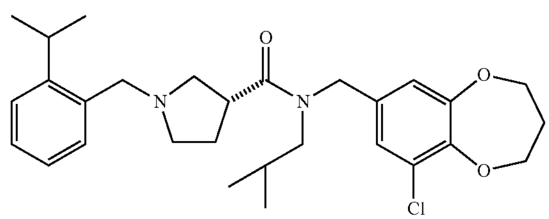 [SMILES: CC(C)CN(Cc1cc(Cl)c2c(c1)OCCCO2)C(=O)[C@@H]1CCN(Cc2ccccc2C(C)C)C1] | (−)-(3R)-1-(2-Isopropylbenzyl)-N-(9-chloro-3,4-dihydro-2H-1,5-benzodioxepin-7-ylmethyl)-N-isobutylpyrrolidine-3-carboxamide | 499.5 | 24.4 | 68.8 |
| 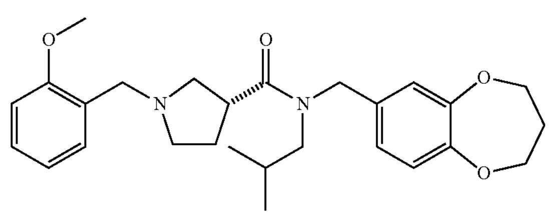 [SMILES: COc1ccccc1CN1CC[C@@H](C(=O)N(Cc2ccc3c(c2)OCCCO3)CC(C)C)C1] | (−)-(3R)-1-(2-Methoxybenzyl)-N-(3,4-dihydro-2H-1,5-benzodioxepin-7-ylmethyl)-N-isobutylpyrrolidine-3-carboxamide | 453.3 | 3.18 3.36 2.67 | 12.8 |
| 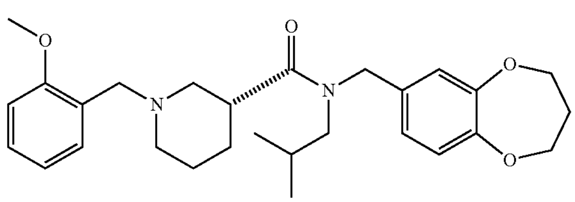 | (−)-(3R)-1-(2-Methoxybenzyl)-N-(3,4-dihydro-2H-1,5-benzodioxepin-7-ylmethyl)-N-isobutylpiperidine-3-carboxamide | 467.4 | 9.31 | 38.6 |

-continued

| Structure | Compound Name | Mass Ion (M + 1) | Ki for PKR2 (nM) | Ki for PKR1 (nM) |
|---|---|---|---|---|
| 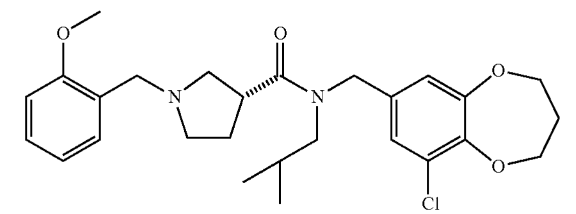 [SMILES: COc1ccccc1CN1CC[C@@H](C(=O)N(Cc2cc(Cl)c3c(c2)OCCCO3)CC(C)C)C1] | (−)-(3R)-1-(2-Methoxybenzyl)-N-(9-chloro-3,4-dihydro-2H-1,5-benzodioxepin-7-ylmethyl)-N-isobutylpyrrolidine-3-carboxamide | 487.2 | .68 | 10.9 8.8 |
| 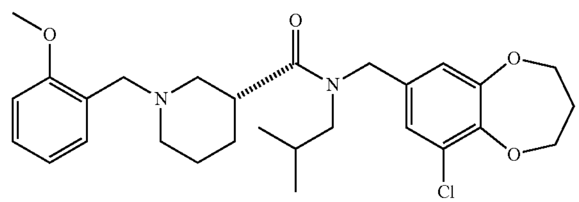 | (−)-(3R)-1-(2-Methoxybenzyl)-N-(9-chloro-3,4-dihydro-2H-1,5-benzodioxepin-7-ylmethyl)-N-isobutylpiperidine-3-carboxamide | 501.4 | 6.19 | 38.8 |
| 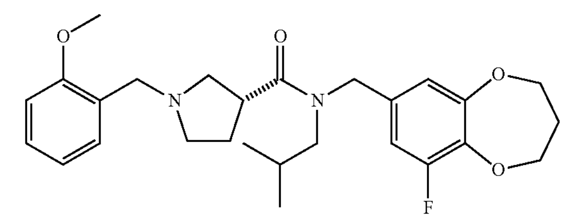 [SMILES: COc1ccccc1CN1CC[C@@H](C(=O)N(Cc2cc(F)c3c(c2)OCCCO3)CC(C)C)C1] | (−)-(3R)-1-(2-Methoxybenzyl)-N-(9-fluoro-3,4-dihydro-2H-1,5-benzodioxepin-7-ylmethyl)-N-isobutylpyrrolidine-3-carboxamide | 471.4 | 0.81 1.70 | 10.4 |
| 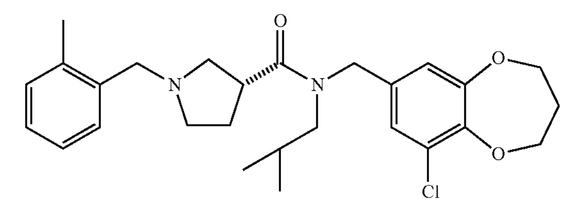 [SMILES: Cc1ccccc1CN1CC[C@@H](C(=O)N(Cc2cc(Cl)c3c(c2)OCCCO3)CC(C)C)C1] | (−)-(3R)-1-(2-Methylbenzyl)-N-(9-chloro-3,4-dihydro-2H-1,5-benzodioxepin-7-ylmethyl)-N-isobutylpyrrolidine-3-carboxamide | 471.4 | 11.9 | |
| 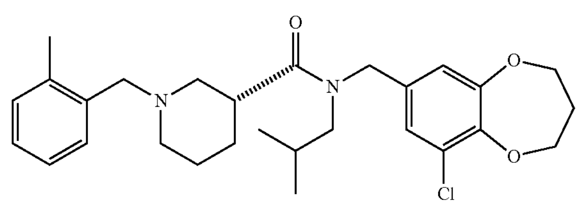 | (−)-(3R)-1-(2-Methylbenzyl)-N-(9-chloro-3,4-dihydro-2H-1,5-benzodioxepin-7-ylmethyl)-N-isobutylpiperidine-3-carboxamide | 485.5 | 27.2 | |
| 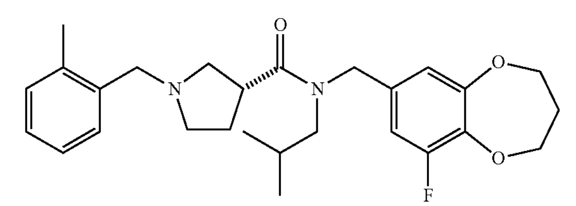 [SMILES: Cc1ccccc1CN1CC[C@@H](C(=O)N(Cc2cc(F)c3c(c2)OCCCO3)CC(C)C)C1] | (−)-(3R)-1-(2-Methylbenzyl)-N-(9-fluoro-3,4-dihydro-2H-1,5-benzodioxepin-7-ylmethyl)-N-isobutylpyrrolidine-3-carboxamide | 455.4 | 9.7 | 17.5 46.4 31.2 |
| 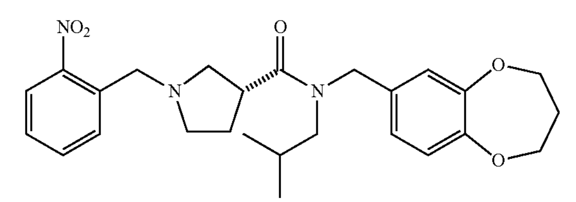 [SMILES: CC(C)CN(Cc1ccc2c(c1)OCCCO2)C(=O)[C@@H]1CCN(Cc2ccccc2[N+](=O)[O-])C1] | (−)-(3R)-1-(2-Nitrobenzyl)-N-(3,4-dihydro-2H-1,5-benzodioxepin-7-ylmethyl)-N-isobutylpyrrolidine-3-carboxamide | 468.3 | 297 | |

-continued

| Structure | Compound Name | Mass Ion (M + 1) | Ki for PKR2 (nM) | Ki for PKR1 (nM) |
|---|---|---|---|---|
| 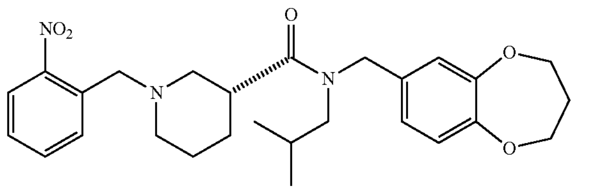 | (−)-(3R)-1-(2-Nitrobenzyl)-N-(3,4-dihydro-2H-1,5-benzodioxepin-7-ylmethyl)-N-isobutylpiperidine-3-carboxamide | 482.4 | 251 | |
| 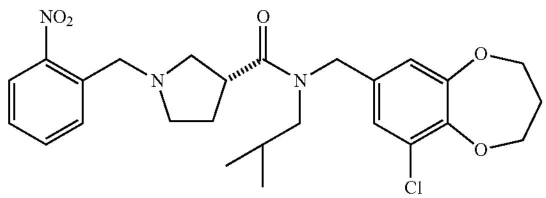 | (−)-(3R)-1-(2-Nitrobenzyl)-N-(9-chloro-3,4-dihydro-2H-1,5-benzodioxepin-7-ylmethyl)-N-isobutylpyrrolidine-3-carboxamide | 502.5 | 85.7 | |
| 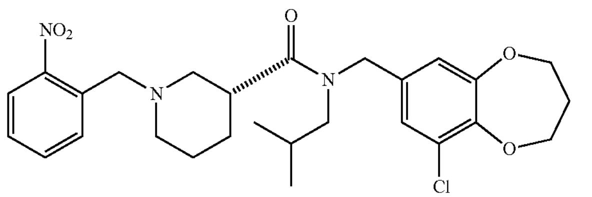 | (−)-(3R)-1-(2-Nitrobenzyl)-N-(9-chloro-3,4-dihydro-2H-1,5-benzodioxepin-7-ylmethyl)-N-isobutylpiperidine-3-carboxamide | 516.4 | 251 | |
| 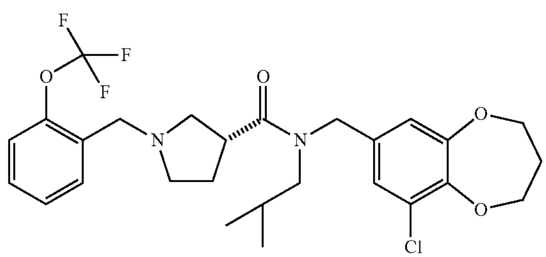 [SMILES: CC(C)CN(Cc1cc(Cl)c2c(c1)OCCCO2)C(=O)[C@@H]1CCN(Cc2ccccc2OC(F)(F)F)C1] | (−)-(3R)-1-(2-Trifluoromethoxybenzyl)-N-(9-chloro-3,4-dihydro-2H-1,5-benzodioxepin-7-ylmethyl)-N-isobutylpyrrolidine-3-carboxamide | 541.4 | 40.4 | |
| 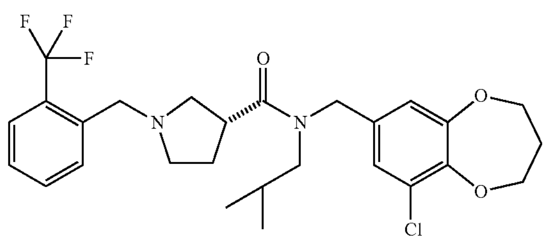 [SMILES: CC(C)CN(Cc1cc(Cl)c2c(c1)OCCCO2)C(=O)[C@@H]1CCN(Cc2ccccc2C(F)(F)F)C1] | (−)-(3R)-1-(2-Trifluoromethylbenzyl)-N-(9-chloro-3,4-dihydro-2H-1,5-benzodioxepin-7-ylmethyl)-N-isobutylpyrrolidine-3-carboxamide | 525.5 | 51.8 | |
| 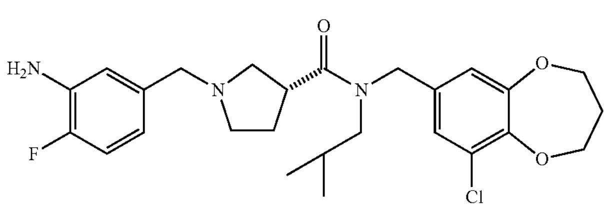 | (−)-(3R)-1-(3-Amino-4-fluorobenzyl)-N-(9-chloro-3,4-dihydro-2H-1,5-benzodioxepin-7-ylmethyl)-N-isobutylpyrrolidine-3-carboxamide | 490.6 | 3.57 | 24.0 |
| 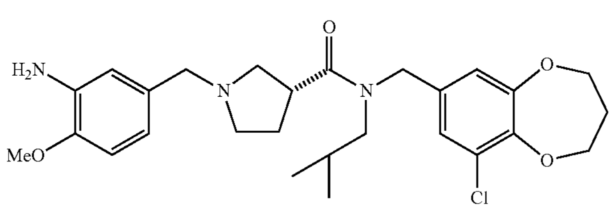 | (−)-(3R)-1-(3-Amino-4-methoxybenzyl)-N-(9-chloro-3,4-dihydro-2H-1,5-benzodioxepin-7-ylmethyl)-N-isobutylpyrrolidine-3-carboxamide | 502.6 | 3.68 | 61.0 |

-continued

| Structure | Compound Name | Mass Ion (M + 1) | Ki for PKR2 (nM) | Ki for PKR1 (nM) |
| --- | --- | --- | --- | --- |
| 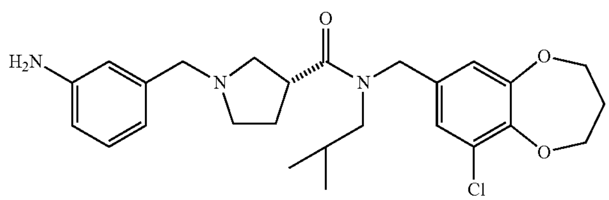 | (−)-(3R)-1-(3-aminobenzyl)-N-(9-chloro-3,4-dihydro-2H-1,5-benzodioxepin-7-ylmethyl)-N-isobutylpyrrolidine-3-carboxamide | 472.4 | 9.83 | 133 |
| 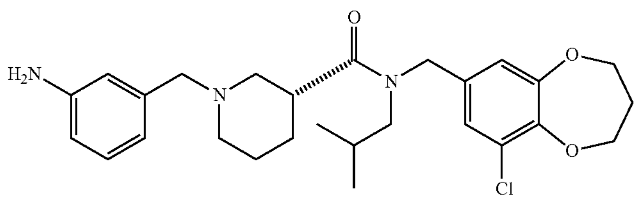 | (−)-(3R)-1-(3-Aminobenzyl)-N-(9-chloro-3,4-dihydro-2H-1,5-benzodioxepin-7-ylmethyl)-N-isobutylpiperidine-3-carboxamide | 486.4 | 14.7 | 61.4 |
| 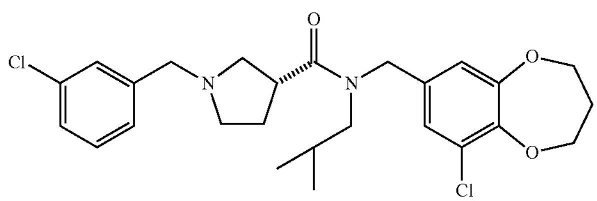 [SMILES: CC(C)CN(Cc1cc(Cl)c2c(c1)OCCCO2)C(=O)[C@@H]1CCN(Cc2cccc(Cl)c2)C1] | (−)-(3R)-1-(3-chlorobenzyl)-N-(9-chloro-3,4-dihydro-2H-1,5-benzodioxepin-7-ylmethyl)-N-isobutylpyrrolidine-3-carboxamide | 491.0 | 19.5 | 83.6 |
| 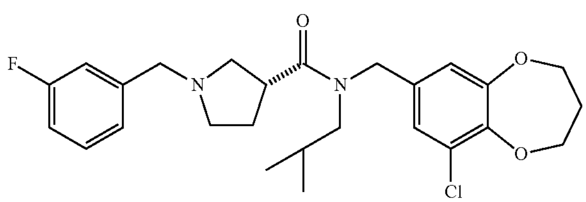 [SMILES: CC(C)CN(Cc1cc(Cl)c2c(c1)OCCCO2)C(=O)[C@@H]1CCN(Cc2cccc(F)c2)C1] | (−)-(3R)-1-(3-fluorobenzyl)-N-(9-chloro-3,4-dihydro-2H-1,5-benzodioxepin-7-ylmethyl)-N-isobutylpyrrolidine-3-carboxamide | 475.1 | 17.9 | |
| 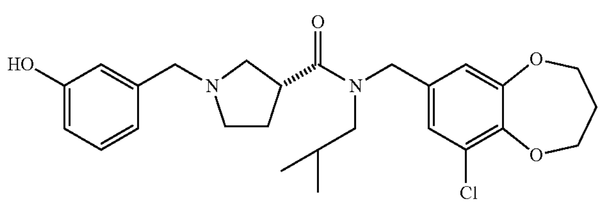 [SMILES: CC(C)CN(Cc1cc(Cl)c2c(c1)OCCCO2)C(=O)[C@@H]1CCN(Cc2cccc(O)c2)C1] | (−)-(3R)-1-(3-Hydroxybenzyl)-N-(9-chloro-3,4-dihydro-2H-1,5-benzodioxepin-7-ylmethyl)-N-isobutylpyrrolidine-3-carboxamide | 473.2 | 0.55 1.76 | 7.1 5.2 |
| 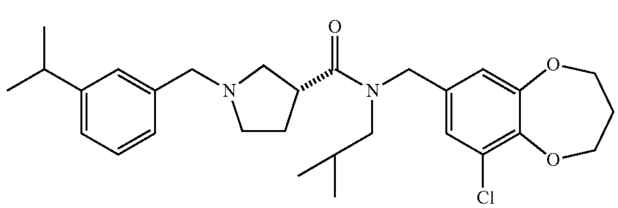 [SMILES: CC(C)CN(Cc1cc(Cl)c2c(c1)OCCCO2)C(=O)[C@@H]1CCN(Cc2cccc(C(C)C)c2)C1] | (−)-(3R)-1-(3-Isopropylbenzyl)-N-(9-chloro-3,4-dihydro-2H-1,5-benzodioxepin-7-ylmethyl)-N-isobutylpyrrolidine-3-carboxamide | 499.5 | 426 | 195 |
| 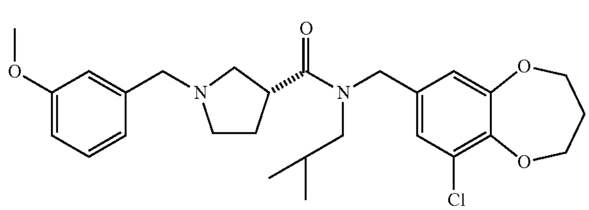 [SMILES: COc1cccc(CN2CC[C@@H](C(=O)N(Cc3cc(Cl)c4c(c3)OCCCO4)CC(C)C)C2)c1] | (−)-(3R)-1-(3-Methoxybenzyl)-N-(9-chloro-3,4-dihydro-2H-1,5-benzodioxepin-7-ylmethyl)-N-isobutylpyrrolidine-3-carboxamide | 487.2 | 1.03 | 4.0 |

-continued

| Structure | Compound Name | Mass Ion (M + 1) | Ki for PKR2 (nM) | Ki for PKR1 (nM) |
|---|---|---|---|---|
| 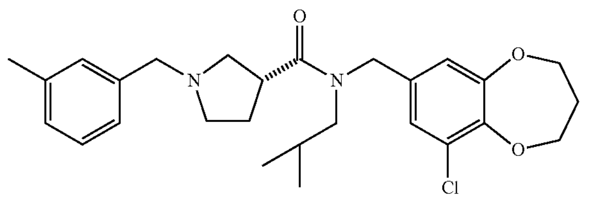 [SMILES: Cc1cccc(CN2CC[C@@H](C(=O)N(Cc3cc(Cl)c4c(c3)OCCCO4)CC(C)C)C2)c1] | (−)-(3R)-1-(3-Methylbenzyl)-N-(9-chloro-3,4-dihydro-2H-1,5-benzodioxepin-7-ylmethyl)-N-isobutylpyrrolidine-3-carboxamide | 471.4 | 15.0 | 29.6 |
| 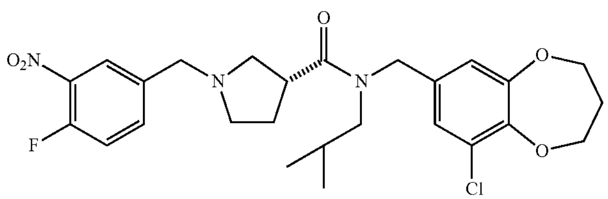 [SMILES: CC(C)CN(Cc1cc(Cl)c2c(c1)OCCCO2)C(=O)[C@@H]1CCN(Cc2ccc(F)c([N+](=O)[O-])c2)C1] | (−)-(3R)-1-(3-Nitro-4-fluorobenzyl)-N-(9-chloro-3,4-dihydro-2H-1,5-benzodioxepin-7-ylmethyl)-N-isobutylpyrrolidine-3-carboxamide | 520.6 | 6.83 | 109 |
| 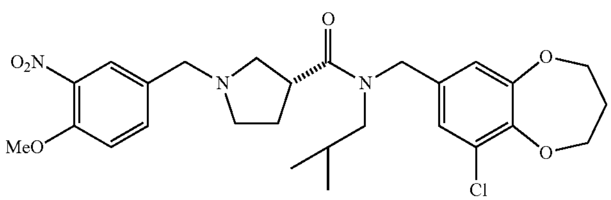 [SMILES: COc1ccc(CN2CC[C@@H](C(=O)N(Cc3cc(Cl)c4c(c3)OCCCO4)CC(C)C)C2)cc1[N+](=O)[O-]] | (−)-(3R)-1-(3-Nitro-4-methoxybenzyl)-N-(9-chloro-3,4-dihydro-2H-1,5-benzodioxepin-7-ylmethyl)-N-isobutylpyrrolidine-3-carboxamide | 532.6 | 57.3 | |
| 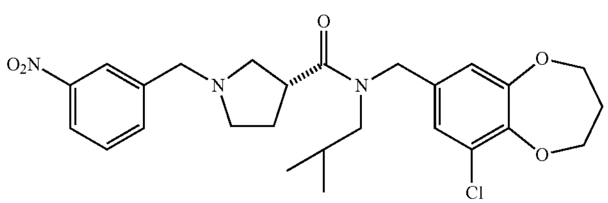 | (−)-(3R)-1-(3-nitrobenzyl)-N-(9-chloro-3,4-dihydro-2H-1,5-benzodioxepin-7-ylmethyl)-N-isobutylpyrrolidine-3-carboxamide | 502.5 | 650 | |
| 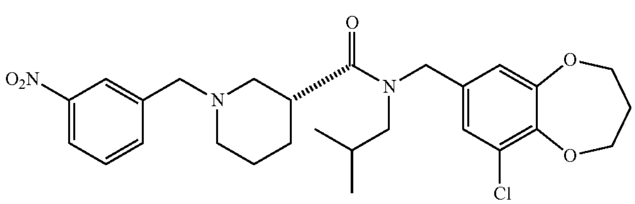 | (−)-(3R)-1-(3-Nitrobenzyl)-N-(9-chloro-3,4-dihydro-2H-1,5-benzodioxepin-7-ylmethyl)-N-isobutylpiperidine-3-carboxamide | 516.4 | 267 | |
| 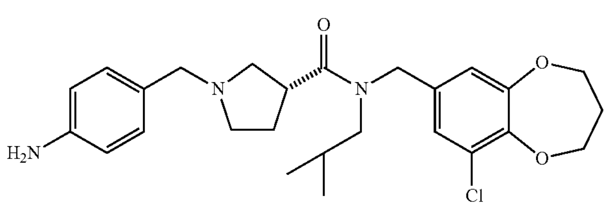 | (−)-(3R)-1-(4-aminobenzyl)-N-(9-chloro-3,4-dihydro-2H-1,5-benzodioxepin-7-ylmethyl)-N-isobutylpyrrolidine-3-carboxamide | 472.4 | 52.8 | |
| 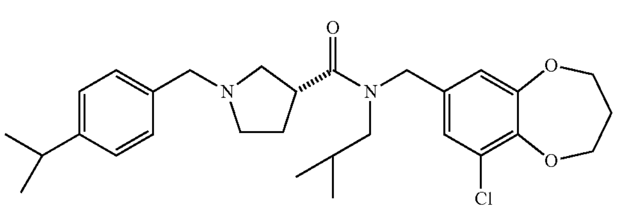 [SMILES: CC(C)CN(Cc1cc(Cl)c2c(c1)OCCCO2)C(=O)[C@@H]1CCN(Cc2ccc(C(C)C)cc2)C1] | (−)-(3R)-1-(4-dimethylaminobenzyl)-N-(9-chloro-3,4-dihydro-2H-1,5-benzodioxepin-7-ylmethyl)-N-isobutylpyrrolidine-3-carboxamide | 500.4 | ND | |

-continued

| Structure | Compound Name | Mass Ion (M + 1) | Ki for PKR2 (nM) | Ki for PKR1 (nM) |
|---|---|---|---|---|
| 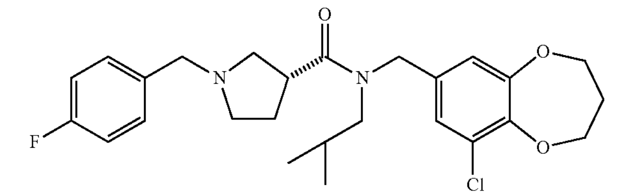 [SMILES: CC(C)CN(Cc1cc(Cl)c2c(c1)OCCCO2)C(=O)[C@@H]1CCN(Cc2ccc(F)cc2)C1] | (−)-(3R)-1-(4-Fluorobenzyl)-N-(9-chloro-3,4-dihydro-2H-1,5-benzodioxepin-7-ylmethyl)-N-isobutylpyrrolidine-3-carboxamide | 475.6 | 4.46 | 40.6 |
| 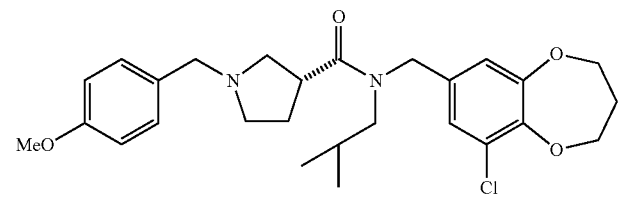 [SMILES: COc1ccc(CN2CC[C@@H](C(=O)N(Cc3cc(Cl)c4c(c3)OCCCO4)CC(C)C)C2)cc1] | (−)-(3R)-1-(4-Methoxybenzyl)-N-(9-chloro-3,4-dihydro-2H-1,5-benzodioxepin-7-ylmethyl)-N-isobutylpyrrolidine-3-carboxamide | 487.6 | 70.7 | |
| 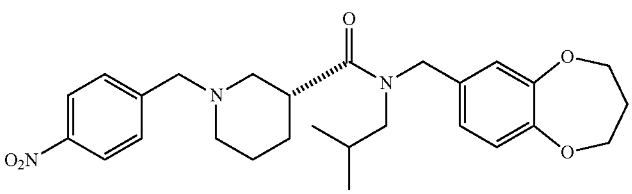 [SMILES: CC(C)CN(Cc1ccc2c(c1)OCCCO2)C(=O)[C@@H]1CCCN(Cc2ccc([N+](=O)[O-])cc2)C1] | (−)-(3R)-1-(4-Nitrobenzyl)-N-(3,4-dihydro-2H-1,5-benzodioxepin-7-ylmethyl)-N-isobutylpiperidine-3-carboxamide | 482.3 | 1070 | |
| 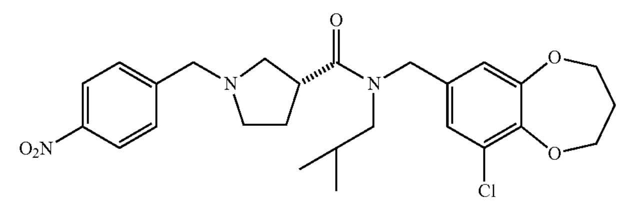 [SMILES: CC(C)CN(Cc1cc(Cl)c2c(c1)OCCCO2)C(=O)[C@@H]1CCN(Cc2ccc([N+](=O)[O-])cc2)C1] | (−)-(3R)-1-(4-nitrobenzyl)-N-(9-chloro-3,4-dihydro-2H-1,5-benzodioxepin-7-ylmethyl)-N-isobutylpyrrolidine-3-carboxamide | 502.5 | 1284 | |
| 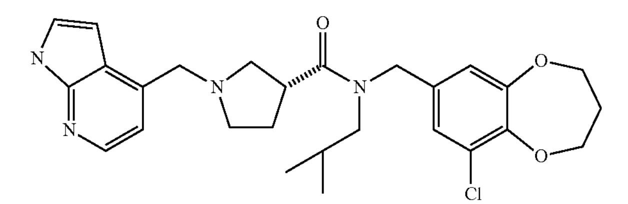 [SMILES: CC(C)CN(Cc1cc(Cl)c2c(c1)OCCCO2)C(=O)[C@@H]1CCN(Cc2ccnc3[nH]ccc23)C1] | (−)-(3R)-1-(7-Azaindol-4-ylmethyl)-N-(9-chloro-3,4-dihydro-2H-1,5-benzodioxepin-7-ylmethyl)-N-isobutylpyrrolidine-3-carboxamide | 497.2 | 41.4 | 41.6 |
| 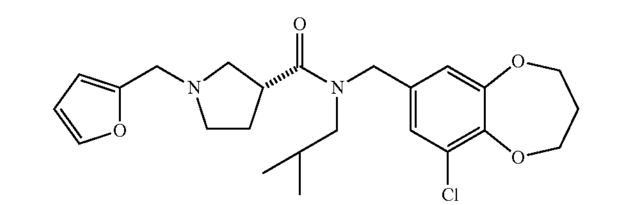 [SMILES: CC(C)CN(Cc1cc(Cl)c2c(c1)OCCCO2)C(=O)[C@@H]1CCN(Cc2ccco2)C1] | (−)-(3R)-1-(Furan-2-ylmethyl)-N-(9-chloro-3,4-dihydro-2H-1,5-benzodioxepin-7-ylmethyl)-N-isobutylpyrrolidine-3-carboxamide | 447.2 | 45.5 | |
| 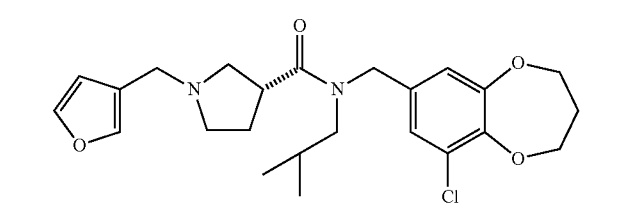 [SMILES: CC(C)CN(Cc1cc(Cl)c2c(c1)OCCCO2)C(=O)[C@@H]1CCN(Cc2ccoc2)C1] | (−)-(3R)-1-(Furan-3-ylmethyl)-N-(9-chloro-3,4-dihydro-2H-1,5-benzodioxepin-7-ylmethyl)-N-isobutylpyrrolidine-3-carboxamide | 447.2 | 264 | |

-continued

| Structure | Compound Name | Mass Ion (M + 1) | Ki for PKR2 (nM) | Ki for PKR1 (nM) |
|---|---|---|---|---|
| 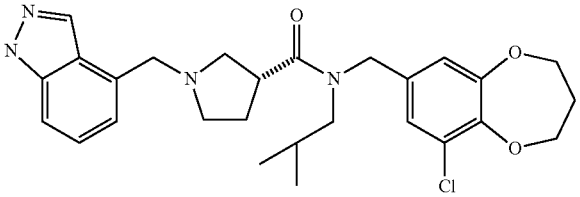 [SMILES: CC(C)CN(Cc1cc(Cl)c2c(c1)OCCCO2)C(=O)[C@@H]1CCN(Cc2cccc3[nH]ncc23)C1] | (−)-(3R)-1-(Indazol-4-ylmethyl)-N-(9-chloro-3,4-dihydro-2H-1,5-benzodioxepin-7-ylmethyl)-N-isobutylpyrrolidine-3-carboxamide | 497.2 | 179 | 2480 |
| 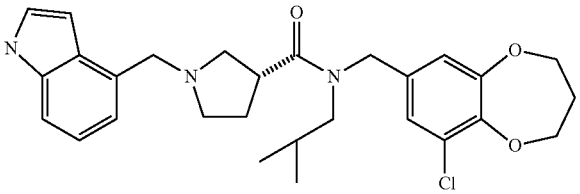 [SMILES: CC(C)CN(Cc1cc(Cl)c2c(c1)OCCCO2)C(=O)[C@@H]1CCN(Cc2cccc3[nH]ccc23)C1] | (−)-(3R)-1-(Indol-4-ylmethyl)-N-(9-chloro-3,4-dihydro-2H-1,5-benzodioxepin-7-ylmethyl)-N-isobutylpyrrolidine-3-carboxamide | 496.2 | 2.50 | 32.0 |
| 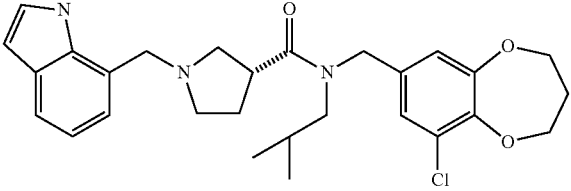 | (−)-(3R)-1-(Indol-7-ylmethyl)-N-(9-chloro-3,4-dihydro-2H-1,5-benzodioxepin-7-ylmethyl)-N-isobutylpyrrolidine-3-carboxamide | 496.3 | 0.514 | 1.98 1.22 |
| 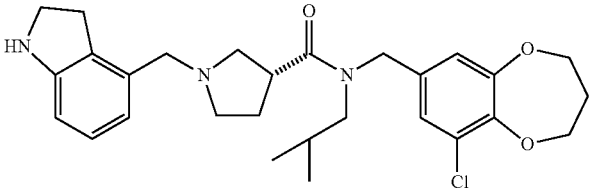 [SMILES: CC(C)CN(Cc1cc(Cl)c2c(c1)OCCCO2)C(=O)[C@@H]1CCN(Cc2cccc3c2CCN3)C1] | (−)-(3R)-1-(Indolin-4-ylmethyl)-N-(9-chloro-3,4-dihydro-2H-1,5-benzodioxepin-7-ylmethyl)-N-isobutylpyrrolidine-3-carboxamide | 498.3 | 0.206 | 4.70 |
| 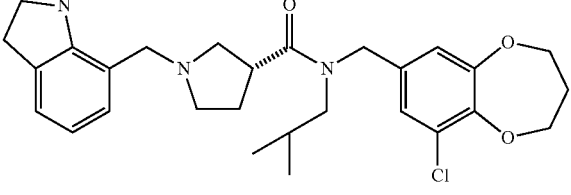 | (−)-(3R)-1-(Indolin-7-ylmethyl)-N-(9-chloro-3,4-dihydro-2H-1,5-benzodioxepin-7-ylmethyl)-N-isobutylpyrrolidine-3-carboxamide | 498.3 | 2.87 | 17.8 |
| 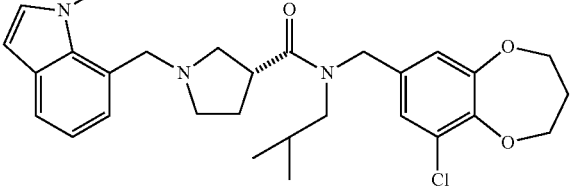 | (−)-(3R)-1-(N-Methyl-indol-7-ylmethyl)-N-(9-chloro-3,4-dihydro-2H-1,5-benzodioxepin-7-ylmethyl)-N-isobutylpyrrolidine-3-carboxamide | 510.3 | 7.24 | 9.08 |
| 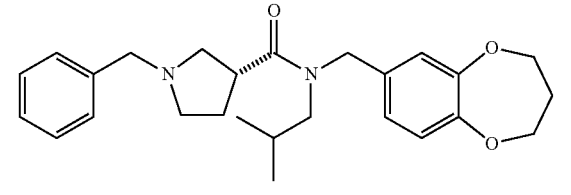 [SMILES: CC(C)CN(Cc1ccc2c(c1)OCCCO2)C(=O)[C@@H]1CCN(Cc2ccccc2)C1] | (−)-(3R)-1-Benzyl-N-(3,4-dihydro-2H-1,5-benzodioxepin-7-ylmethyl)-N-isobutylpyrrolidine-3-carboxamide | 423.3 | 55.6 | |

-continued

| Structure | Compound Name | Mass Ion (M + 1) | Ki for PKR2 (nM) | Ki for PKR1 (nM) |
|---|---|---|---|---|
| 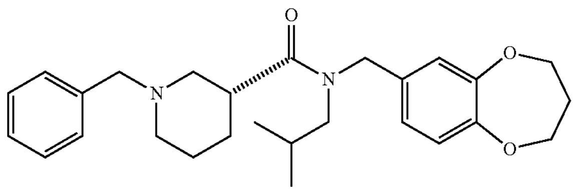 | (−)-(3R)-1-Benzyl-N-(3,4-Dihydro-2H-1,5-benzodioxepin-7-ylmethyl)-N-isobutylpiperidine-3-carboxamide | 437.3 | 20.8 | |
| 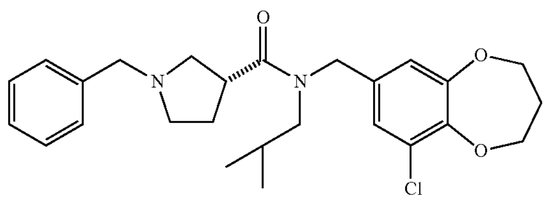 | (−)-(3R)-1-Benzyl-N-(9-chloro-3,4-dihydro-2H-1,5-benzodioxepin-7-ylmethyl)-N-isobutylpyrrolidine-3-carboxamide | 457.3 | 4.16<br>4.56<br>2.66 | 49<br>31.2<br>23.4 |
| 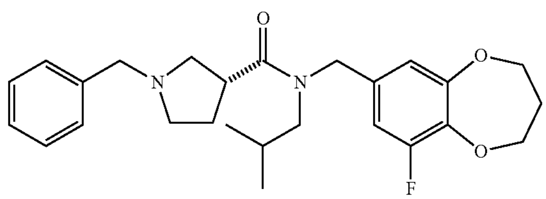 [SMILES: CC(C)CN(Cc1cc(F)c2c(c1)OCCCO2)C(=O)[C@@H]1CCN(Cc2ccccc2)C1] | (−)-(3R)-1-Benzyl-N-(9-fluoro-3,4-dihydro-2H-1,5-benzodioxepin-7-ylmethyl)-N-isobutylpyrrolidine-3-carboxamide | 441.4 | 18.3<br>7.7 | 84.5 |
| 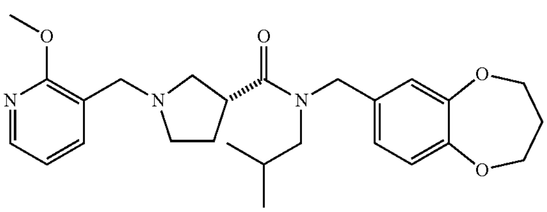 [SMILES: COc1ncccc1CN1CC[C@@H](C(=O)N(Cc2ccc3c(c2)OCCCO3)CC(C)C)C1] | (−)-(3R)-N-(3,4-Dihydro-2H-1,5-benzodioxepin-7-ylmethyl)-N-isobutyl-1-[(2-methoxypyridin-3-ylmethyl)pyrrolidine-3-carboxamide | 454.4 | 3.53 | |
| 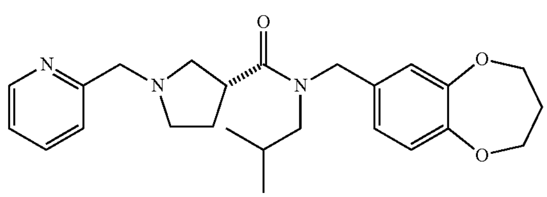 [SMILES: CC(C)CN(Cc1ccc2c(c1)OCCCO2)C(=O)[C@@H]1CCN(Cc2ccccn2)C1] | (−)-(3R)-N-(3,4-Dihydro-2H-1,5-benzodioxepin-7-ylmethyl)-N-isobutyl-1-(pyridin-2-ylmethyl)pyrrolidine-3-carboxamide | 424.3 | 674 | |
| 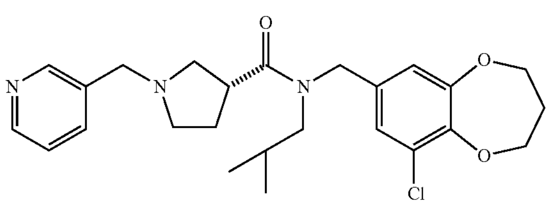 [SMILES: CC(C)CN(Cc1cc(Cl)c2c(c1)OCCCO2)C(=O)[C@@H]1CCN(Cc2cccnc2)C1] | (−)-(3R)-N-(9-chloro-3,4-dihydro-2H-1,5-benzodioxepin-7-ylmethyl)-N-isobutyl-1-(pyridin-3-ylmethyl)pyrrolidine-3-carboxamide | 458.7 | 49.6 | |
| 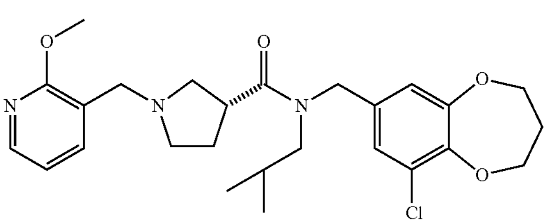 [SMILES: COc1ncccc1CN1CC[C@@H](C(=O)N(Cc2cc(Cl)c3c(c2)OCCCO3)CC(C)C)C1] | (−)-(3R)-N-(9-chloro-3,4-dihydro-2H-1,5-benzodioxepin-7-ylmethyl)-N-isobutyl-1-[(2-methoxypyridin-3-ylmethyl)pyrrolidine-3-carboxamide | 488.1 | 0.71 | 5.34<br>2.82 |

-continued

| Structure | Compound Name | Mass Ion (M + 1) | Ki for PKR2 (nM) | Ki for PKR1 (nM) |
|---|---|---|---|---|
| 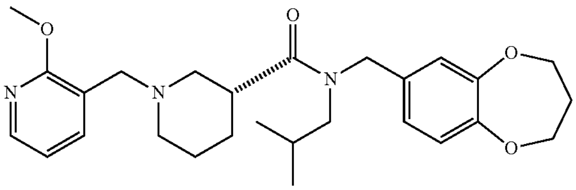 | (−)-(3R)-N-(9-chloro-3,4-dihydro-2H-1,5-benzodioxepin-7-ylmethyl)-N-isobutyl-1-[(2-methoxypyridin-3-ylmethyl)piperidine-3-carboxamide | 468.4 | 24.2 32.8 | |
| 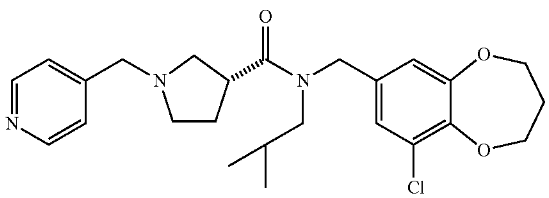 [SMILES: CC(C)CN(Cc1cc(Cl)c2c(c1)OCCCO2)C(=O)[C@@H]1CCN(Cc2ccncc2)C1] | (−)-(3R)-N-(9-Chloro-3,4-dihydro-2H-1,5-benzodioxepin-7-ylmethyl)-N-isobutyl-1-(pyridin-4-ylmethyl)pyrrolidine-3-carboxamide | 458.6 | 13.5 | 214 |
| 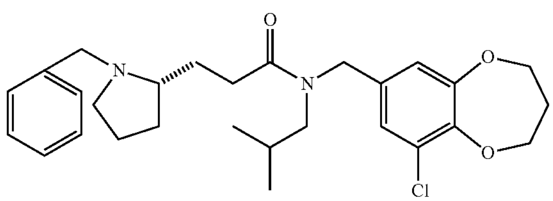 [SMILES: CC(C)CN(Cc1cc(Cl)c2c(c1)OCCCO2)C(=O)CC[C@@H]1CCCN1Cc1ccccc1] | (−)-(R)-3-(1-Benzylpyrrolidin-2-yl)-N-(9-chloro-3,4-dihydro-2H-1,5-benzodioxepin-7-ylmethyl)-N-isobutylpropanamide | 471.2 | 232 | |
| 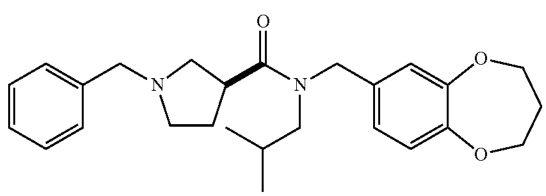 [SMILES: CC(C)CN(Cc1ccc2c(c1)OCCCO2)C(=O)[C@H]1CCN(Cc2ccccc2)C1] | (+)-(3S)-1-Benzyl-N-(3,4-dihydro-2H-1,5-benzodioxepin-7-ylmethyl)-N-isobutylpyrrolidine-3-carboxamide | 423.3 | 1600 | |
| 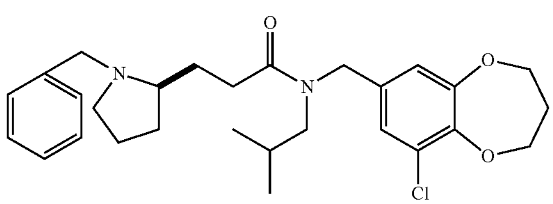 [SMILES: CC(C)CN(Cc1cc(Cl)c2c(c1)OCCCO2)C(=O)CC[C@H]1CCCN1Cc1ccccc1] | (+)-(S)-3-(1-Benzylpyrrolidin-2-yl)-N-(9-chloro-3,4-dihydro-2H-1,5-benzodioxepin-7-ylmethyl)-N-isobutylpropanamide | 471.2 | 908 800 | |
| 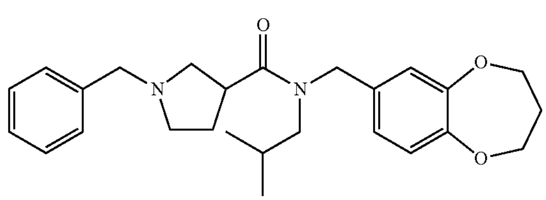 [SMILES: CC(C)CN(Cc1ccc2c(c1)OCCCO2)C(=O)C1CCN(Cc2ccccc2)C1] | (±)-1-Benzyl-N-(3,4-dihydro-2H-1,5-benzodioxepin-7-ylmethyl)-N-isobutylpyrrolidine-3-carboxamide | 423.3 | 65.8 | |
| 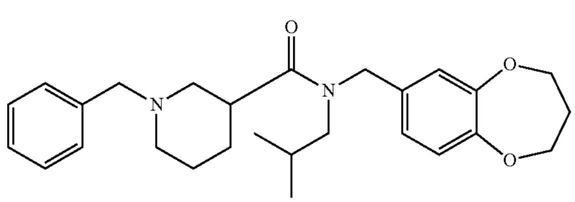 [SMILES: CC(C)CN(Cc1ccc2c(c1)OCCCO2)C(=O)C1CCCN(Cc2ccccc2)C1] | (±)-1-Benzyl-N-(3,4-Dihydro-2H-1,5-benzodioxepin-7-ylmethyl)-N-isobutylpiperidine-3-carboxamide | 437.3 | 27.8 | |

-continued

| Structure | Compound Name | Mass Ion (M + 1) | Ki for PKR2 (nM) | Ki for PKR1 (nM) |
|---|---|---|---|---|
| 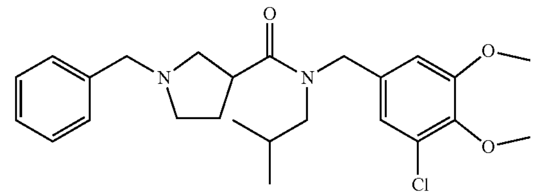 [SMILES: COc1cc(CN(CC(C)C)C(=O)C2CCN(Cc3ccccc3)C2)cc(Cl)c1OC] | (±)-1-Benzyl-N-(3-chloro-4,5-dimethoxy-benzyl)-N-isobutylpyrrolidine-3-carboxamide? | 445.4 | 277 | |
| 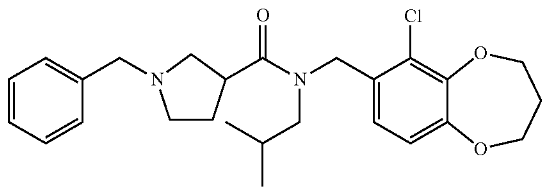 | (±)-1-Benzyl-N-(6-chloro-3,4-dihydro-2H-1,5-benzodioxepin-7-ylmethyl)-N-isobutylpyrrolidine-3-carboxamide | 457.3 | 1880 | |
| 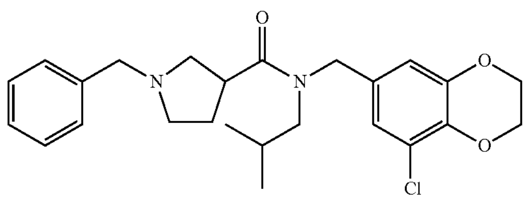 [SMILES: CC(C)CN(Cc1cc(Cl)c2c(c1)OCCO2)C(=O)C1CCN(Cc2ccccc2)C1] | (±)-1-Benzyl-N-(8-chloro-2,3-dihydro-1,4-benzodioxin-6-ylmethyl)-N-isobutylpyrrolidine-3-carboxamide | 443.3 | 37.6 | |
| 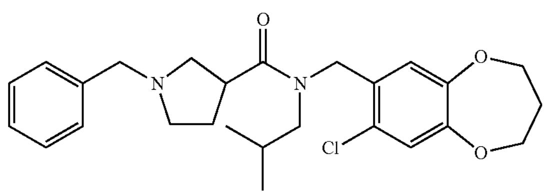 [SMILES: CC(C)CN(Cc1cc2c(cc1Cl)OCCCO2)C(=O)C1CCN(Cc2ccccc2)C1] | (±)-1-Benzyl-N-(8-chloro-3,4-dihydro-2H-1,5-benzodioxepin-7-ylmethyl)-N-isobutylpyrrolidine-3-carboxamide | 457.3 | 1630 | |
| 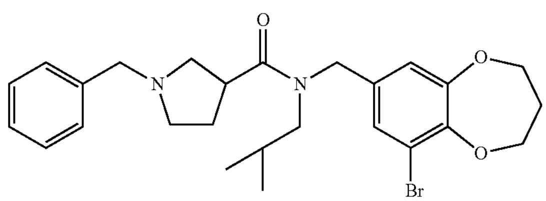 | (±)-1-Benzyl-N-(9-bromo-3,4-dihydro-2H-1,5-benzodioxepin-7-ylmethyl)-N-isobutylpyrrolidine-3-carboxamide | 501.3 | 21.9 | |
| 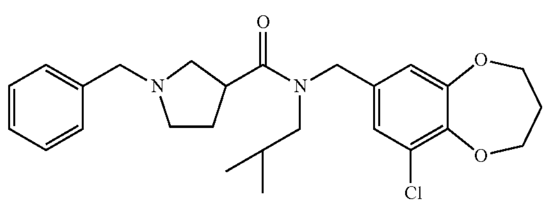 | (±)-1-Benzyl-N-(9-chloro-3,4-dihydro-2H-1,5-benzodioxepin-7-ylmethyl)-N-isobutylpyrrolidine-3-carboxamide | 457.3 | 4.82 | 9.98 |
| 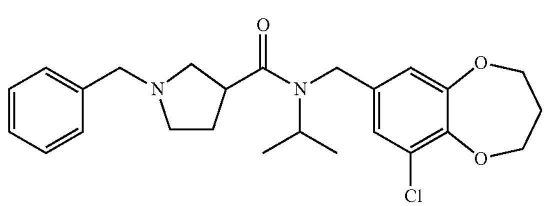 [SMILES: CC(C)N(Cc1cc(Cl)c2c(c1)OCCCO2)C(=O)C1CCN(Cc2ccccc2)C1] | (±)-1-Benzyl-N-(9-chloro-3,4-dihydro-2H-1,5-benzodioxepin-7-ylmethyl)-N-isopropyl pyrrolidine-3-carboxamide | 443.3 | 1190 | |

-continued

| Structure | Compound Name | Mass Ion (M + 1) | Ki for PKR2 (nM) | Ki for PKR1 (nM) |
|---|---|---|---|---|
| 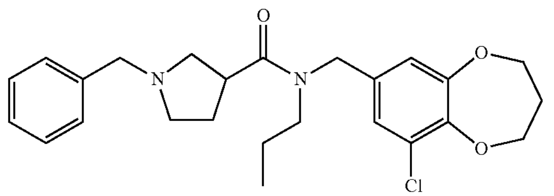 [SMILES: CCCN(Cc1cc(Cl)c2c(c1)OCCCO2)C(=O)C1CCN(Cc2ccccc2)C1] | (±)-1-Benzyl-N-(9-chloro-3,4-dihydro-2H-1,5-benzodioxepin-7-ylmethyl)-N-propyl pyrrolidine-3-carboxamide | 443.4 | 58.2 | |
| 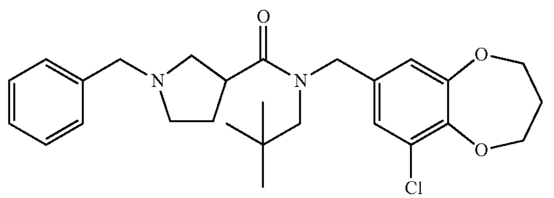 [SMILES: CC(C)(C)CN(Cc1cc(Cl)c2c(c1)OCCCO2)C(=O)C1CCN(Cc2ccccc2)C1] | (±)-1-Benzyl-N-(9-chloro-3,4-dihydro-2H-1,5-benzodioxepin-7-ylmethyl)-N-(2,2-dimethylpropyl) pyrrolidine-3-carboxamide | 471.3 | 107 | |
| 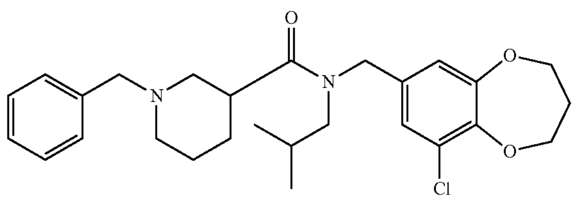 [SMILES: CC(C)CN(Cc1cc(Cl)c2c(c1)OCCCO2)C(=O)C1CCCN(Cc2ccccc2)C1] | (±)-1-Benzyl-N-(9-chloro-3,4-dihydro-2H-1,5-benzodioxepin-7-ylmethyl)-N-isobutylpiperidine-3-carboxamide | 471.3 | 33.9 | |
| 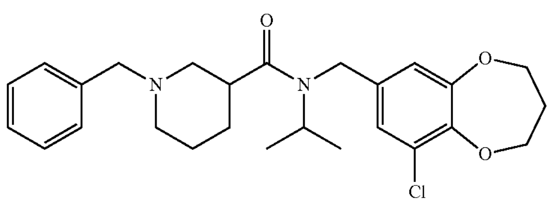 [SMILES: CC(C)N(Cc1cc(Cl)c2c(c1)OCCCO2)C(=O)C1CCCN(Cc2ccccc2)C1] | (±)-1-Benzyl-N-(9-chloro-3,4-dihydro-2H-1,5-benzodioxepin-7-ylmethyl)-N-isopropyl piperidine-3-carboxamide | 457.3 | 4430 | |
| 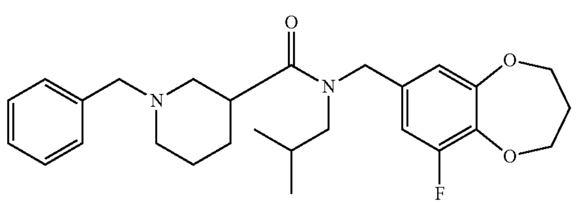 [SMILES: CC(C)CN(Cc1cc(F)c2c(c1)OCCCO2)C(=O)C1CCCN(Cc2ccccc2)C1] | (±)-1-Benzyl-N-(9-fluoro-3,4-dihydro-2H-1,5-benzodioxepin-7-ylmethyl)-N-isobutylpiperidine-3-carboxamide | 455.7 | 66.5 149 | |
| 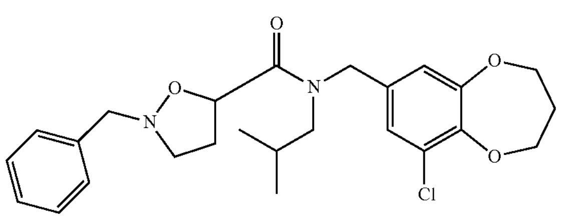 [SMILES: CC(C)CN(Cc1cc(Cl)c2c(c1)OCCCO2)C(=O)C1CCN(Cc2ccccc2)O1] | (±)-2-Benzyl-N-(9-chloro-3,4-dihydro-2H-1,5-benzodioxepin-7-ylmethyl)-N-isobutylisoxazolidin-5-carboxamide | 459.2 | 976 | 2200 |
| 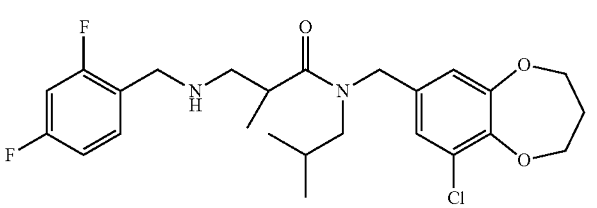 [SMILES: CC(C)CN(Cc1cc(Cl)c2c(c1)OCCCO2)C(=O)C(C)CNCc1ccc(F)cc1F] | (±)-2-Methyl-3-((2,4-difluoro)benzylamino)-N-(9-chloro-3,4-dihydro-2H-1,5-benzodioxepin-7-ylmethyl)-N-isobutylpropanamide | 481.3 | 28.2 21.4 | 147 |

-continued

| Structure | Compound Name | Mass Ion (M + 1) | Ki for PKR2 (nM) | Ki for PKR1 (nM) |
|---|---|---|---|---|
| 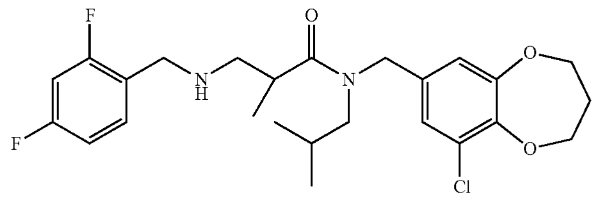 [SMILES: CC(C)CN(Cc1cc(Cl)c2c(c1)OCCCO2)C(=O)C(C)CNCc1ccc(F)cc1F] | (±)-2-Methyl-3-((2,4-difluoro)benzylamino)-N-(9-chloro-3,4-dihydro-2H-1,5-benzodioxepin-7-ylmethyl)-N-isobutylpropanamide | 481.3 | | 147 |
| 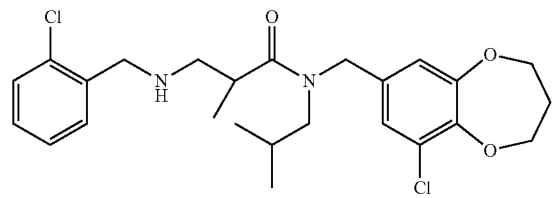 [SMILES: CC(C)CN(Cc1cc(Cl)c2c(c1)OCCCO2)C(=O)C(C)CNCc1ccccc1Cl] | (±)-2-Methyl-3-((2-chloro)benzylamino)-N-(9-chloro-3,4-dihydro-2H-1,5-benzodioxepin-7-ylmethyl)-N-isobutylpropanamide | 479.4 | 24.2 | |
| 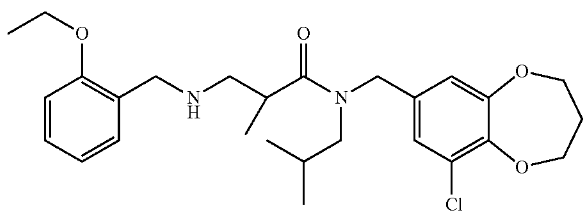 [SMILES: CCOc1ccccc1CNCC(C)C(=O)N(Cc1cc(Cl)c2c(c1)OCCCO2)CC(C)C] | (±)-2-Methyl-3-((2-ethoxy)benzylamino)-N-(9-chloro-3,4-dihydro-2H-1,5-benzodioxepin-7-ylmethyl)-N-isobutylpropanamide | 489.2 | 55.2 | |
| 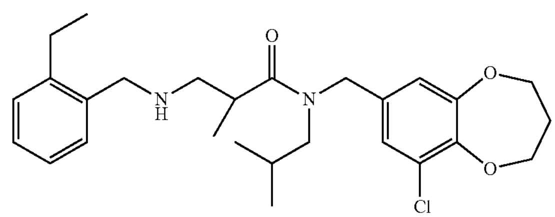 [SMILES: CCc1ccccc1CNCC(C)C(=O)N(Cc1cc(Cl)c2c(c1)OCCCO2)CC(C)C] | (±)-2-Methyl-3-((2-ethyl)benzylamino)-N-(9-chloro-3,4-dihydro-2H-1,5-benzodioxepin-7-ylmethyl)-N-isobutylpropanamide | 473.4 | 7.18 31.4 | 51.0 |
| 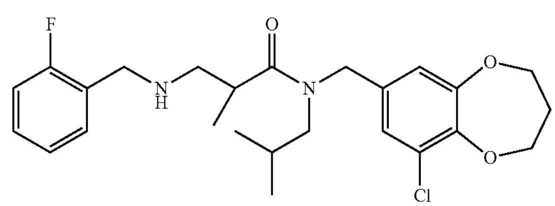 [SMILES: CC(C)CN(Cc1cc(Cl)c2c(c1)OCCCO2)C(=O)C(C)CNCc1ccccc1F] | (±)-2-Methyl-3-((2-fluoro)benzylamino)-N-(9-chloro-3,4-dihydro-2H-1,5-benzodioxepin-7-ylmethyl)-N-isobutylpropanamide | 463.4 | 6.42 8.62 | 97.8 |
| 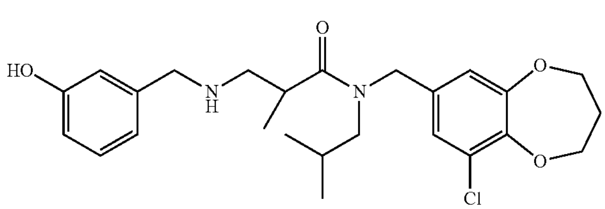 | (±)-2-Methyl-3-((2-hydroxybenzyl)methylamino)-N-(9-chloro-3,4-dihydro-2H-1,5-benzodioxepin-7-ylmethyl)-N-isobutylpropanamide | 461.3 | 1.62 1.77 | 23.5 7.8 |
| 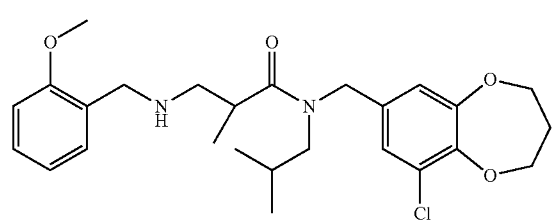 [SMILES: COc1ccccc1CNCC(C)C(=O)N(Cc1cc(Cl)c2c(c1)OCCCO2)CC(C)C] | (±)-2-Methyl-3-((2-methoxy)benzylamino)-N-(9-chloro-3,4-dihydro-2H-1,5-benzodioxepin-7-ylmethyl)-N-isobutylpropanamide | 475.3 | 0.72 | 25.2 |

-continued

| Structure | Compound Name | Mass Ion (M + 1) | Ki for PKR2 (nM) | Ki for PKR1 (nM) |
|---|---|---|---|---|
| 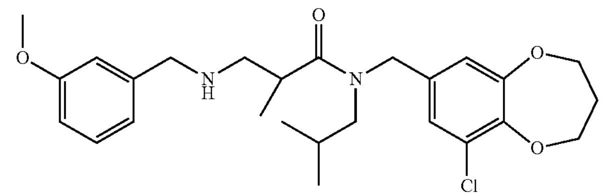 [SMILES: COc1cccc(CNCC(C)C(=O)N(Cc2cc(Cl)c3c(c2)OCCCO3)CC(C)C)c1] | (±)-2-Methyl-3-((2-methoxybenzyl)methylamino)-N-(9-chloro-3,4-dihydro-2H-1,5-benzodioxepin-7-ylmethyl)-N-isobutylpropanamide | 475.3 | 1.76 | 7.26 |
| 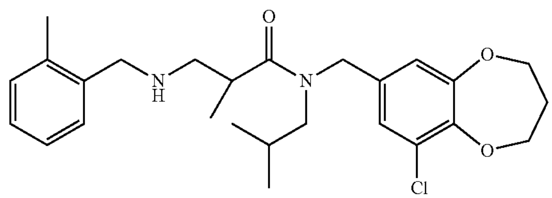 [SMILES: Cc1ccccc1CNCC(C)C(=O)N(Cc1cc(Cl)c2c(c1)OCCCO2)CC(C)C] | (±)-2-Methyl-3-((2-methyl)benzylamino)-N-(9-chloro-3,4-dihydro-2H-1,5-benzodioxepin-7-ylmethyl)-N-isobutylpropanamide | 459.3 | 9.08 5.06 | 19.6 |
| 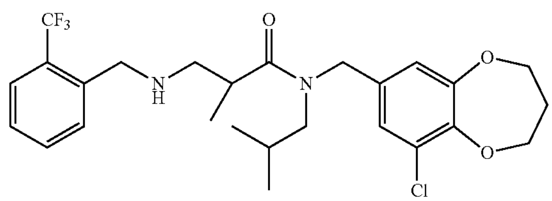 | (±)-2-Methyl-3-((2-trifluoromethyl)benzylamino)-N-(9-chloro-3,4-dihydro-2H-1,5-benzodioxepin-7-ylmethyl)-N-isobutylpropanamide | 513.3 | 34.6 | |
| 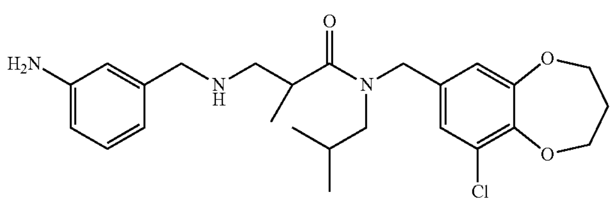 | (±)-2-Methyl-3-((3-amino)benzylamino)-N-(9-chloro-3,4-dihydro-2H-1,5-benzodioxepin-7-ylmethyl)-N-isobutylpropanamide | 460.3 | 6.64 | 27.0 19.8 18.6 |
| 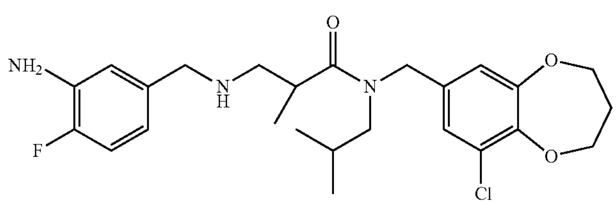 | (±)-2-Methyl-3-((3-amino-4-fluoro)benzylamino)-N-(9-chloro-3,4-dihydro-2H-1,5-benzodioxepin-7-ylmethyl)-N-isobutylpropanamide | 478.4 | 155 | 151 |
| 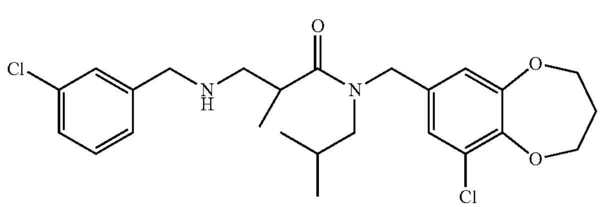 [SMILES: CC(C)CN(Cc1cc(Cl)c2c(c1)OCCCO2)C(=O)C(C)CNCc1cccc(Cl)c1] | (±)-2-Methyl-3-((3-chloro)benzylamino)-N-(9-chloro-3,4-dihydro-2H-1,5-benzodioxepin-7-ylmethyl)-N-isobutylpropanamide | 479.4 | 39.8 | |
| 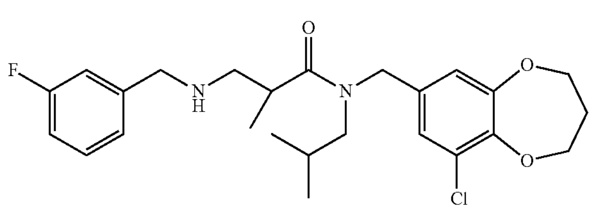 [SMILES: CC(C)CN(Cc1cc(Cl)c2c(c1)OCCCO2)C(=O)C(C)CNCc1cccc(F)c1] | (±)-2-Methyl-3-((3-fluoro)benzylamino)-N-(9-chloro-3,4-dihydro-2H-1,5-benzodioxepin-7-ylmethyl)-N-isobutylpropanamide | 463.4 | 28.8 | |

| Structure | Compound Name | Mass Ion (M + 1) | Ki for PKR2 (nM) | Ki for PKR1 (nM) |
|---|---|---|---|---|
| 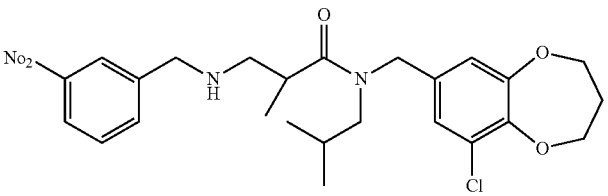 | (±)-2-Methyl-3-((3-nitro)benzylamino)-N-(9-chloro-3,4-dihydro-2H-1,5-benzodioxepin-7-ylmethyl)-N-isobutylpropanamide | 490.3 | 474 | |
| 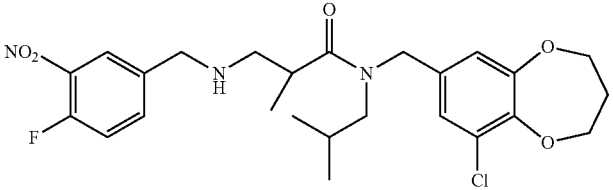 | (±)-2-Methyl-3-((3-nitro-4-fluoro)benzylamino)-N-(9-chloro-3,4-dihydro-2H-1,5-benzodioxepin-7-ylmethyl)-N-isobutylpropanamide | 508.4 | ND | |
| 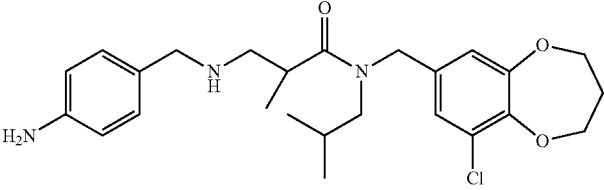 | (±)-2-Methyl-3-((4-amino)benzylamino)-N-(9-chloro-3,4-dihydro-2H-1,5-benzodioxepin-7-ylmethyl)-N-isobutylpropanamide | 460.3 | 22.2 | |
| 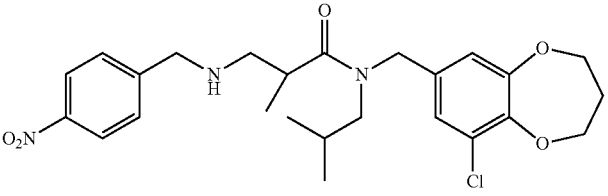 [SMILES: CC(C)CN(Cc1cc(Cl)c2c(c1)OCCCO2)C(=O)C(C)CNCc1ccc([N+](=O)[O-])cc1] | (±)-2-Methyl-3-((4-nitro)benzylamino)-N-(9-chloro-3,4-dihydro-2H-1,5-benzodioxepin-7-ylmethyl)-N-isobutylpropanamide | 490.3 | 252 | |
| 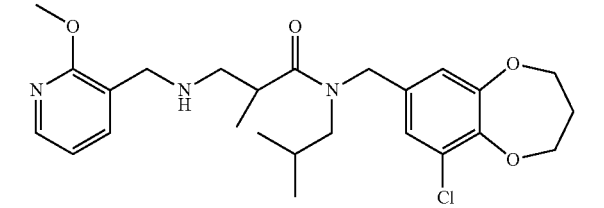 [SMILES: COc1ncccc1CNCC(C)C(=O)N(Cc1cc(Cl)c2c(c1)OCCCO2)CC(C)C] | (±)-2-Methyl-3-(1-((2-methoxypyridin-3-ylmethyl)amino)-N-(9-chloro-3,4-dihydro-2H-1,5-benzodioxepin-7-ylmethyl)-N-isobutylpropanamide | 476.3 | 1.06 1.82 | 44.8 |
| 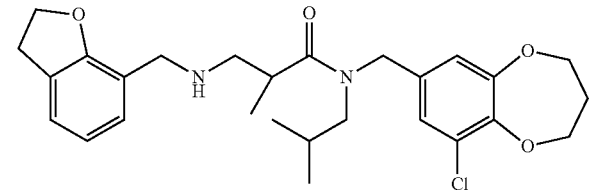 | (±)-2-Methyl-3-(2,3-dihydro-1-benzofuran-7-ylmethylamino)-N-(9-chloro-3,4-dihydro-2H-1,5-benzodioxepin-7-ylmethyl)-N-isobutylpropanamide | 487.3 | 2.38 2.28 | 13.6 7.44 |
| 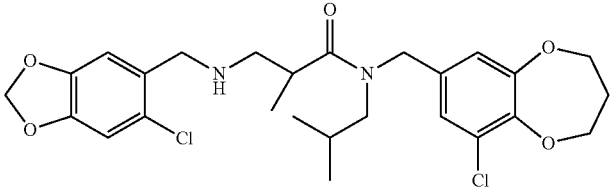 [SMILES: CC(C)CN(Cc1cc(Cl)c2c(c1)OCCCO2)C(=O)C(C)CNCc1cc2c(cc1Cl)OCO2] | (±)-2-Methyl-3-(6-chloro-1,3-benzodioxole-5-methylamino)-N-(9-chloro-3,4-dihydro-2H-1,5-benzodioxepin-7-ylmethyl)-N-isobutylpropanamide | 523.6 | 74.5 | |

-continued

| Structure | Compound Name | Mass Ion (M + 1) | Ki for PKR2 (nM) | Ki for PKR1 (nM) |
|---|---|---|---|---|
| 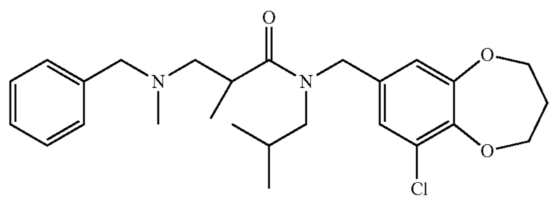 [SMILES: CC(C)CN(Cc1cc(Cl)c2c(c1)OCCCO2)C(=O)C(C)CN(C)Cc1ccccc1] | (±)-2-Methyl-3-(benzyl(methyl)amino)-N-(9-chloro-3,4-dihydro-2H-1,5-benzodioxepin-7-ylmethyl)-N-isobutylpropanamide | 459.2 | 795 | |
| 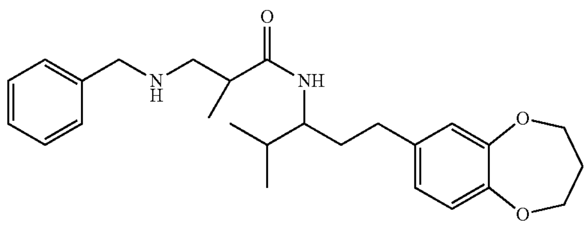 [SMILES: CC(CNCc1ccccc1)C(=O)NC(CCc1ccc2c(c1)OCCCO2)C(C)C] | (±)-2-Methyl-3-(benzylamino)-N-(3,4-dihydro-2H-1,5-benzodioxepin-7-yl-α-isopropylpropyl)propanamide | 425.2 | 227 | 573 706 |
| 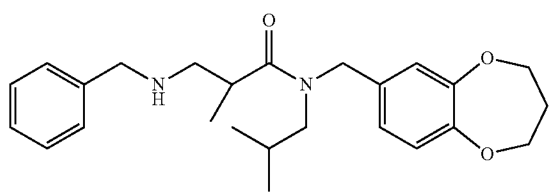 [SMILES: CC(C)CN(Cc1ccc2c(c1)OCCCO2)C(=O)C(C)CNCc1ccccc1] | (±)-2-Methyl-3-(benzylamino)-N-(3,4-dihydro-2H-1,5-benzodioxepin-7-ylmethyl)-N-isobutylpropanamide | 411.2 | 130 | |
| 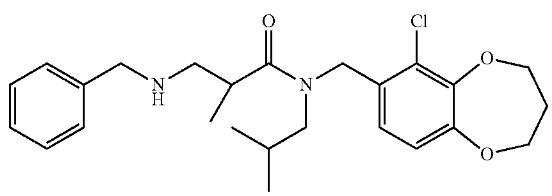 [SMILES: CC(C)CN(Cc1ccc2c(c1Cl)OCCCO2)C(=O)C(C)CNCc1ccccc1] | (±)-2-Methyl-3-(benzylamino)-N-(6-chloro-3,4-dihydro-2H-1,5-benzodioxepin-7-ylmethyl)-N-isobutylpropanamide | 445.2 | 330 | |
| 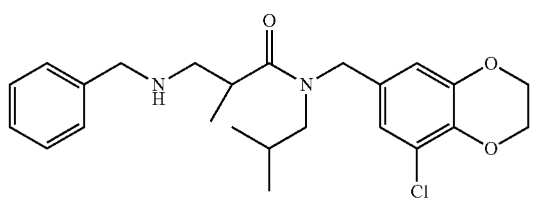 [SMILES: CC(C)CN(Cc1cc(Cl)c2c(c1)OCCO2)C(=O)C(C)CNCc1ccccc1] | (±)-2-Methyl-3-(benzylamino)-N-(8-chloro-2,3-dihydro-1,4-benzodioxin-6-ylmethyl)-N-isobutylpropanamide | 431.3 | 44.4 66.6 | 134 224 |
| 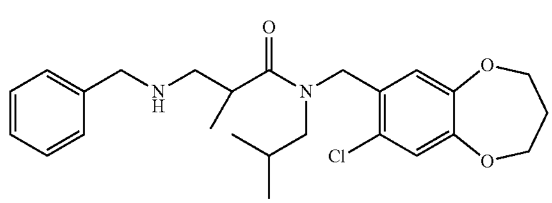 [SMILES: CC(C)CN(Cc1cc2c(cc1Cl)OCCCO2)C(=O)C(C)CNCc1ccccc1] | (±)-2-Methyl-3-(benzylamino)-N-(8-chloro-3,4-dihydro-2H-1,5-benzodioxepin-7-ylmethyl)-N-isobutylpropanamide | 445.2 | 796 | |
| 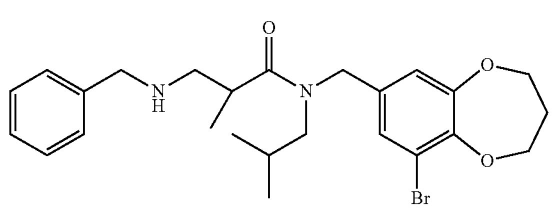 [SMILES: CC(C)CN(Cc1cc(Br)c2c(c1)OCCCO2)C(=O)C(C)CNCc1ccccc1] | (±)-2-Methyl-3-(benzylamino)-N-(9-bromo-3,4-dihydro-2H-1,5-benzodioxepin-7-ylmethyl)-N-isobutylpropanamide | 489.3 | 17.4 | |

-continued

| Structure | Compound Name | Mass Ion (M + 1) | Ki for PKR2 (nM) | Ki for PKR1 (nM) |
|---|---|---|---|---|
| 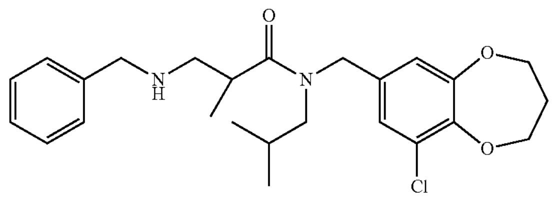 [SMILES: CC(C)CN(Cc1cc(Cl)c2c(c1)OCCCO2)C(=O)C(C)CNCc1ccccc1] | (±)-2-Methyl-3-(benzylamino)-N-(9-chloro-3,4-dihydro-2H-1,5-benzodioxepin-7-ylmethyl)-N-isobutylpropanamide | 445.2 | 8.3 | 85.8 |
| 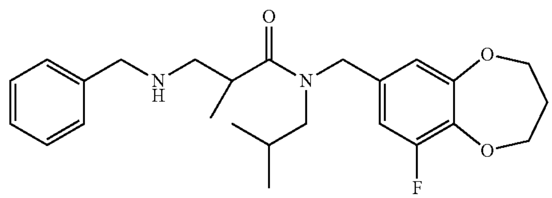 [SMILES: CC(C)CN(Cc1cc(F)c2c(c1)OCCCO2)C(=O)C(C)CNCc1ccccc1] | (±)-2-Methyl-3-(benzylamino)-N-(9-fluoro-3,4-dihydro-2H-1,5-benzodioxepin-7-ylmethyl)-N-isobutylpropanamide | 429.3 | 11.4 | 62.4 |
| 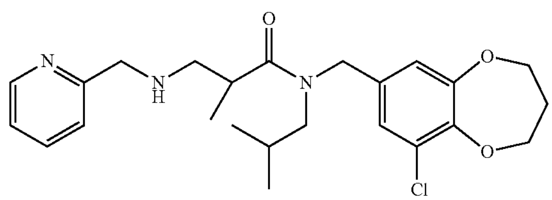 [SMILES: CC(C)CN(Cc1cc(Cl)c2c(c1)OCCCO2)C(=O)C(C)CNCc1ccccn1] | (±)-2-Methyl-3-(pyridin-2-ylmethylamino)-N-(9-chloro-3,4-dihydro-2H-1,5-benzodioxepin-7-ylmethyl)-N-isobutylpropanamide | 446.4 | 32.6 | 192 |
| 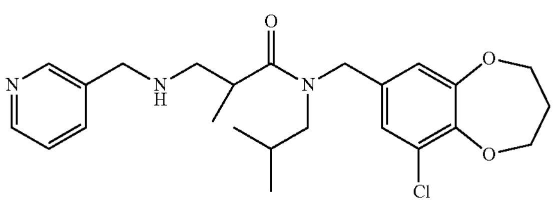 [SMILES: CC(C)CN(Cc1cc(Cl)c2c(c1)OCCCO2)C(=O)C(C)CNCc1cccnc1] | (±)-2-Methyl-3-(pyridin-3-ylmethylamino)-N-(9-chloro-3,4-dihydro-2H-1,5-benzodioxepin-7-ylmethyl)-N-isobutylpropanamide | 446.4 | 31.2 | 570 |
| 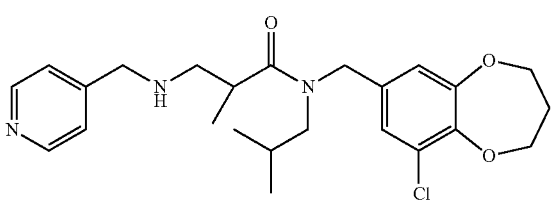 [SMILES: CC(C)CN(Cc1cc(Cl)c2c(c1)OCCCO2)C(=O)C(C)CNCc1ccncc1] | (±)-2-Methyl-3-(pyridin-4-ylmethylamino)-N-(9-chloro-3,4-dihydro-2H-1,5-benzodioxepin-7-ylmethyl)-N-isobutylpropanamide | 446.4 | 1058 | >10,000 |
| 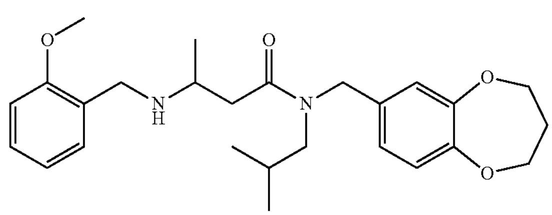 [SMILES: COc1ccccc1CNC(C)CC(=O)N(Cc1ccc2c(c1)OCCCO2)CC(C)C] | (±)-3-Methyl-3-((2-methoxy)benzylamino)-N-(3,4-dihydro-2H-1,5-benzodioxepin-7-ylmethyl)-N-isobutylpropanamide | 441.2 | 734 | |
| 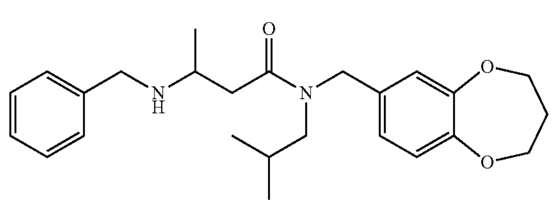 [SMILES: CC(C)CN(Cc1ccc2c(c1)OCCCO2)C(=O)CC(C)NCc1ccccc1] | (±)-3-Methyl-3-(benzylamino)-N-(3,4-dihydro-2H-1,5-benzodioxepin-7-ylmethyl)-N-isobutylpropanamide | 411.2 | 2680 | |

-continued

| Structure | Compound Name | Mass Ion (M + 1) | Ki for PKR2 (nM) | Ki for PKR1 (nM) |
|---|---|---|---|---|
| 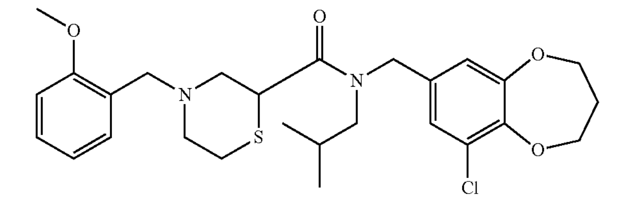 [SMILES: COc1ccccc1CN1CCSC(C(=O)N(Cc2cc(Cl)c3c(c2)OCCCO3)CC(C)C)C1] | (±)-4-(2-Methoxybenzyl)-N-(9-chloro-3,4-dihydro-2H-1,5-benzodioxepin-7-ylmethyl)-N-isobutylthiomorpholine-2-carboxamide | 519.4 | 8.13 | 50.4 |
| 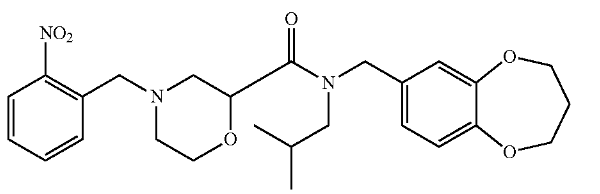 [SMILES: CC(C)CN(Cc1ccc2c(c1)OCCCO2)C(=O)C1CN(Cc2ccccc2[N+](=O)[O-])CCO1] | (±)-4-(2-Nitrobenzyl)-N-(3,4-dihydro-2H-1,5-benzodioxepin-7-ylmethyl)-N-isobutylmorpholine-2-carboxamide | 484.3 | 477 | 713 |
| 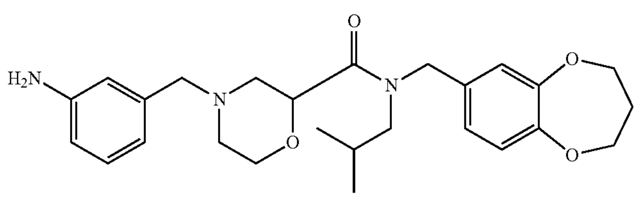 | (±)-4-(3-Aminobenzyl)-N-(3,4-dihydro-2H-1,5-benzodioxepin-7-ylmethyl)-N-isobutylmorpholine-2-carboxamide | 454.3 | 27.5 | |
| 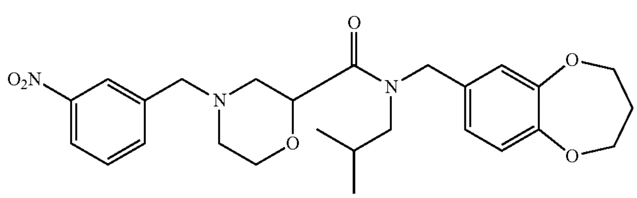 [SMILES: CC(C)CN(Cc1ccc2c(c1)OCCCO2)C(=O)C1CN(Cc2cccc([N+](=O)[O-])c2)CCO1] | (±)-4-(3-Nitrobenzyl)-N-(3,4-dihydro-2H-1,5-benzodioxepin-7-ylmethyl)-N-isobutylmorpholine-2-carboxamide | 484.3 | 1110 | 230 |
| 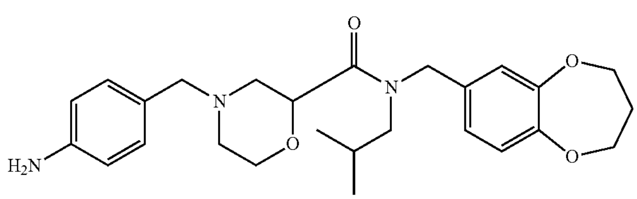 | (±)-4-(4-Aminobenzyl)-N-(3,4-dihydro-2H-1,5-benzodioxepin-7-ylmethyl)-N-isobutylmorpholine-2-carboxamide | 454.3 | 138 | |
| 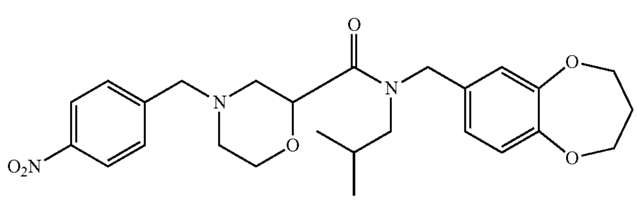 [SMILES: CC(C)CN(Cc1ccc2c(c1)OCCCO2)C(=O)C1CN(Cc2ccc([N+](=O)[O-])cc2)CCO1] | (±)-4-(4-Nitrobenzyl)-N-(3,4-dihydro-2H-1,5-benzodioxepin-7-ylmethyl)-N-isobutylmorpholine-2-carboxamide | 484.3 | 1700 | 1640 |
| 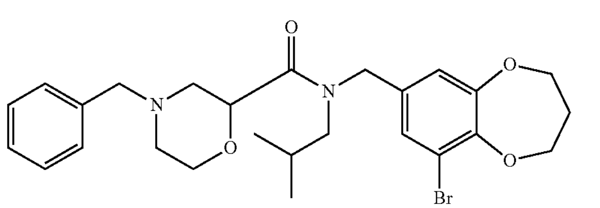 [SMILES: CC(C)CN(Cc1cc(Br)c2c(c1)OCCCO2)C(=O)C1CN(Cc2ccccc2)CCO1] | (±)-4-Benzyl-N-(9-Bromo-3,4-dihydro-2H-1,5-benzodioxepin-7-ylmethyl)-N-isobutylmorpholine-2-carboxamide | 517.6 | 26.9 | |

| Structure | Compound Name | Mass Ion (M + 1) | Ki for PKR2 (nM) | Ki for PKR1 (nM) |
|---|---|---|---|---|
| 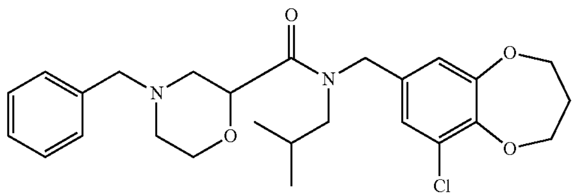 | (±)-4-Benzyl-N-(9-chloro-3,4-dihydro-2H-1,5-benzodioxepin-7-ylmethyl)-N-isobutylmorpholine-2-carboxamide | 473.4 | 10.6<br>6.64 | 22.8<br>23.0 |
| | (±)-4-Benzyl-N-(9-chloro-3,4-dihydro-2H-1,5-benzodioxepin-7-ylmethyl)-N-isobutylthiomorpholine-2-carboxamide | 489.4 | 13.5 | 49.6 |
| | (±)-4-Benzyl-N-(9-chloro-3,4-dihydro-2H-1,5-benzodioxepin-7-ylmethyl)-N-isobutylthiomorpholine-2-carboxamide | 455.4 | 111 | |
| 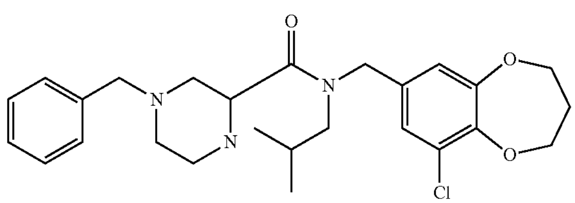 [SMILES: CC(C)CN(Cc1cc(Cl)c2c(c1)OCCCO2)C(=O)C1CN(Cc2ccccc2)CCN1] | (±)-4-Benzyl-N-(9-chloro-3,4-dihydro-2H-1,5-benzodioxepin-7-ylmethyl)-N-isobutylpiperazine-2-carboxamide | 472.4 | 27.2 | 216 |
| 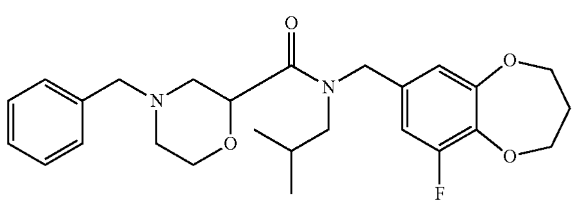 [SMILES: CC(C)CN(Cc1cc(F)c2c(c1)OCCCO2)C(=O)C1CN(Cc2ccccc2)CCO1] | (±)-4-Benzyl-N-(9-fluoro-3,4-dihydro-2H-1,5-benzodioxepin-7-ylmethyl)-N-isobutylmorpholine-2-carboxamide | 457.4 | 11.1 | 164 |
| 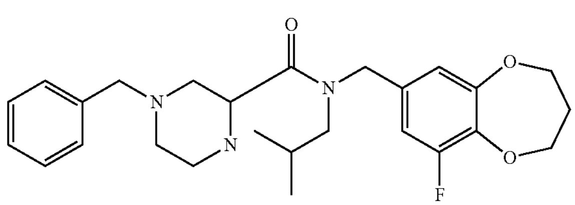 [SMILES: CC(C)CN(Cc1cc(F)c2c(c1)OCCCO2)C(=O)C1CN(Cc2ccccc2)CCN1] | (±)-4-Benzyl-N-(9-fluoro-3,4-dihydro-2H-1,5-benzodioxepin-7-ylmethyl)-N-isobutylpiperazine-2-carboxamide | 456.4 | 94.5 | |
| 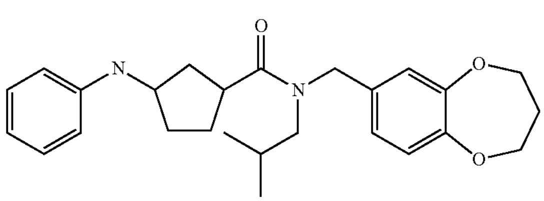 [SMILES: CC(C)CN(Cc1ccc2c(c1)OCCCO2)C(=O)C1CCC(Nc2ccccc2)C1] | (±)-N-(3,4-Dihydro-2H-1,5-benzodioxepin-7-ylmethyl)-N-isobutyl-3-(phenylamino)cyclopentane-carboxamide | 423.3 | 285 | |

| Structure | Compound Name | Mass Ion (M + 1) | Ki for PKR2 (nM) | Ki for PKR1 (nM) |
|---|---|---|---|---|
| 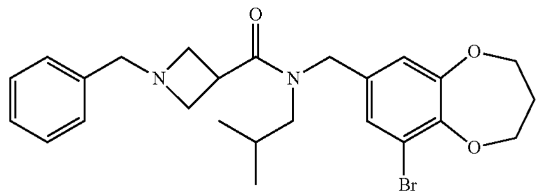 | 1-Benzyl-N-(9-bromo-3,4-dihydro-2H-1,5-benzodioxepin-7-ylmethyl)-N-isobutyl azetidine-3-carboxamide | 489.7 | 258 | |
| 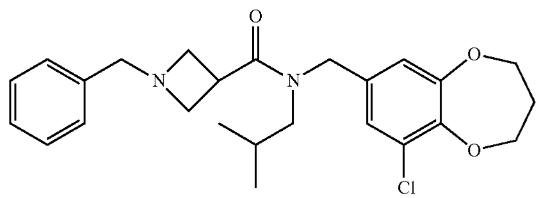 [SMILES: CC(C)CN(Cc1cc(Cl)c2c(c1)OCCCO2)C(=O)C1CN(Cc2ccccc2)C1] | 1-Benzyl-N-(9-chloro-3,4-dihydro-2H-1,5-benzodioxepin-7-ylmethyl)-N-isobutyl azetidine-3-carboxamide | 443.3 | 1190 | |
| 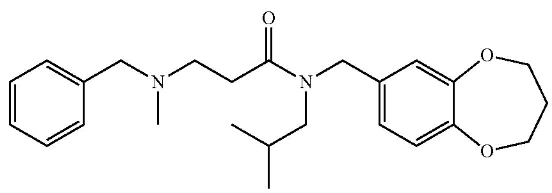 [SMILES: CC(C)CN(Cc1ccc2c(c1)OCCCO2)C(=O)CCN(C)Cc1ccccc1] | 3-(Benzyl(methyl)amino)-N-(3,4-dihydro-2H-1,5-benzodioxepin-7-ylmethyl)-N-isobutylpropanamide | 411.2 | ND | |
| 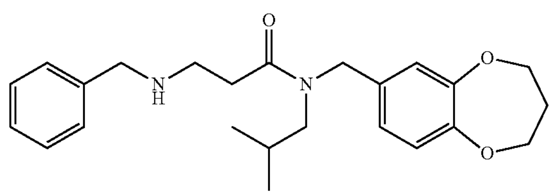 [SMILES: CC(C)CN(Cc1ccc2c(c1)OCCCO2)C(=O)CCNCc1ccccc1] | 3-(Benzylamino)-N-(3,4-dihydro-2H-1,5-benzodioxepin-7-ylmethyl)-N-isobutylpropanamide | 397.2 | 518 | |
| 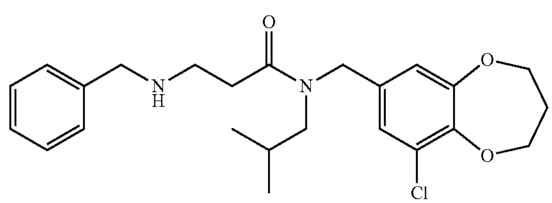 [SMILES: CC(C)CN(Cc1cc(Cl)c2c(c1)OCCCO2)C(=O)CCNCc1ccccc1] | 3-(Benzylamino)-N-(9-chloro-3,4-dihydro-2H-1,5-benzodioxepin-7-ylmethyl)-N-isobutylpropanamide | 431.3 | 344 | |
| 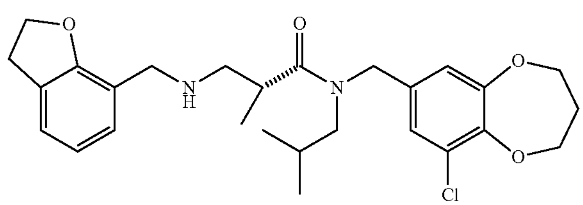 | (−)-(2R)-2-Methyl-3-(2,3-dihydro-1-benzofuran-7-ylmethyl)-amino)-N-(9-chloro-3,4-dihydro-2H-1,5-benzodioxepin-7-ylmethyl)-N-benzodioxepin-7-ylmethyl | 487.3 | 2.38 | 3.78 |
| 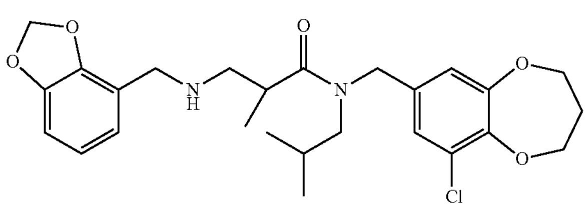 [SMILES: CC(C)CN(Cc1cc(Cl)c2c(c1)OCCCO2)C(=O)C(C)CNCc1cccc2c1OCO2] | (±)-2-Methyl-3-(1,3-(benzodioxol-4-ylmethylamino)-N-(9-chloro-3,4-dihydro-2H-1,5-benzodioxepin-7-ylmethyl)-N-isobutylpropanamide | 589.3 | 4.80 | 44.8 |

-continued

| Structure | Compound Name | Mass Ion (M + 1) | Ki for PKR2 (nM) | Ki for PKR1 (nM) |
|---|---|---|---|---|
| 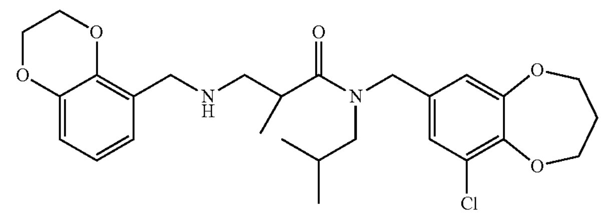 [SMILES: CC(C)CN(Cc1cc(Cl)c2c(c1)OCCCO2)C(=O)C(C)CNCc1cccc2c1OCCO2] | (±)-2-Methyl-3-(2,3-dihydro-1,4-benzodioxin-5-ylmethylamino)-N-(9-chloro-3,4-dihydro-2H-1,5-benzodioxepin-7-ylmethyl)-N-isobutylpropanamide | 503.3 | 6.16 | 58.4 |
| 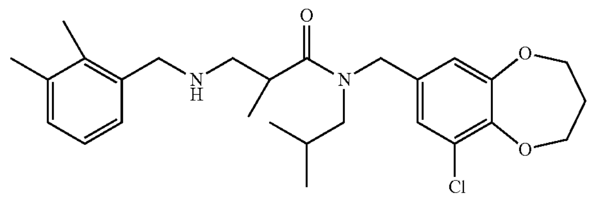 [SMILES: Cc1cccc(CNCC(C)C(=O)N(Cc2cc(Cl)c3c(c2)OCCCO3)CC(C)C)c1C] | (±)-2-Methyl-3-((2,3-dimethyl)benzylamino)-N-(9-chloro-3,4-dihydro-2H-1,5-benzodioxepin-7-ylmethyl)-N-isobutylpropanamide | 473.4 | 8.14 | 13.0 |
| 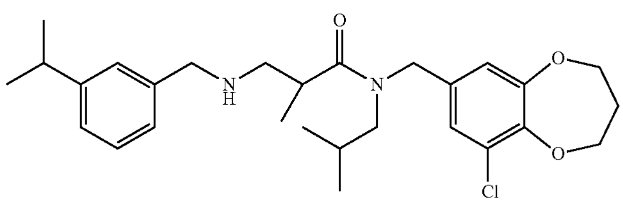 [SMILES: CC(C)CN(Cc1cc(Cl)c2c(c1)OCCCO2)C(=O)C(C)CNCc1cccc(C(C)C)c1] | (±)-2-Methyl-3-((3-isopropyl)benzylamino)-N-(9-chloro-3,4-dihydro-2H-1,5-benzodioxepin-7-ylmethyl)-N-isobutylpropanamide | 499.5 | 177 | 394 |
| 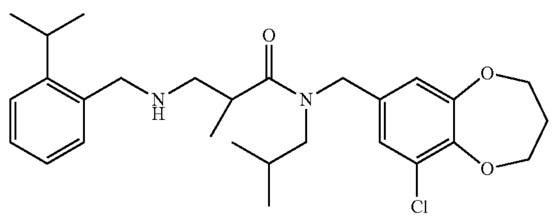 [SMILES: CC(C)CN(Cc1cc(Cl)c2c(c1)OCCCO2)C(=O)C(C)CNCc1ccccc1C(C)C] | (±)-2-Methyl-3-((2-isopropyl)benzylamino)-N-(9-chloro-3,4-dihydro-2H-1,5-benzodioxepin-7-ylmethyl)-N-isobutylpropanamide | 499.5 | 197 | 178 |
| 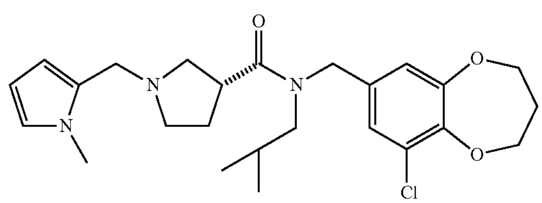 | (−)-(3R)-1-((1-Methyl-1H-pyrrol-2-yl)methyl)-N-(9-chloro-3,4-dihydro-2H-1,5-benzodioxepin-7-ylmethyl)-N-isobutylpyrrolidine-3-carboxamide | 460.2 | 27.3 | |
| 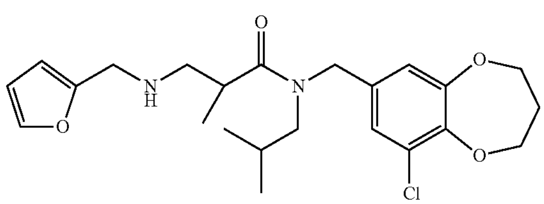 [SMILES: CC(C)CN(Cc1cc(Cl)c2c(c1)OCCCO2)C(=O)C(C)CNCc1ccco1] | (±)-2-Methyl-3-(furan-2-ylmethylamino)-N-(9-chloro-3,4-dihydro-2H-1,5-benzodioxepin-7-ylmethyl)-N-isobutylpropanamide | 435.2 | 130 | 722 |
| 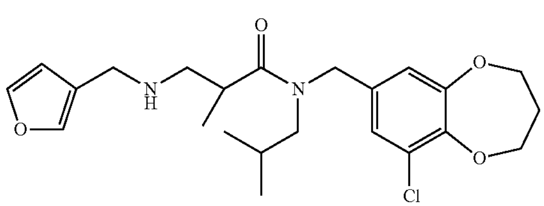 [SMILES: CC(C)CN(Cc1cc(Cl)c2c(c1)OCCCO2)C(=O)C(C)CNCc1ccoc1] | (±)-2-Methyl-3-(furan-3-ylmethylamino)-N-(9-chloro-3,4-dihydro-2H-1,5-benzodioxepin-7-ylmethyl)-N-isobutylpropanamide | 435.2 | 145 | |

| Structure | Compound Name | Mass Ion (M + 1) | Ki for PKR2 (nM) | Ki for PKR1 (nM) |
|---|---|---|---|---|
| 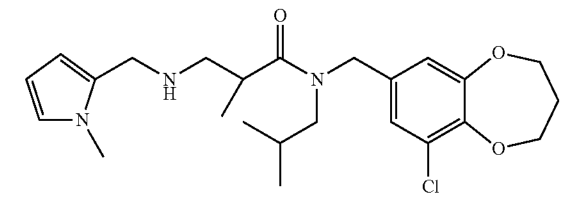 [SMILES: CC(C)CN(Cc1cc(Cl)c2c(c1)OCCCO2)C(=O)C(C)CNCc1cccn1C] | (±)-2-Methyl-3-((1-methyl-1H-pyrrol-2-yl)methylamino)-N-(9-chloro-3,4-dihydro-2H-1,5-benzodioxepin-7-ylmethyl)-N-isobutylpropanamide | 448.2 | 24.3 | 194 |
| 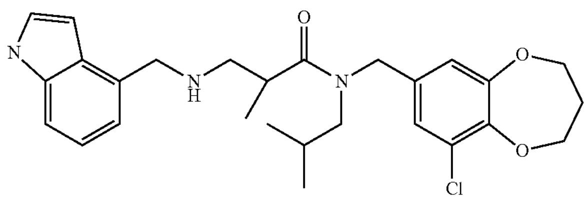 | (±)-2-Methyl-3-(indol-4-ylmethylamino)-N-(9-chloro-3,4-dihydro-2H-1,5-benzodioxepin-7-ylmethyl)-N-isobutylpropanamide | 484.3 | 2.62<br>1.50 | 18.1<br>11.4<br>10.7 |
| 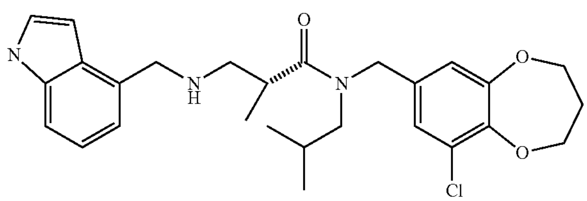 | (−)-(2R)-2-Methyl-3-(indol-4-ylmethylamino)-N-(9-chloro-3,4-dihydro-2H-1,5-benzodioxepin-7-ylmethyl)-N-isobutylpropanamide | 484.3 | 1.43<br>1.6 | 7.18<br>4.08<br>2.38<br>4.24<br>14.9 |
| 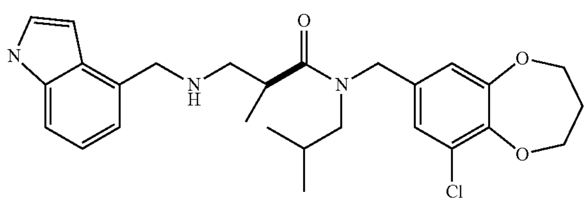 | (+)-(2S)-2-Methyl-3-(indol-4-ylmethylamino)-N-(9-chloro-3,4-dihydro-2H-1,5-benzodioxepin-7-ylmethyl)-N-isobutylpropanamide | 484.3 | 87.8 | 240 |
| 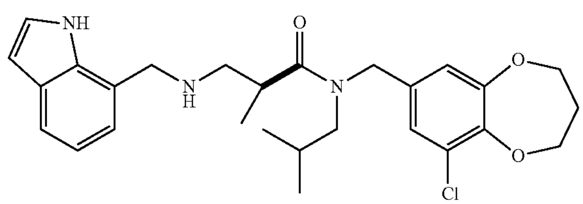 | (+)-(2S)-2-Methyl-3-(indol-7-ylmethylamino)-N-(9-chloro-3,4-dihydro-2H-1,5-benzodioxepin-7-ylmethyl)-N-isobutylpropanamide | 484.3 | 46 | 67.4 |
| 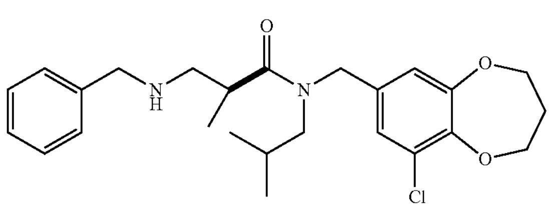 | (+)-(2S)-2-Methyl-3-benzylmethylamino)-N-(9-chloro-3,4-dihydro-2H-1,5-benzodioxepin-7-ylmethyl)-N-isobutylpropanamide | 445.3 | 178 | 1364 |
| 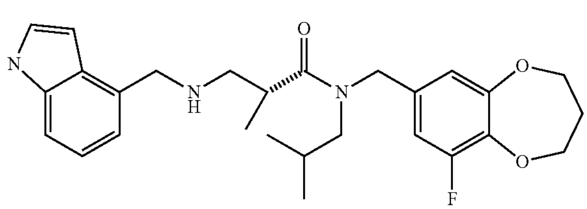 | (−)-(2R)-2-Methyl-3-(indol-4-ylmethylamino)-N-(9-fluoro-3,4-dihydro-2H-1,5-benzodioxepin-7-ylmethyl)-N-isobutylpropanamide | 678.8 | 24.2 | 75.4 |

-continued

| Structure | Compound Name | Mass Ion (M + 1) | Ki for PKR2 (nM) | Ki for PKR1 (nM) |
|---|---|---|---|---|
| 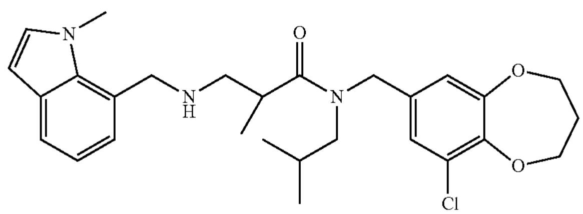 | (±)-2-Methyl-3-(N-methyl-indol-7-ylmethylamino)-N-(9-chloro-3,4-dihydro-2H-1,5-benzodioxepin-7-ylmethyl)-N-isobutylpropanamide | 498.3 | 10.6 | 16.5 |
| 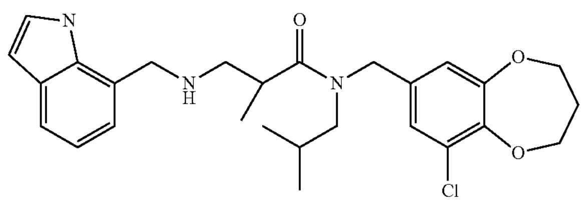 [SMILES: CC(C)CN(Cc1cc(Cl)c2c(c1)OCCCO2)C(=O)C(C)CNCc1cccc2cc[nH]c12] | (±)-2-Methyl-3-(indol-7-ylmethylamino)-N-(9-chloro-3,4-dihydro-2H-1,5-benzodioxepin-7-ylmethyl)-N-isobutylpropanamide | 484.3 | 1.85 | 6.96 4.90 |
| 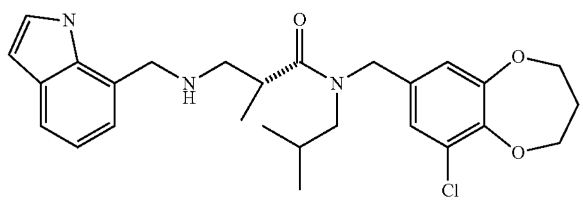 | (−)-(2R)-2-Methyl-3-(indol-7-ylmethylamino)-N-(9-chloro-3,4-dihydro-2H-1,5-benzodioxepin-7-ylmethyl)-N-isobutylpropanamide | 484.3 | 2.87 | 8.12 |
| 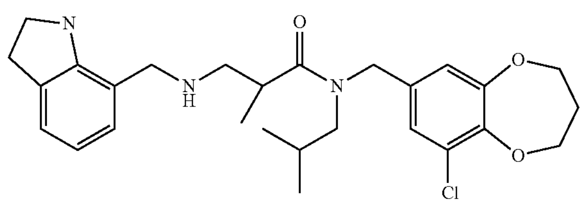 | (±)-2-Methyl-3-(indolin-7-ylmethylamino)-N-(9-chloro-3,4-dihydro-2H-1,5-benzo dioxepin-7-ylmethyl)-N-isobutylpropanamide | 486.3 | 26.1 | 21.2 |
| 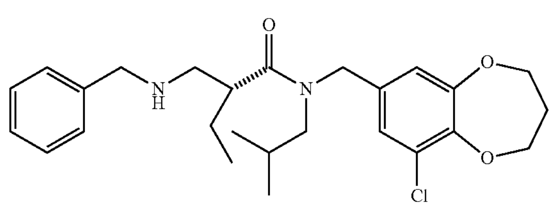 | (−)-(2R)-2-Ethyl-3-(benzylamino)-N-(9-chloro-3,4-dihydro-2H-1,5-benzodioxepin-7-ylmethyl)-N-isobutylpropanamide | 459.2 | 48.8 | 222 |
| 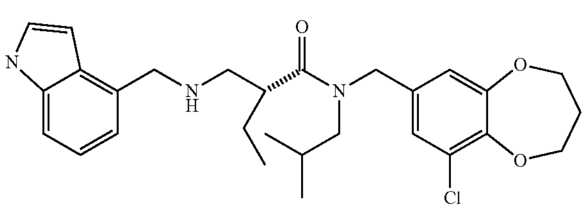 | (−)-(2R)-2-Ethyl-3-(indol-4-ylmethylamino)-N-(9-chloro-3,4-dihydro-2H-1,5-benzodioxepin-7-ylmethyl)-N-isobutylpropanamide | 498.3 | 16.7 | 37.6 |
| 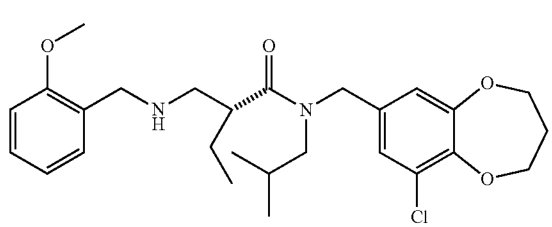 | (−)-(2R)-2-Ethyl-3-(2-methoxybenzylamino)-N-(9-chloro-3,4-dihydro-2H-1,5-benzodioxepin-7-ylmethyl)-N-isobutylpropanamide | 489.3 | 17.8 | 116 |

-continued

| Structure | Compound Name | Mass Ion (M + 1) | Ki for PKR2 (nM) | Ki for PKR1 (nM) |
|---|---|---|---|---|
| 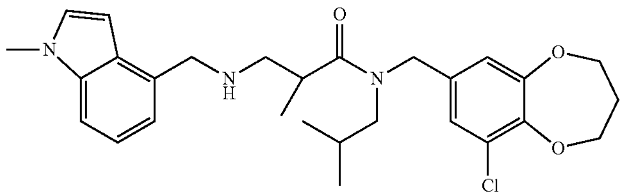 [SMILES: CC(C)CN(Cc1cc(Cl)c2c(c1)OCCCO2)C(=O)C(C)CNCc1cccc2c1ccn2C] | (±)-2-Methyl-3-(N-methyl-indol-4-ylmethylamino)-N-(9-chloro-3,4-dihydro-2H-1,5-benzodioxepin-7-ylmethyl)-N-isobutylpropanamide | 498.3 | 3.96 | 13.3 19.9 |
| 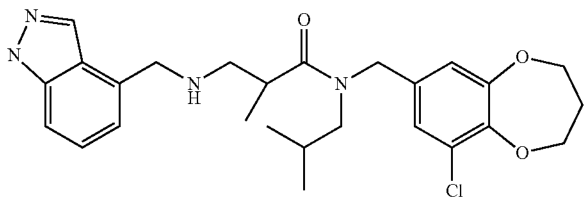 [SMILES: CC(C)CN(Cc1cc(Cl)c2c(c1)OCCCO2)C(=O)C(C)CNCc1cccc2[nH]ncc12] | (±)-2-Methyl-3-(indazol-4-ylmethylamino)-N-(9-chloro-3,4-dihydro-2H-1,5-benzodioxepin-7-ylmethyl)-N-isobutylpropanamide | 485.2 | 61.6 | 145 |
| 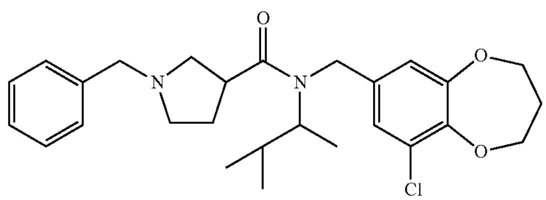 [SMILES: CC(C)C(C)N(Cc1cc(Cl)c2c(c1)OCCCO2)C(=O)C1CCN(Cc2ccccc2)C1] | (±)-N-Benzyl-N-(9-chloro-3,4-dihydro-2H-1,5-benzodioxepin-7-ylmethyl)-N-(1,2-dimethyl)propylpyrrolidine-3-carboxamide | 471.2 | 964 | >10,000 |
| 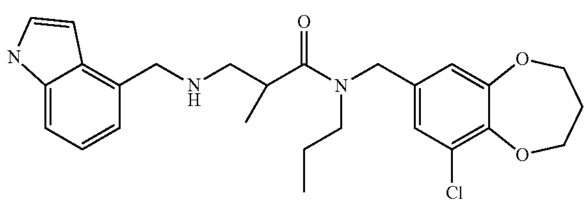 [SMILES: CCCN(Cc1cc(Cl)c2c(c1)OCCCO2)C(=O)C(C)CNCc1cccc2[nH]ccc12] | (±)-2-Methyl-3-(indol-4-ylmethylamino)-N-(9-chloro-3,4-dihydro-2H-1,5-benzodioxepin-7-ylmethyl)-N-propylpanamide | 470.3 | 15.8 | 19.7 35.6 |
| 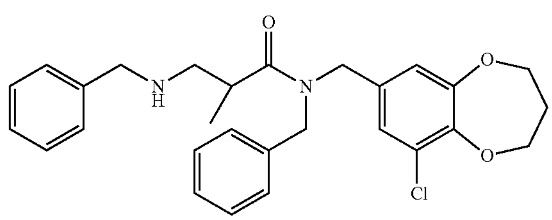 [SMILES: CC(CNCc1ccccc1)C(=O)N(Cc1ccccc1)Cc1cc(Cl)c2c(c1)OCCCO2] | (±)-2-Methyl-3-(benzylamino)-N-(9-chloro-3,4-dihydro-2H-1,5-benzodioxepin-7-ylmethyl)-N-benzylpropanamide | 479.4 | 121 | 992 |
| 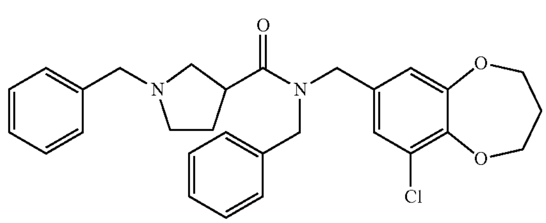 [SMILES: O=C(C1CCN(Cc2ccccc2)C1)N(Cc1ccccc1)Cc1cc(Cl)c2c(c1)OCCCO2] | (±)-2-Benzyl-N-(9-chloro-3,4-dihydro-2H-1,5-benzodioxepin-7-ylmethyl)-N-benzylpyrrolidine-3-carboxamide | 491.2 | 73.0 | 208 |
| 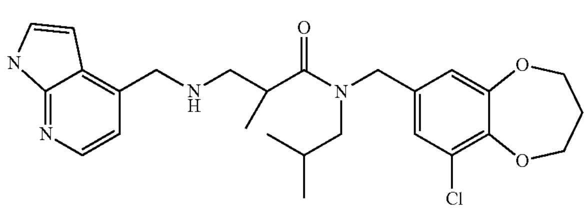 | (±)-2-Methyl-3-(7-Azaindol-4-ylmethylamino)-N-(9-chloro-3,4-dihydro-2H-1,5-benzodioxepin-7-ylmethyl)-N-isobutylpropanamide | 485.3 | 10.8 | 95.8 |

-continued

| Structure | Compound Name | Mass Ion (M + 1) | Ki for PKR2 (nM) | Ki for PKR1 (nM) |
|---|---|---|---|---|
| 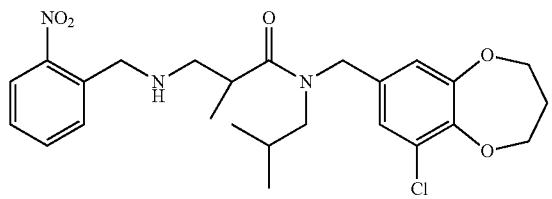 | (±)-2-Methyl-3-((2-nitro)benzylamino-N-(9-chloro-3,4-dihydro-2H-1,5-benzodioxepin-7-ylmethyl)-N-isobutylpropanamide | 490.2 | 54.2 | |
| 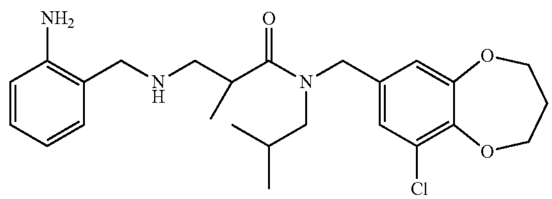 | (±)-2-Methyl-3-((2-amino)benzylamino)-N-(9-chloro-3,4-dihydro-2H-1,5-benzodioxepin-7-ylmethyl)-N-isobutylpropanamide | 460.2 | 15.7 | 248 |
| 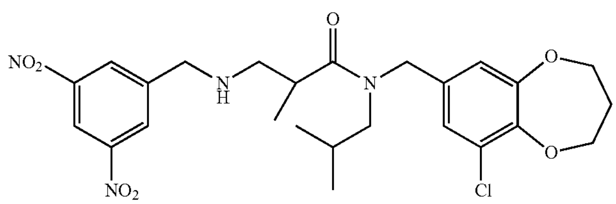 | (±)-2-Methyl-3-((3,5-dinitro)benzylamino)-N-(9-chloro-3,4-dihydro-2H-1,5-benzodioxepin-7-ylmethyl)-N-isobutylpropanamide | 535.2 | 254 | |
| 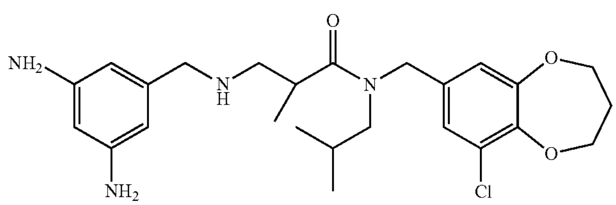 [SMILES: CC(C)CN(Cc1cc(Cl)c2c(c1)OCCCO2)C(=O)C(C)CNCc1cc([N+](=O)[O-])cc([N+](=O)[O-])c1] | (±)-2-Methyl-3-((3,5-diamino)benzylamino)-N-(9-chloro-3,4-dihydro-2H-1,5-benzodioxepin-7-ylmethyl)-N-isobutylpropanamide | 475.2 | 356 | 94.4 |
| 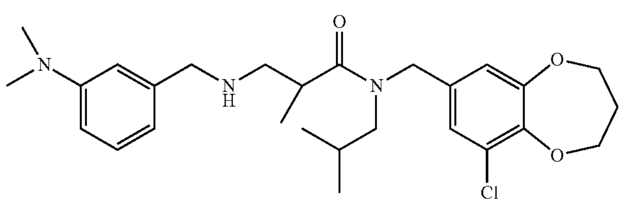 [SMILES: CC(C)CN(Cc1cc(Cl)c2c(c1)OCCCO2)C(=O)C(C)CNCc1cccc(N(C)C)c1] | (±)-2-Methyl-3-((3-dimethylamino)benzylamino)-N-(9-chloro-3,4-dihydro-2H-1,5-benzodioxepin-7-ylmethyl)-N-isobutylpropanamide | 488.5 | 34.8 | 98.8 |
| 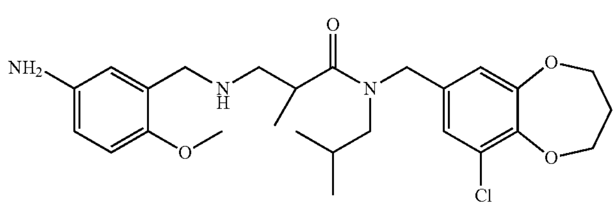 | (±)-2-Methyl-3-((3-amino-5-methoxy)benzylamino)-N-(9-chloro-3,4-dihydro-2H-1,5-benzodioxepin-7-ylmethyl)-N-isobutylpropanamide | 490.5 | 62.2 | 2060 |
| 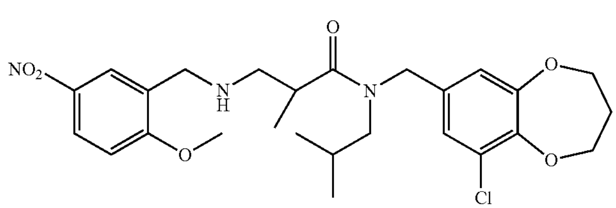 [SMILES: COc1ccc([N+](=O)[O-])cc1CNCC(C)C(=O)N(Cc1cc(Cl)c2c(c1)OCCCO2)CC(C)C] | (±)-2-Methyl-3-((3-nitro-5-methoxy)benzylamino)-N-(9-chloro-3,4-dihydro-2H-1,5-benzodioxepin-7-ylmethyl)-N-isobutylpropanamide | 520.5 | 200 | |

-continued

| Structure | Compound Name | Mass Ion (M + 1) | Ki for PKR2 (nM) | Ki for PKR1 (nM) |
|---|---|---|---|---|
| 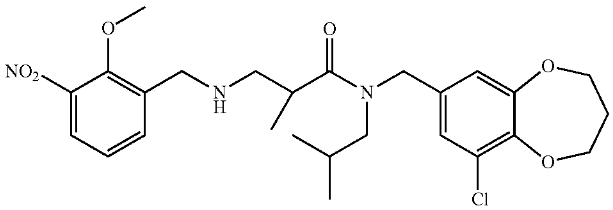 | (±)-2-Methyl-3-((2-methoxy-3-nitro)benzylamino)-N-(9-chloro-3,4-dihydro-2H-1,5-benzodioxepin-7-ylmethyl)-N-isobutylpropanamide | 520.5 | 28.1 | |
| 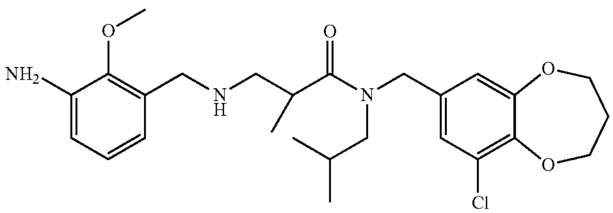 [SMILES: COc1c(CNCC(C)C(=O)N(Cc2cc(Cl)c3c(c2)OCCCO3)CC(C)C)cccc1[N+](=O)[O-]] | (±)-2-Methyl-3-((2-methoxy-3-amino)benzylamino)-N-(9-chloro-3,4-dihydro-2H-1,5-benzodioxepin-7-ylmethyl)-N-isobutylpropanamide | 490.5 | 92.4 | 96.4 |
| 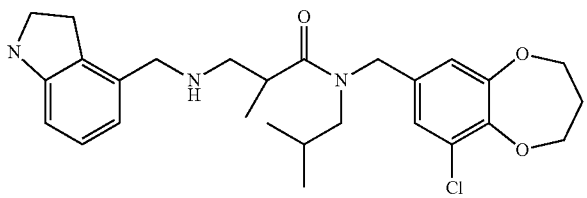 [SMILES: CC(C)CN(Cc1cc(Cl)c2c(c1)OCCCO2)C(=O)C(C)CNCc1cccc2c1CCN2] | (±)-(3R)-2-Methyl-3-(indolin-4-ylmethylamino)-N-(9-chloro-3,4-dihydro-2H-1,5-benzodioxepin-7-ylmethyl)-N-isobutylpropanamide | 486.3 | 1.53 | 10.3 |
| 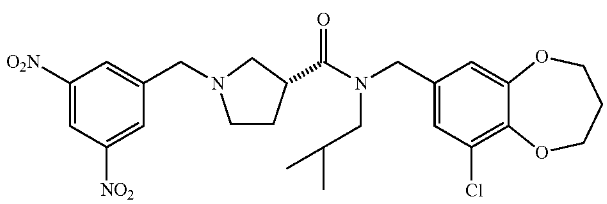 | (−)-(3R)-1-(3,5-Dinitrobenzyl)-N-(9-chloro-3,4-dihydro-2H-1,5-benzodioxepin-7-ylmethyl)-N-isobutylpyrrolidine-3-carboxamide | 547.2 | 1508 | |
| 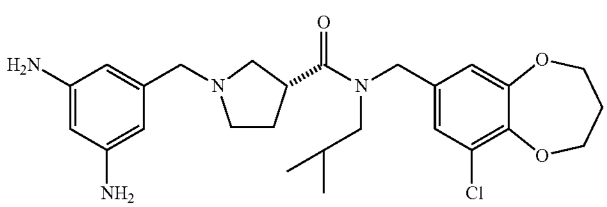 | (−)-(3R)-1-(3,5-Diaminobenzyl)-N-(9-chloro-3,4-dihydro-2H-1,5-benzodioxepin-7-ylmethyl)-N-isobutylpyrrolidine-3-carboxamide | 487.3 | 670 | 1560 |
| 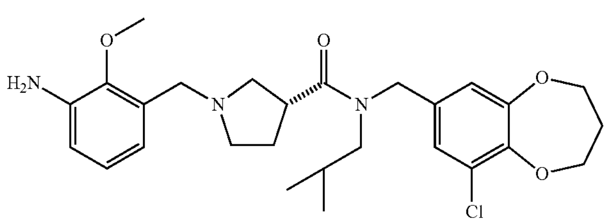 | (−)-(3R)-1-(2-Methoxy-3-aminobenzyl)-N-(9-chloro-3,4-dihydro-2H-1,5-benzodioxepin-7-ylmethyl)-N-isobutylpyrrolidine-3-carboxamide | 502.5 | 36.0 | 3600 |
| 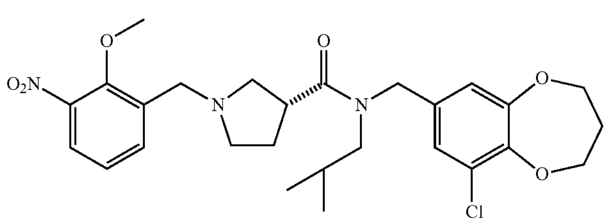 | (−)-(3R)-1-(2-Methoxy-3-nitrobenzyl)-N-(9-chloro-3,4-dihydro-2H-1,5-benzodioxepin-7-ylmethyl)-N-isobutylpyrrolidine-3-carboxamide | 532.5 | 69.0 | |

-continued

| Structure | Compound Name | Mass Ion (M + 1) | Ki for PKR2 (nM) | Ki for PKR1 (nM) |
|---|---|---|---|---|
| 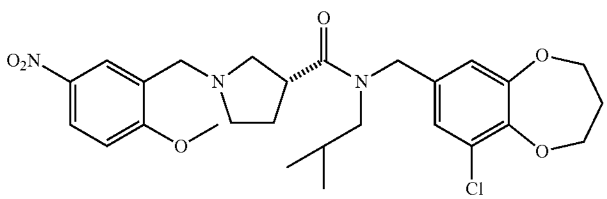 | (−)-(3R)-1-(2-Methoxy-5-nitrobenzyl)-N-(9-chloro-3,4-dihydro-2H-1,5-benzodioxepin-7-ylmethyl)-N-isobutylpyrrolidine-3-carboxamide | 532.5 | 292 | |
| 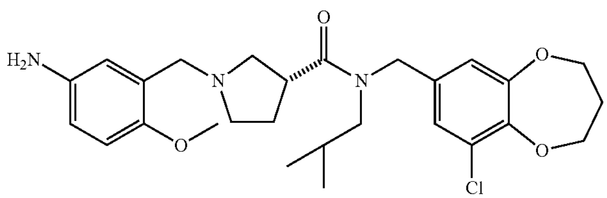 | (−)-(3R)-1-(2-Methoxy-5-aminobenzyl)-N-(9-chloro-3,4-dihydro-2H-1,5-benzodioxepin-7-ylmethyl)-N-isobutylpyrrolidine-3-carboxamide | 502.5 | 112 | 442 |
| 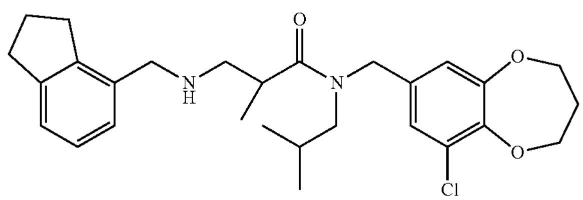 [SMILES: CC(C)CN(Cc1cc(Cl)c2c(c1)OCCCO2)C(=O)C(C)CNCc1cccc2c1CCC2] | (±)-2-Methyl-3-(indan-4-ylmethylamino)-N-(9-chloro-3,4-dihydro-2H-1,5-benzodioxepin-7-ylmethyl)-N-isobutylpropanamide | 485.3 | 9.86 | 40.4 |
| 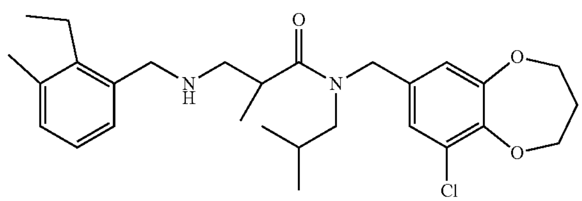 [SMILES: CCc1c(C)cccc1CNCC(C)C(=O)N(Cc1cc(Cl)c2c(c1)OCCCO2)CC(C)C] | (±)-2-Methyl-3-((2-ethyl-3-methyl)benzylamino)-N-(9-chloro-3,4-dihydro-2H-1,5-benzodioxepin-7-ylmethyl)-N-isobutylpropanamide | 487.3 | 40.8 | 226 |
| 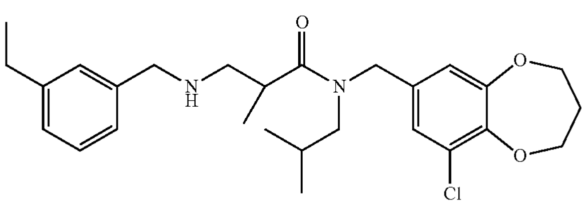 [SMILES: CCc1cccc(CNCC(C)C(=O)N(Cc2cc(Cl)c3c(c2)OCCCO3)CC(C)C)c1] | (±)-2-Methyl-3-((3-ethyl-benzylamino)-N-(9-chloro-3,4-dihydro-2H-1,5-benzodioxepin-7-ylmethyl)-N-isobutylpropanamide | 473.3 | 48.0 | 197 |
| 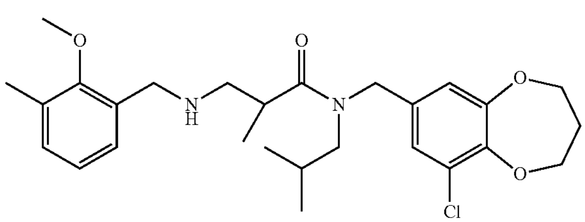 [SMILES: COc1c(C)cccc1CNCC(C)C(=O)N(Cc1cc(Cl)c2c(c1)OCCCO2)CC(C)C] | (±)-2-Methyl-3-((2-methoxy-3-methyl)benzylamino)-N-(9-chloro-3,4-dihydro-2H-1,5-benzodioxepin-7-ylmethyl)-N-isobutylpropanamide | 489.3 | 23.8 | 104 |
| 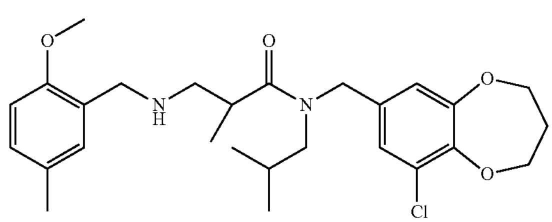 | (±)-2-Methyl-3-((2-methoxy-5-methyl)benzylamino)-N-(9-chloro-3,4-dihydro-2H-1,5-benzodioxepin-7-ylmethyl)-N-isobutylpropanamide | 489.3 | 11.0 | 53.2 |

| Structure | Compound Name | Mass Ion (M + 1) | Ki for PKR2 (nM) | Ki for PKR1 (nM) |
|---|---|---|---|---|
| 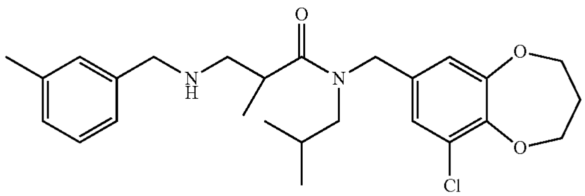 [SMILES: Cc1cccc(CNCC(C)C(=O)N(Cc2cc(Cl)c3c(c2)OCCCO3)CC(C)C)c1] | (±)-2-Methyl-3-((3-methyl)benzylamino)-N-(9-chloro-3,4-dihydro-2H-1,5-benzodioxepin-7-ylmethyl)-N-isobutylpropanamide | 459.4 | 9.16 | 44.2 |
| 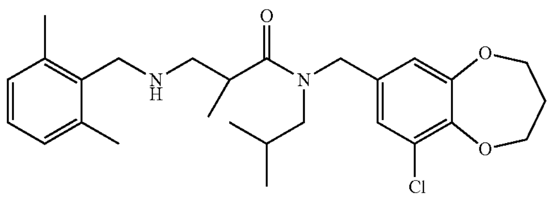 [SMILES: Cc1cccc(C)c1CNCC(C)C(=O)N(Cc1cc(Cl)c2c(c1)OCCCO2)CC(C)C] | (±)-2-Methyl-3-((2,6-dimethyl)benzylamino)-N-(9-chloro-3,4-dihydro-2H-1,5-benzodioxepin-7-ylmethyl)-N-isobutylpropanamide | 473.4 | 18.9 | 44.0 |
| 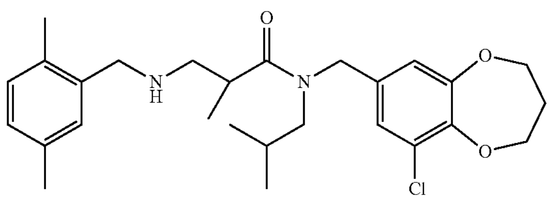 | (±)-2-Methyl-3-((2,5-dimethyl)benzylamino)-N-(9-chloro-3,4-dihydro-2H-1,5-benzodioxepin-7-ylmethyl)-N-isobutylpropanamide | 473.4 | 10.7 | 37.4 |
| 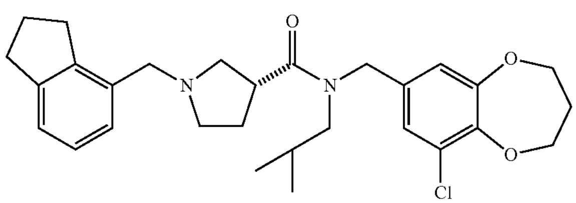 | (−)-(3R)-1-(Indan-4-ylmethyl)-N-(9-chloro-3,4-dihydro-2H-1,5-benzodioxepin-7-ylmethyl)-N-isobutylpyrrolidine-3-carboxamide | 497.2 | 20.4 | 60.2 |
| 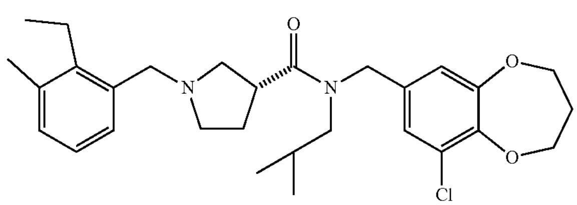 | (−)-(3R)-1-(2-Ethyl-3-methylbenzyl)-N-(9-chloro-3,4-dihydro-2H-1,5-benzodioxepin-7-ylmethyl)-N-isobutylpyrrolidine-3-carboxamide | 499.3 | 44.0 | 226 |
| 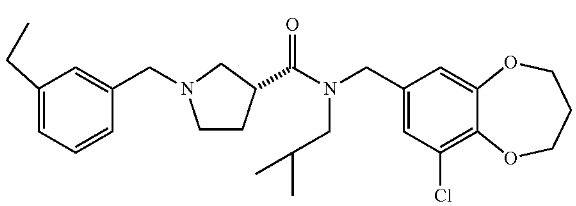 | (−)-(3R)-1-(3-Ethylbenzyl)-N-(9-chloro-3,4-dihydro-2H-1,5-benzodioxepin-7-ylmethyl)-N-isobutylpyrrolidine-3-carboxamide | 485.3 | 30.2 | 88.8 |
| | (−)-(3R)-1-(2-Methoxy-3-methylbenzyl)-N-(9-chloro-3,4-dihydro-2H-1,5-benzodioxepin-7-ylmethyl)-N-isobutylpyrrolidine-3-carboxamide | 501.3 | 30.8 | 74.5 |

-continued

| Structure | Compound Name | Mass Ion (M + 1) | Ki for PKR2 (nM) | Ki for PKR1 (nM) |
|---|---|---|---|---|
| 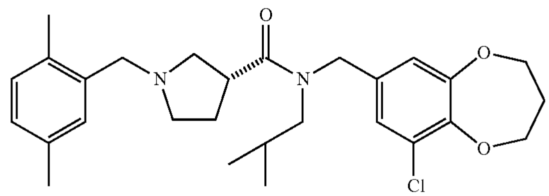 | (−)-(3R)-1-(2,5-Dimethylbenzyl)-N-(9-chloro-3,4-dihydro-2H-1,5-benzodioxepin-7-ylmethyl)-N-isobutylpyrrolidine-3-carboxamide | 485.2 | 4.36 | 12.8 |
| 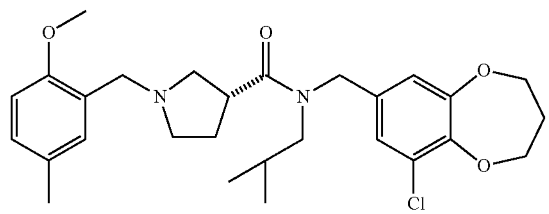 | (−)-(3R)-1-(2-Methoxy-5-methyl-benzyl)-N-(9-chloro-3,4-dihydro-2H-1,5-benzodioxepin-7-ylmethyl)-N-isobutylpyrrolidine-3-carboxamide | 501.3 | 32.4 | 117 |
| 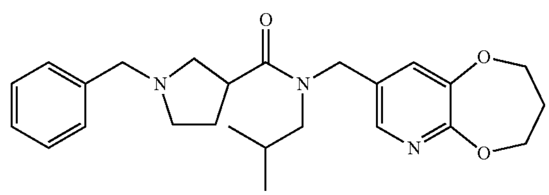 [SMILES: CC(C)CN(Cc1cnc2c(c1)OCCCO2)C(=O)C1CCN(Cc2ccccc2)C1] | (±)-1-Benzyl-N-(3,4-dihydro-2H-1,5-dioxepino-[2,3-b]pyridin-8-ylmethyl)-N-isobutylpyrrolidine-3-carboxamide | 424.3 | 168 | 200 |
| 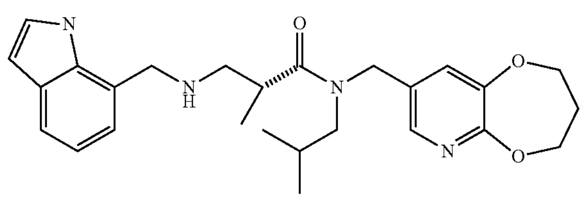 | (−)-(2R)-2-Methyl-3-(indol-7-ylmethylamino)-N-(3,4-dihydro-2H-1,5-dioxepino-[2,3-b]pyridin-8-ylmethyl)-N-isobutylpropanamide | 451.3 | 1.39 | 6.68 |
| 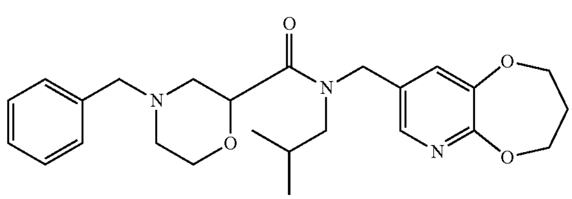 [SMILES: CC(C)CN(Cc1cnc2c(c1)OCCCO2)C(=O)C1CN(Cc2ccccc2)CCO1] | (±)-4-Benzyl-N-(3,4-dihydro-2H-1,5-dioxepino-[2,3-b]pyridin-8-ylmethyl)-N-isobutylmorpholine-2-carboxamide | 440.3 | 113 | 296 |
| 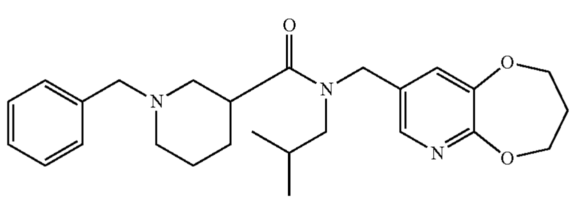 [SMILES: CC(C)CN(Cc1cnc2c(c1)OCCCO2)C(=O)C1CCCN(Cc2ccccc2)C1] | (±)-1-Benzyl-N-(3,4-dihydro-2H-1,5-dioxepino-[2,3-b]pyridin-8-ylmethyl)-N-isobutylpiperidine-3-carboxamide | 438.3 | 88.2 | 708 |
| 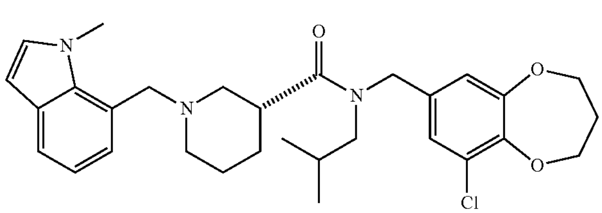 | (−)-(3R)-1-(N-methyl-indol-7-ylmethyl)-N-(9-chloro-3,4-dihydro-2H-1,5-benzodioxepin-7-ylmethyl)-N-isobutylpiperidine-3-carboxamide | 524.3 | 16.0 | 26.6 |

-continued

| Structure | Compound Name | Mass Ion (M + 1) | Ki for PKR2 (nM) | Ki for PKR1 (nM) |
|---|---|---|---|---|
| 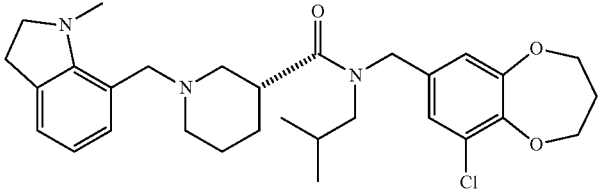 | (−)-(3R)-1-(N-methyl-indolin-7-ylmethyl)-N-(9-chloro-3,4-dihydro-2H-1,5-benzodioxepin-7-ylmethyl)-N-isobutylpiperidine-3-carboxamide | 526.3 | | 87.3 |
| 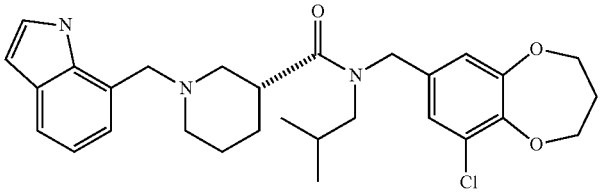 | (−)-(3R)-1-(Indol-7-ylmethyl)-N-(9-chloro-3,4-dihydro-2H-1,5-benzodioxepin-7-ylmethyl)-N-isobutylpiperidine-3-carboxamide | 510.4 | 8.9 | 17.4 |
| 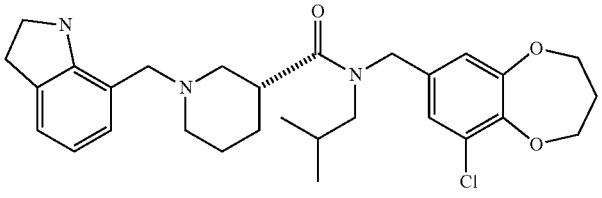 | (−)-(3R)-1-(Indolin-7-ylmethyl)-N-(9-chloro-3,4-dihydro-2H-1,5-benzodioxepin-7-ylmethyl)-N-isobutylpiperidine-3-carboxamide | 512.4 | 2.62 | 3.29 |
| 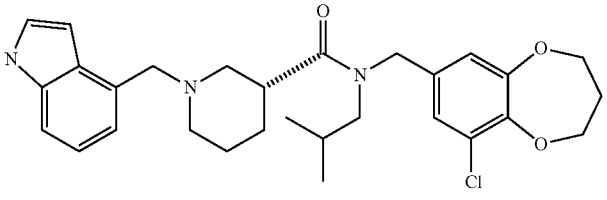 | (−)-(3R)-1-(Indol-4-ylmethyl)-N-(9-chloro-3,4-dihydro-2H-1,5-benzodioxepin-7-ylmethyl)-N-isobutylpiperidine-3-carboxamide | 510.4 | 3.76 | 38.0 |
| 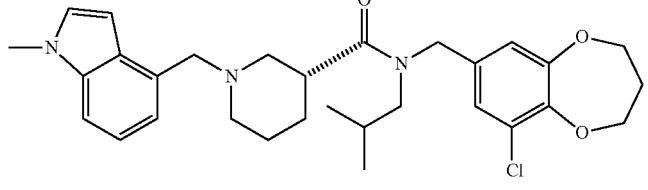 | (−)-(3R)-1-(N-methyl-indol-4-ylmethyl)-N-(9-chloro-3,4-dihydro-2H-1,5-benzodioxepin-7-ylmethyl)-N-isobutylpiperidine-3-carboxamide | 524.3 | 1.24 | 3.74 4.26 |
| 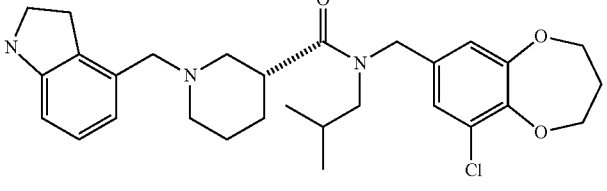 | (−)-(3R)-1-(Indolin-4-ylmethyl)-N-(9-chloro-3,4-dihydro-2H-1,5-benzodioxepin-7-ylmethyl)-N-isobutylpiperidine-3-carboxamide | 512.4 | 2.22 | 6.0 |
| 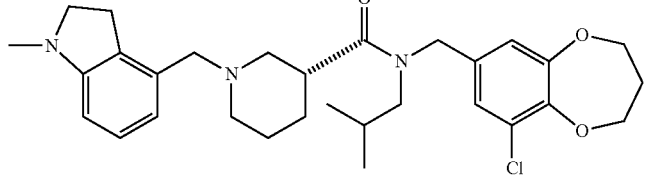 | (−)-(3R)-1-(N-methyl-indolin-4-ylmethyl)-N-(9-chloro-3,4-dihydro-2H-1,5-benzodioxepin-7-ylmethyl)-N-isobutylpiperidine-3-carboxamide | 526.4 | 9.36 | 15.8 |

-continued

| Structure | Compound Name | Mass Ion (M + 1) | Ki for PKR2 (nM) | Ki for PKR1 (nM) |
|---|---|---|---|---|
| 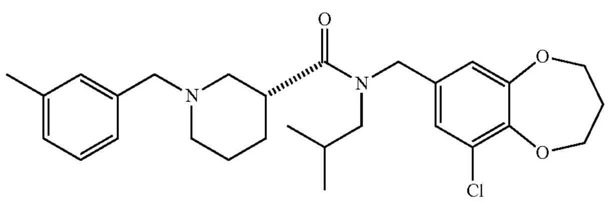 | (−)-(3R)-1-(3-Methylbenzyl)-N-(9-chloro-3,4-dihydro-2H-1,5-benzodioxepin-7-ylmethyl)-N-isobutylpiperidine-3-carboxamide | 485.4 | 11.5 | 29.4 |
| 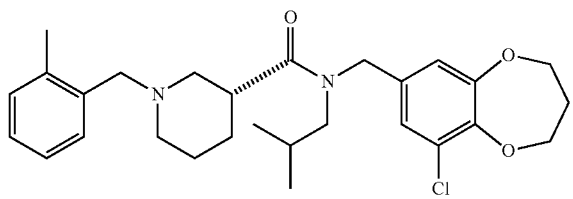 | (−)-(3R)-1-(2-Methylbenzyl)-N-(9-chloro-3,4-dihydro-2H-1,5-benzodioxepin-7-ylmethyl)-N-isobutylpiperidine-3-carboxamide | 485.4 | 12.3 | 29.2 |
| 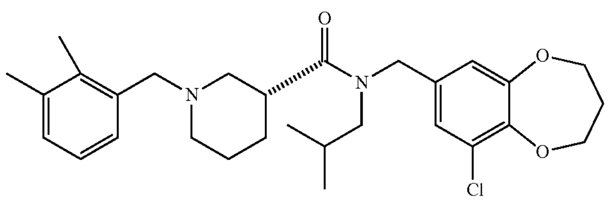 | (−)-(3R)-1-(2,3-Dimethylbenzyl)-N-(9-chloro-3,4-dihydro-2H-1,5-benzodioxepin-7-ylmethyl)-N-isobutylpiperidine-3-carboxamide | 499.4 | 6.54 13.8 | 20.2 |
| 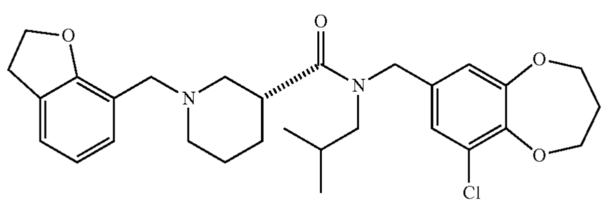 | (−)-(3R)-1-(2,3-Dihydro-1-benzofuran-7-ylmethyl)-N-(9-chloro-3,4-dihydro-2H-1,5-benzodioxepin-7-ylmethyl)-N-isobutylpiperidine-3-carboxamide | 513.3 | 21.4 | 29.0 |
| 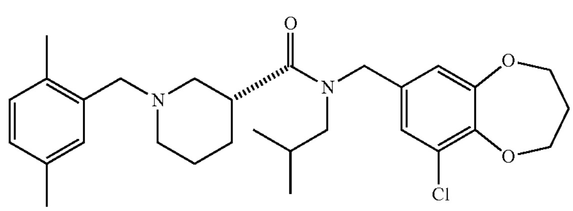 | (−)-(3R)-1-(2,5-Dimethylbenzyl)-N-(9-chloro-3,4-dihydro-2H-1,5-benzodioxepin-7-ylmethyl)-N-isobutylpiperidine-3-carboxamide | 499.4 | 6.54 | 64.2 |
| 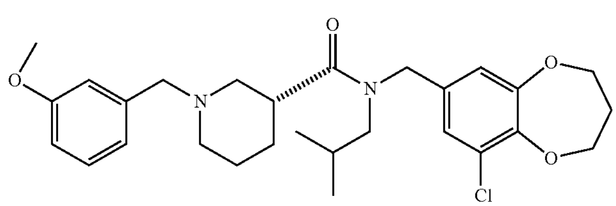 | (−)-(3R)-1-(3-Methoxybenzyl)-N-(9-chloro-3,4-dihydro-2H-1,5-benzodioxepin-7-ylmethyl)-N-isobutylpiperidine-3-carboxamide | 501.4 | 3.68 | 23.4 |
| 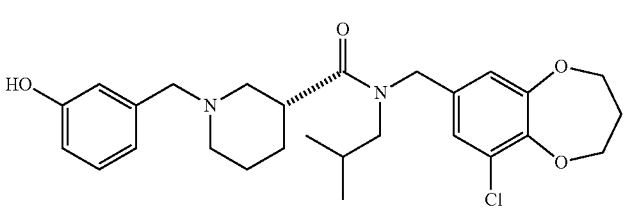 | (−)-(3R)-1-(3-Hydroxybenzyl)-N-(9-chloro-3,4-dihydro-2H-1,5-benzodioxepin-7-ylmethyl)-N-isobutylpiperidine-3-carboxamide | 487.4 | 3.02 | 19.1 |

-continued

| Structure | Compound Name | Mass Ion (M + 1) | Ki for PKR2 (nM) | Ki for PKR1 (nM) |
|---|---|---|---|---|
| 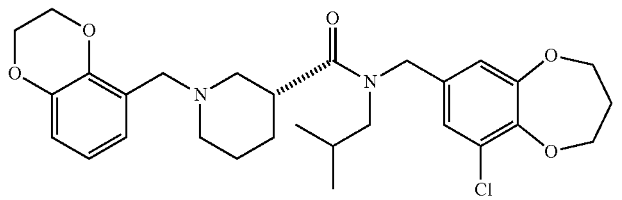 | (−)-(3R)-1-(2,3-Dihydro-1,4-benzodioxin-5-ylmethyl)-N-(9-chloro-3,4-dihydro-2H-1,5-benzodioxepin-7-ylmethyl)-N-isobutylpiperidine-3-carboxamide | 529.4 | 13.9 | 52.0 |
| 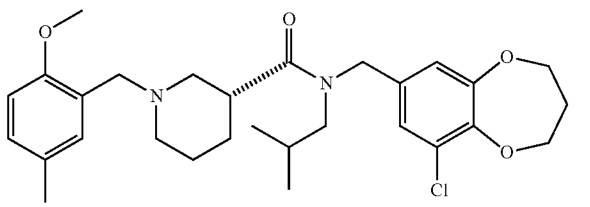 | (−)-(3R)-1-(2-Methoxy-5-methylbenzyl)-N-(9-chloro-3,4-dihydro-2H-1,5-benzodioxepin-7-ylmethyl)-N-isobutylpiperidine-3-carboxamide | 515.3 | 8.94 | 47.4 |
| 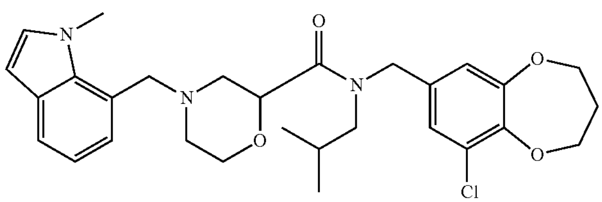 | (±)-4-(N-methyl-indol-7-ylmethyl)-N-(9-chloro-3,4-dihydro-2H-1,5-benzodioxepin-7-ylmethyl)-N-isobutylmorpholine-2-carboxamide | 526.3 | 5.42 | 24.4 |
| 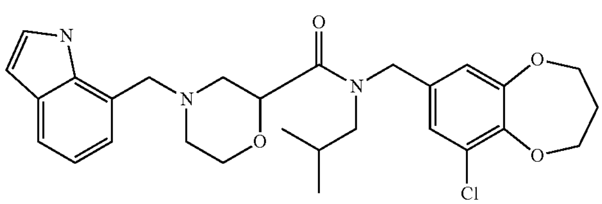 | (±)-4-(Indol-7-ylmethyl)-N-(9-chloro-3,4-dihydro-2H-1,5-benzodioxepin-7-ylmethyl)-N-isobutylmorpholine-2-carboxamide | 512.4 | 3.30 | 5.40 1.13 |
| 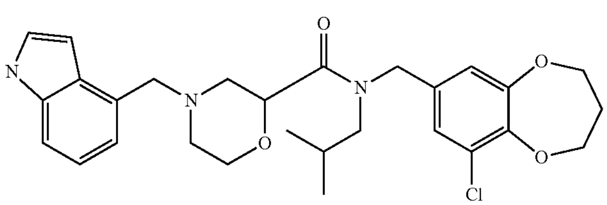 | (±)-4-(Indol-4-ylmethyl)-N-(9-chloro-3,4-dihydro-2H-1,5-benzodioxepin-7-ylmethyl)-N-isobutylmorpholine-2-carboxamide | 512.4 | 2.60 | 17.2 |
| 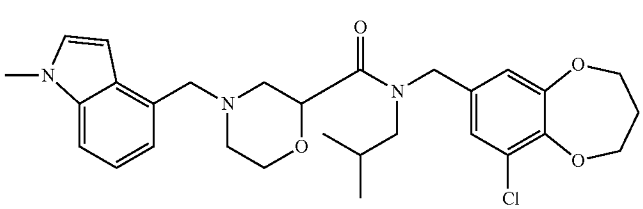 | (±)-4-(N-methyl-indol-4-ylmethyl)-N-(9-chloro-3,4-dihydro-2H-1,5-benzodioxepin-7-ylmethyl)-N-isobutylmorpholine-2-carboxamide | 526.3 | 8.24 | 12.5 |
| 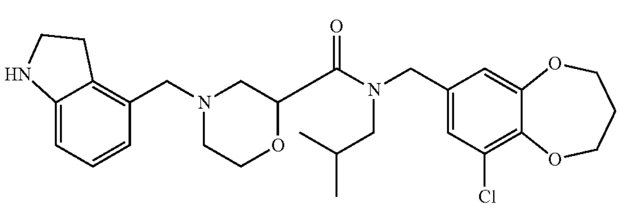 [SMILES: CC(C)CN(Cc1cc(Cl)c2c(c1)OCCCO2)C(=O)C1CN(Cc2cccc3c2CCN3)CCO1] | (±)-4-(Indolin-4-ylmethyl)-N-(9-chloro-3,4-dihydro-2H-1,5-benzodioxepin-7-ylmethyl)-N-isobutylmorpholine-2-carboxamide | 514.4 | 2.64 | 4.80 |

-continued

| Structure | Compound Name | Mass Ion (M + 1) | Ki for PKR2 (nM) | Ki for PKR1 (nM) |
|---|---|---|---|---|
| 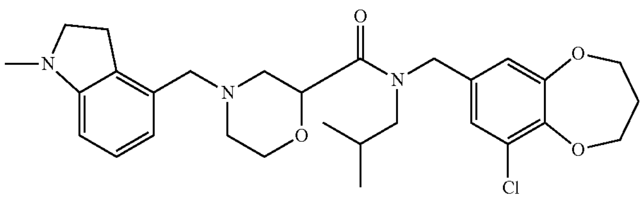 [SMILES: CC(C)CN(Cc1cc(Cl)c2c(c1)OCCCO2)C(=O)C1CN(Cc2cccc3c2CCN3C)CCO1] | (±)-4-(N-methyl-indolin-4-ylmethyl)-N-(9-chloro-3,4-dihydro-2H-1,5-benzodioxepin-7-ylmethyl)-N-isobutylmorpholine-2-carboxamide | 528 | 14.8 | 30.6 |
| 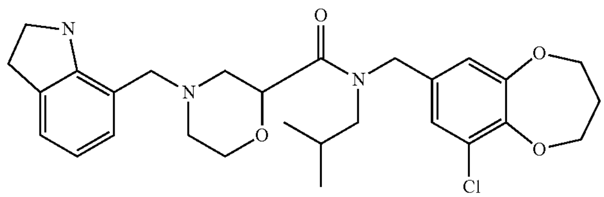 [SMILES: CC(C)CN(Cc1cc(Cl)c2c(c1)OCCCO2)C(=O)C1CN(Cc2cccc3c2NCC3)CCO1] | (±)-4-(Indolin-7-ylmethyl)-N-(9-chloro-3,4-dihydro-2H-1,5-benzodioxepin-7-ylmethyl)-N-isobutylmorpholine-2-carboxamide | 514 | 4.77 | 20.4 |
| 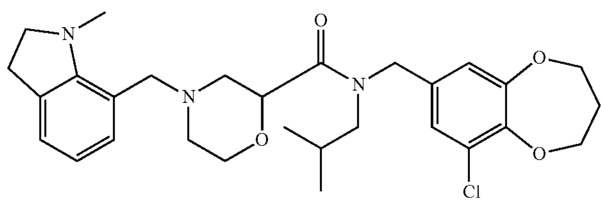 | (±)-4-(N-methyl-indolin-7-ylmethyl)-N-(9-chloro-3,4-dihydro-2H-1,5-benzodioxepin-7-ylmethyl)-N-isobutylmorpholine-2-carboxamide | 528 | 14.2 | 24.8 |
| 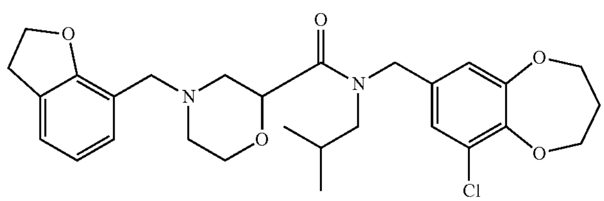 [SMILES: CC(C)CN(Cc1cc(Cl)c2c(c1)OCCCO2)C(=O)C1CN(Cc2cccc3c2OCC3)CCO1] | (±)-4-(2,3-Dihydro-1-benzofuran-7-ylmethyl)-N-(9-chloro-3,4-dihydro-2H-1,5-benzodioxepin-7-ylmethyl)-N-isobutylmorpholine-2-carboxamide | 515.3 | 3.1 | 5.46 |
| 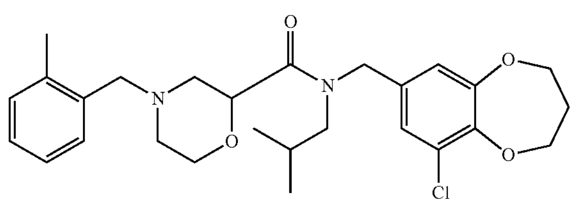 [SMILES: Cc1ccccc1CN1CCOC(C(=O)N(Cc2cc(Cl)c3c(c2)OCCCO3)CC(C)C)C1] | (±)-4-(2-Methylbenzyl)-N-(9-chloro-3,4-dihydro-2H-1,5-benzodioxepin-7-ylmethyl)-N-isobutylmorpholine-2-carboxamide | 487.2 | 40.3 | 37.4 |
| 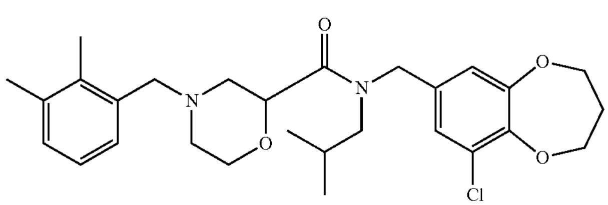 [SMILES: Cc1cccc(CN2CCOC(C(=O)N(Cc3cc(Cl)c4c(c3)OCCCO4)CC(C)C)C2)c1C] | (±)-4-(2,3-Dimethylbenzyl)-N-(9-chloro-3,4-dihydro-2H-1,5-benzodioxepin-7-ylmethyl)-N-isobutylmorpholine-2-carboxamide | 501.3 | 45.0 | 86.6 |
| 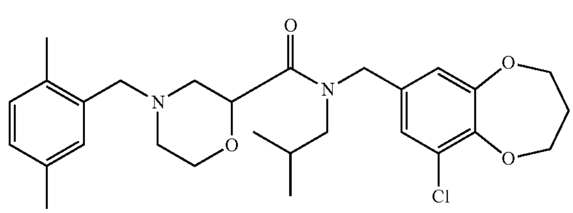 [SMILES: Cc1ccc(C)c(CN2CCOC(C(=O)N(Cc3cc(Cl)c4c(c3)OCCCO4)CC(C)C)C2)c1] | (±)-4-(2,5-Dimethylbenzyl)-N-(9-chloro-3,4-dihydro-2H-1,5-benzodioxepin-7-ylmethyl)-N-isobutylmorpholine-2-carboxamide | 501.3 | 43.8 | 83.0 |

-continued

| Structure | Compound Name | Mass Ion (M + 1) | Ki for PKR2 (nM) | Ki for PKR1 (nM) |
|---|---|---|---|---|
| 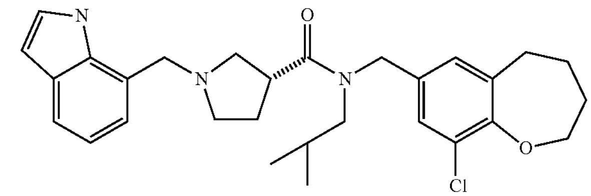 | (−)-(3R)-1-(Indol-7-ylmethyl)-N-(9-chloro-2,3,4,5-tetrahydro-1-benzoxepin-7-ylmethyl)-N-isobutylpyrrolidine-3-carboxamide | 494.3 | 111 | 15.4 |
| 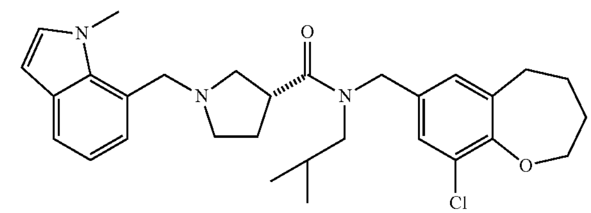 | (−)-(3R)-1-(N-methyl-indol-7-ylmethyl)-N-(9-chloro-2,3,4,5-tetrahydro-1-benzoxepin-7-ylmethyl)-N-isobutylpyrrolidine-3-carboxamide | 508.3 | 16.0 | 18.5 |
| 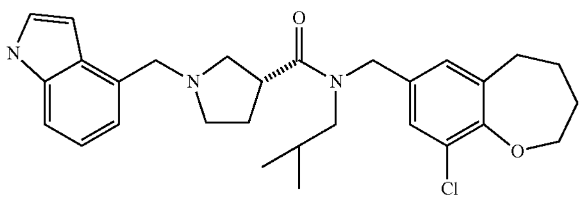 | (−)-(3R)-1-(Indol-4-ylmethyl)-N-(9-chloro-2,3,4,5-tetrahydro-1-benzoxepin-7-ylmethyl)-N-isobutylpyrrolidine-3-carboxamide | 494.3 | 11.2 | 55.8 |
| 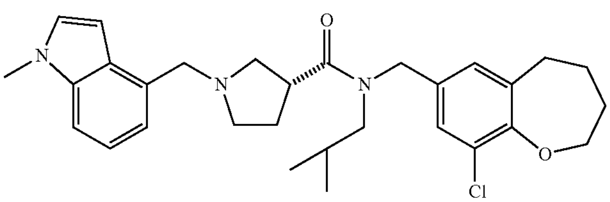 | (−)-(3R)-1-(N-methyl-indol-4-ylmethyl)-N-(9-chloro-2,3,4,5-tetrahydro-1-benzoxepin-7-ylmethyl)-N-isobutylpyrrolidine-3-carboxamide | 508.3 | 8.22 | 11.6 |
| 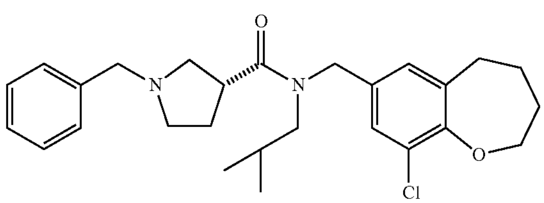 | (−)-(3R)-1-Benzyl-N-(9-chloro-2,3,4,5-tetrahydro-1-benzoxepin-7-ylmethyl)-N-isobutylpyrrolidine-3-carboxamide | 455.2 | 65.2 | 65.5 |
| 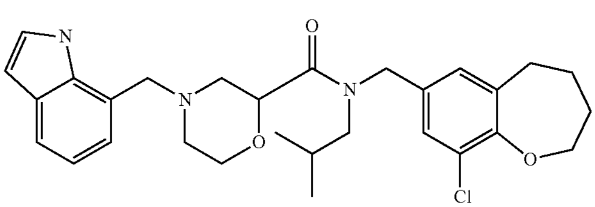 [SMILES: CC(C)CN(Cc1cc(Cl)c2c(c1)CCCCO2)C(=O)C1CN(Cc2cccc3cc[nH]c23)CCO1] | (±)-(3R)-4-(Indol-7-ylmethyl)-N-(9-chloro-2,3,4,5-tetrahydro-1-benzoxepin-7-ylmethyl)-N-isobutylpiperidine-2-carboxamide | 510.3 | 1.94 | 4.02 |
| 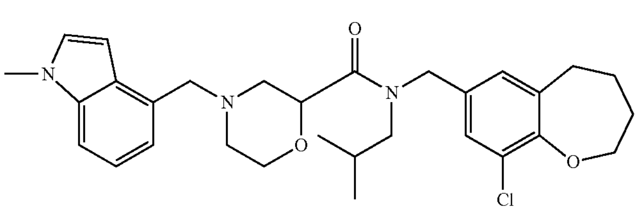 [SMILES: CC(C)CN(Cc1cc(Cl)c2c(c1)CCCCO2)C(=O)C1CN(Cc2cccc3c2ccn3C)CCO1] | (±)-(3R)-4-(N-methyl-indol-4-ylmethyl)-N-(9-chloro-2,3,4,5-tetrahydro-1-benzoxepin-7-ylmethyl)-N-isobutylmorphoine-2-carboxamide | 524.3 | 2.50 | 9.18 |

-continued

| Structure | Compound Name | Mass Ion (M + 1) | Ki for PKR2 (nM) | Ki for PKR1 (nM) |
| --- | --- | --- | --- | --- |
| 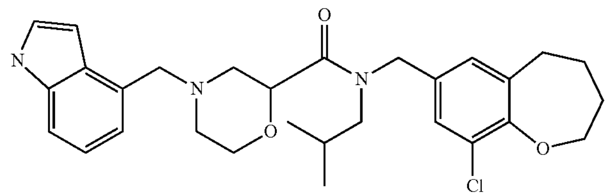 [SMILES: CC(C)CN(Cc1cc(Cl)c2c(c1)CCCCO2)C(=O)C1CN(Cc2cccc3[nH]ccc23)CCO1] | (±)-(3R)-4-(Indol-4-ylmethyl)-N-(9-chloro-2,3,4,5-tetrahydro-1-benzoxepin-7-ylmethyl)-N-isobutylmorpholine-2-carboxamide | 510.3 | 4.26 | 6.62 |
| 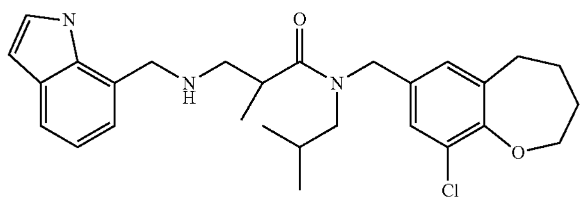 [SMILES: CC(C)CN(Cc1cc(Cl)c2c(c1)CCCCO2)C(=O)C(C)CNCc1cccc2cc[nH]c12] | (±)-2-Methyl-3-(Indol-7-ylmethylamino)-N-(9-chloro-2,3,4,5-tetrahydro-1-benzoxepin-7-ylmethyl)-N-isobutylpropanamide | 482.3 | 5.70 | 61.6 |
| 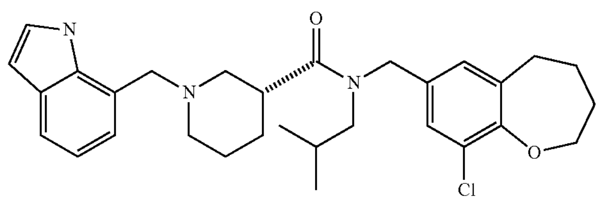 | (−)-(3R)-1-(Indol-7-ylmethyl)-N-(9-chloro-2,3,4,5-tetrahydro-1-benzoxepin-7-ylmethyl)-N-isobutylpiperidine-3-carboxamide | 508.3 | 7.00 | 3.68 |
| 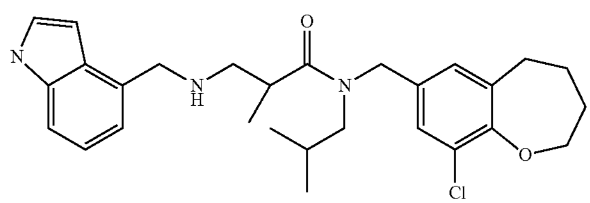 | (±)-2-Methyl-3-(Indol-4-ylmethylamino)-N-(9-chloro-2,3,4,5-tetrahydro-1-benzoxepin-7-ylmethyl)-N-isobutylpropanamide | 482.3 | 21.6 | 53.4 |
| 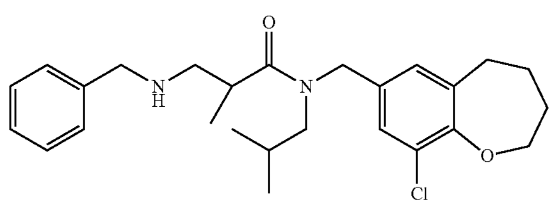 [SMILES: CC(C)CN(Cc1cc(Cl)c2c(c1)CCCCO2)C(=O)C(C)CNCc1ccccc1] | (±)-2-Methyl-3-(benzylmethylamino)-N-(9-chloro-2,3,4,5-tetrahydro-1-benzoxepin-7-ylmethyl)-N-isobutylpropanamide | 443.3 | 73.4 | 21.8 |
| 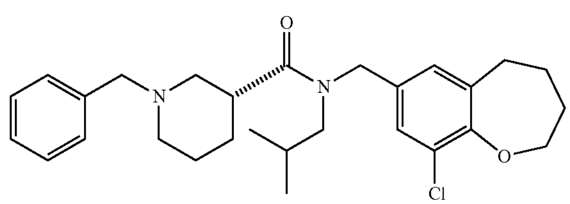 | (−)-(3R)-1-Benzyl-N-(9-chloro-2,3,4,5-tetrahydro-1-benzoxepin-7-ylmethyl)-N-isobutylpiperidine-3-carboxamide | 469.3 | 38.6 | 81.0 |
| 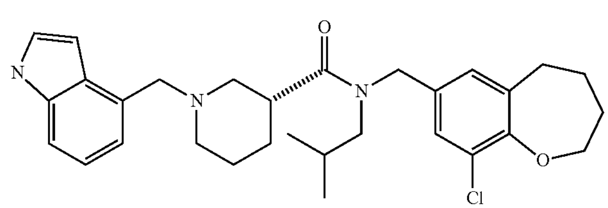 | (−)-(3R)-1-(Indol-4-ylmethyl)-N-(9-chloro-2,3,4,5-tetrahydro-1-benzoxepin-7-ylmethyl)-N-isobutylpiperidine-3-carboxamide | 508.2 | 49.6 | 147 |

-continued

| Structure | Compound Name | Mass Ion (M + 1) | Ki for PKR2 (nM) | Ki for PKR1 (nM) |
|---|---|---|---|---|
| 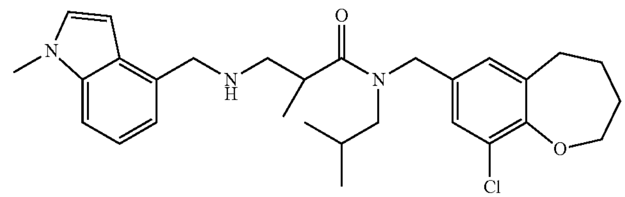 [SMILES: CC(C)CN(Cc1cc(Cl)c2c(c1)CCCCO2)C(=O)C(C)CNCc1cccc2c1ccn2C] | (±)-2-Methyl-3-(N-methyl-indol-4-ylmethylamino)-N-(9-chloro-2,3,4,5-tetrahydro-1-benzoxepin-7-ylmethyl)-N-isobutylpropanamide | 496.2 | 7.60 | 7.32 4.5 |
| 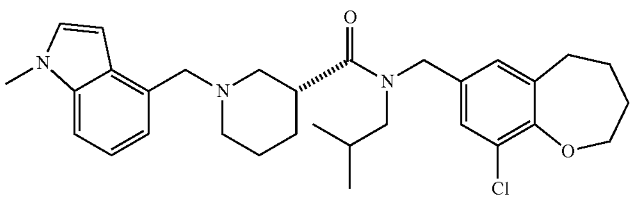 | (−)-(3R)-1-(N-methyl-indol-4-ylmethyl)-N-(9-chloro-2,3,4,5-tetrahydro-1-benzoxepin-7-ylmethyl)-N-isobutylpiperidine-3-carboxamide | 522.2 | 303 | 4.72 |
| 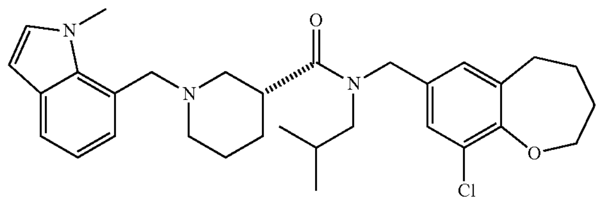 | (−)-(3R)-1-(N-methyl-indol-7-ylmethyl)-N-(9-chloro-2,3,4,5-tetrahydro-1-benzoxepin-7-ylmethyl)-N-isobutylpiperidine-3-carboxamide | 522.2 | 3.00 | 9.42 |
| 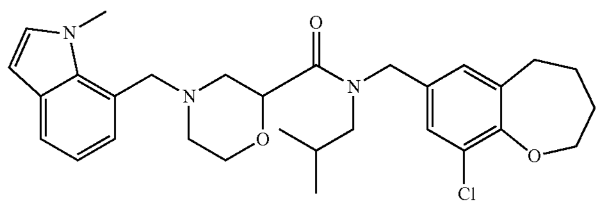 [SMILES: CC(C)CN(Cc1cc(Cl)c2c(c1)CCCCO2)C(=O)C1CN(Cc2cccc3ccn(C)c23)CCO1] | (±)-(3R)-4-(N-methyl-indol-7-ylmethyl)-N-(9-chloro-2,3,4,5-tetrahydro-1-benzoxepin-7-ylmethyl)-N-isobutylmorphoine-2-carboxamide | 524.2 | 6.16 | 9.94 |
| 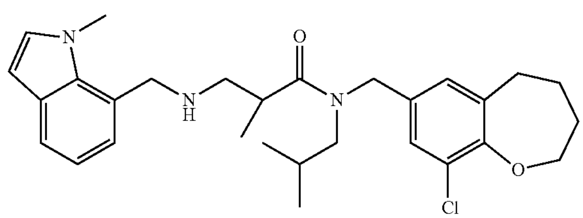 [SMILES: CC(C)CN(Cc1cc(Cl)c2c(c1)CCCCO2)C(=O)C(C)CNCc1cccc2ccn(C)c12] | (±)-2-Methyl-3-(N-methyl-indol-7-ylmethylamino)-N-(9-chloro-2,3,4,5-tetrahydro-1-benzoxepin-7-ylmethyl)-N-isobutylpropanamide | 496.2 | 6.20 | 4.74 8.64 |
| 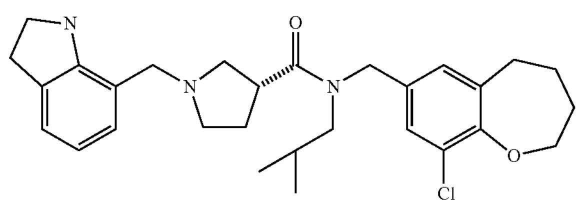 | (−)-(3R)-1-(Indolin-7-ylmethyl)-N-(9-chloro-2,3,4,5-tetrahydro-1-benzoxepin-7-ylmethyl)-N-isobutylpyrrolidine-3-carboxamide | 496.1 | 16.9 | 11.7 |
| 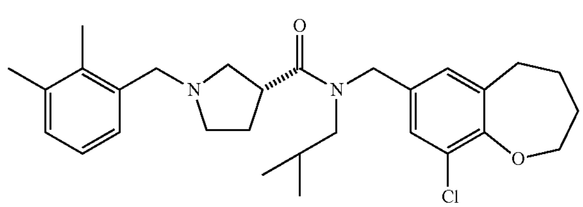 | (−)-(3R)-1-(2,3-Dimethylbenzyl)-N-(9-chloro-2,3,4,5-tetrahydro-1-benzoxepin-7-ylmethyl)-N-isobutylpyrrolidine-3-carboxamide | 483.1 | 8.90 | 25.2 |

-continued

| Structure | Compound Name | Mass Ion (M + 1) | Ki for PKR2 (nM) | Ki for PKR1 (nM) |
|---|---|---|---|---|
| 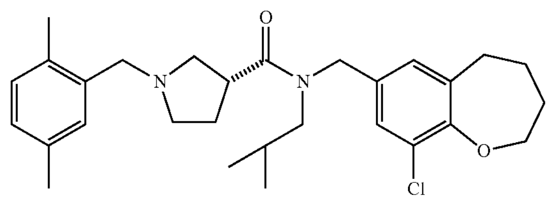 | (−)-(3R)-1-(2,5-Dimethylbenzyl)-N-(9-chloro-2,3,4,5-tetrahydro-1-benzoxepin-7-ylmethyl)-N-isobutylpyrrolidine-3-carboxamide | 483.1 | 8.60 | 33.2 |
| 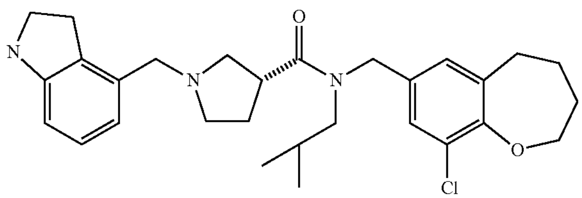 | (−)-(3R)-1-(Indolin-4-ylmethyl)-N-(9-chloro-2,3,4,5-tetrahydro-1-benzoxepin-7-ylmethyl)-N-isobutylpyrrolidine-3-carboxamide | 496.1 | 1.86 | 1.56 0.56 |
| 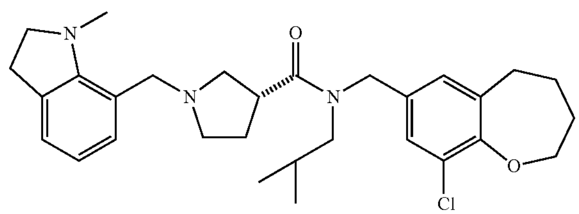 | (−)-(3R)-1-(N-methyl-indolin-7-ylmethyl)-N-(9-chloro-2,3,4,5-tetrahydro-1-benzoxepin-7-ylmethyl)-N-isobutylpyrrolidine-3-carboxamide | 510.1 | 11.3 | 31.4 |
| 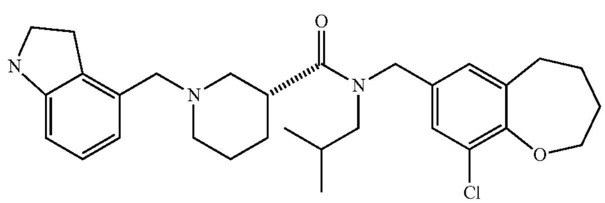 | (−)-(3R)-1-(Indolin-4-ylmethyl)-N-(9-chloro-2,3,4,5-tetrahydro-1-benzoxepin-7-ylmethyl)-N-isobutylpiperidine-3-carboxamide | 510.1 | 5.34 | 22.0 |
| 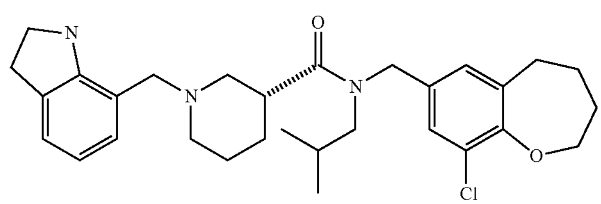 | (−)-(3R)-1-(Indolin-7-ylmethyl)-N-(9-chloro-2,3,4,5-tetrahydro-1-benzoxepin-7-ylmethyl)-N-isobutylpiperidine-3-carboxamide | 510.1 | 3.94 | 4.60 |
| 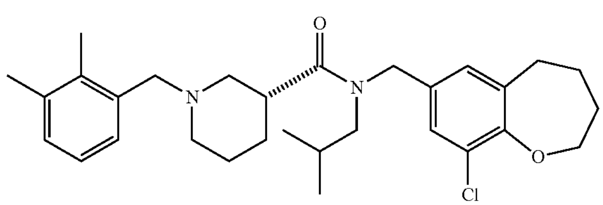 | (−)-(3R)-1-(2,3-Dimethylbenzyl-N-(9-chloro-2,3,4,5-tetrahydro-1-benzoxepin-7-ylmethyl)-N-isobutylpiperidine-3-carboxamide | 497.2 | 20.0 | 65.4 |
| 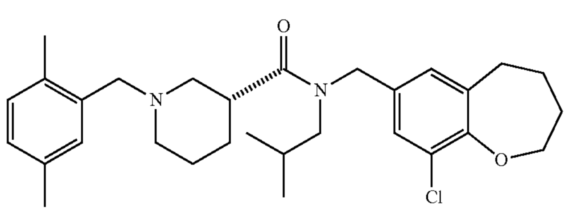 | (−)-(3R)-1-(2,5-Dimethylbenzyl-N-(9-chloro-2,3,4,5-tetrahydro-1-benzoxepin-7-ylmethyl)-N-isobutylpiperidine-3-carboxamide | 497.2 | 7.22 | 18.7 |

-continued

| Structure | Compound Name | Mass Ion (M + 1) | Ki for PKR2 (nM) | Ki for PKR1 (nM) |
|---|---|---|---|---|
| 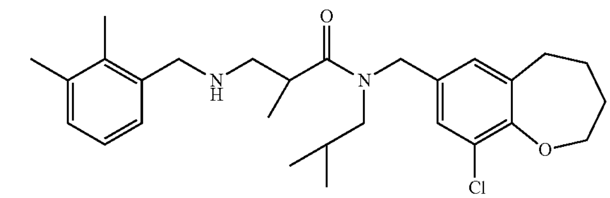 [SMILES: Cc1cccc(CNCC(C)C(=O)N(Cc2cc(Cl)c3c(c2)CCCCO3)CC(C)C)c1C] | (±)-2-Methyl-3-(2,3-dimethylbenzylmethylamino)-N-(9-chloro-2,3,4,5-tetrahydro-1-benzoxepin-7-ylmethyl)-N-isobutylpropanamide | 471.2 | 7.24 | 4.7<br>49.8<br>51.6 |
| 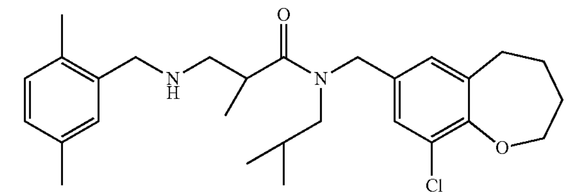 [SMILES: Cc1ccc(C)c(CNCC(C)C(=O)N(Cc2cc(Cl)c3c(c2)CCCCO3)CC(C)C)c1] | (±)-2-Methyl-3-(2,5-dimethylbenzylmethylamino)-N-(9-chloro-2,3,4,5-tetrahydro-1-benzoxepin-7-ylmethyl)-N-isobutylpropanamide | 471.2 | | 35.2 |
| | (−)-(3R)-1-(N-methyl-indolin-4-ylmethyl)-N-(9-chloro-2,3,4,5-tetrahydro-1-benzoxepin-7-ylmethyl)-N-isobutylpiperidine-3-carboxamide | 524.4 | | 36.2 |
| | (−)-(3R)-1-(N-methyl-indolin-4-ylmethyl)-N-(9-chloro-2,3,4,5-tetrahydro-1-benzoxepin-7-ylmethyl)-N-isobutylpiperidine-3-carboxamide | 524.4 | | 22.4 |
| 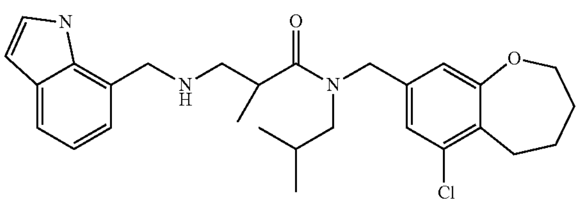 [SMILES: CC(C)CN(Cc1cc(Cl)c2c(c1)OCCCC2)C(=O)C(C)CNCc1cccc2cc[nH]c12] | (±)-2-Methyl-3-(Indol-7-ylmethylamino)-N-(6-chloro-2,3,4,5-tetrahydro-1-benzoxepin-8-ylmethyl)-N-isobutylpropanamide | 482.3 | 183 | 660 |
| 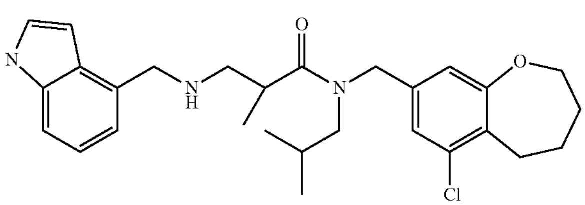 | (±)-2-Methyl-3-(Indol-4-ylmethylamino)-N-(6-chloro-2,3,4,5-tetrahydro-1-benzoxepin-8-ylmethyl)-N-isobutylpropanamide | 482.4 | 308 | |
| 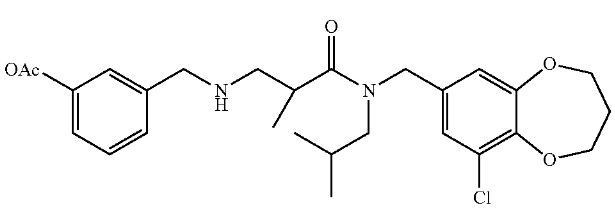 [SMILES: CC(=O)Oc1cccc(CNCC(C)C(=O)N(Cc2cc(Cl)c3c(c2)OCCCO3)CC(C)C)c1] | (±)-2-Methyl-3-((3-acetoxy)benzylamino)-N-(9-chloro-3,4-dihydro-2H-1,5-benzodioxepin-7-ylmethyl)-N-isobutylpropanamide | 503.2 | 0.89 | 3.84 |

-continued

| Structure | Compound Name | Mass Ion (M + 1) | Ki for PKR2 (nM) | Ki for PKR1 (nM) |
|---|---|---|---|---|
| 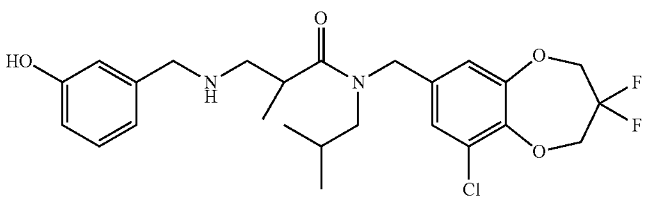 [SMILES: CC(C)CN(Cc1cc(Cl)c2c(c1)OCC(F)(F)CO2)C(=O)C(C)CNCc1cccc(O)c1] | (±)-2-Methyl-3-((3-hydroxy)benzylamino)-N-(9-chloro-3,3-difluoro-3,4-dihydro-2H-1,5-benzodioxepin-7-ylmethyl)-N-isobutylpropanamide | 497.1 | 15.0 | |
| 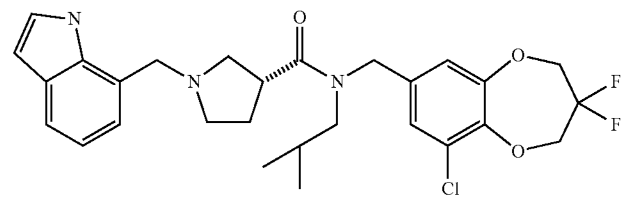 | (−)-(3R)-1-(Indol-7-ylmethyl)-N-(9-chloro-3,3-difluoro-3,4-dihydro-2H-1,5-benzodioxepin-7-ylmethyl)-N-isobutylpyrrolidine-3-carboxamide | 532.3 | 8.0<br>4.4 | 5.5 |
| 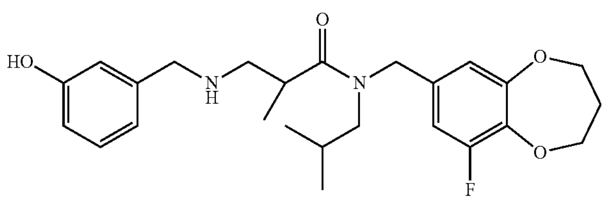 [SMILES: CC(C)CN(Cc1cc(F)c2c(c1)OCCCO2)C(=O)C(C)CNCc1cccc(O)c1] | (±)-2-Methyl-3-((3-hydroxy)benzylamino)-N-(9-fluoro-3,3-difluoro-3,4-dihydro-2H-1,5-benzodioxepin-7-ylmethyl)-N-isobutylpropanamide | 445.3 | 50 | 137 |
| 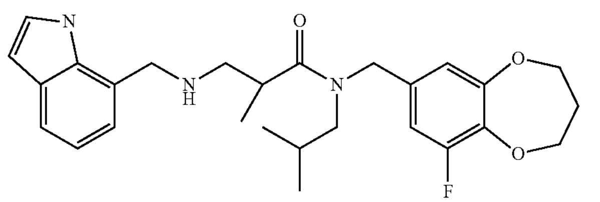 [SMILES: CC(C)CN(Cc1cc(F)c2c(c1)OCCCO2)C(=O)C(C)CNCc1cccc2cc[nH]c12] | (±)-2-Methyl-3-(indol-7-ylmethylamino)-N-(9-fluoro-3,4-dihydro-2H-1,5-benzodioxepin-7-ylmethyl)-N-isobutylpropanamide | 468.3 | 206 | |
| 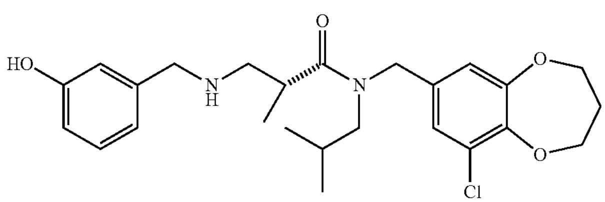 [SMILES: CC(C)CN(Cc1cc(Cl)c2c(c1)OCCCO2)C(=O)[C@H](C)CNCc1cccc(O)c1] | (−)-(2R)-2-Methyl-3-((3-hydroxy)benzylamino)-N-(9-chloro-3,3-difluoro-3,4-dihydro-2H-1,5-benzodioxepin-7-ylmethyl)-N-isobutylpropanamide | 461.3 | 0.28<br>0.93 | 1.15 |
| 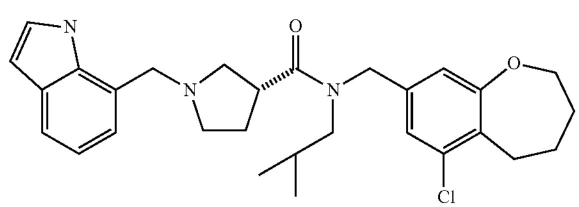 | (−)-(3R)-1-(Indol-7-ylmethyl)-N-(6-chloro-2,3,4,5-tetrahydro-1-benzoxepin-8-ylmethyl)-N-isobutylpyrrolidine-3-carboxamide | 494.2 | 82.0 | |
| 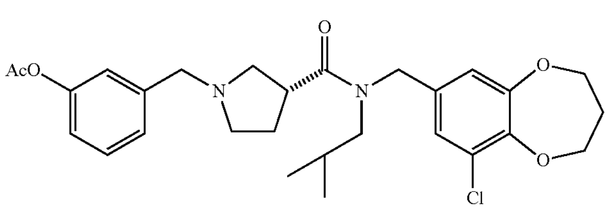 | (−)-(3R)-1-(2-Acetoxybenzyl)-N-(9-chloro-3,4-dihydro-2H-1,5-benzodioxepin-7-ylmethyl)-N-isobutylpyrrolidine-3-carboxamide | 515.3 | | 10.8 |

-continued

| Structure | Compound Name | Mass Ion (M + 1) | Ki for PKR2 (nM) | Ki for PKR1 (nM) |
|---|---|---|---|---|
| 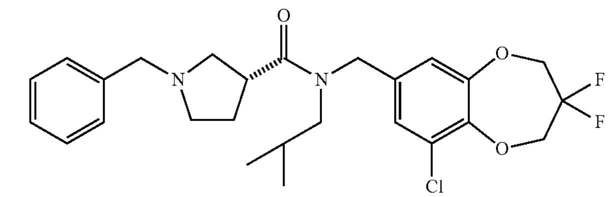 | (−)-(3R)-1-Benzyl-N-(9-chloro-3,3-difluoro-3,4-dihydro-2H-1,5-benzodioxepin-7-ylmethyl)-N-isobutylpyrrolidine-3-carboxamide | 493.2 | | 224 |
| 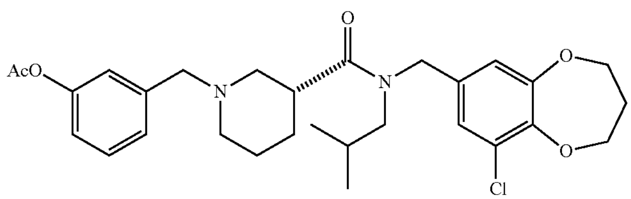 | (−)-(3R)-1-(3-acetoxybenzyl)-N-(9-chloro-3,4-dihydro-2H-1,5-benzodioxepin-7-ylmethyl)-N-isobutylpiperidine-3-carboxamide | 529.2 | | 107 |
| 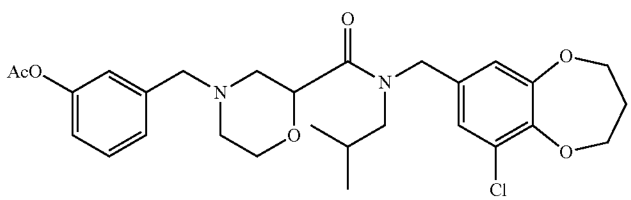 [SMILES: CC(=O)Oc1cccc(CN2CCOC(C(=O)N(Cc3cc(Cl)c4c(c3)OCCCO4)CC(C)C)C2)c1] | (±)-(3R)-1-(3-acetoxybenzyl)-N-(9-chloro-3,4-dihydro-2H-1,5-benzodioxepin-7-ylmethyl)-N-isobutylmorpholine-3-carboxamide | 531.2 | | 8.5 |
| | (−)-(3R)-1-(Indol-7-ylmethyl)-N-(3,4-dihydro-2H-1,5-dioxepino[2,3-b]pyridin-8-ylmethyl)-N-isobutylpiperidine-3-carboxamide | 477.2 | | 104 |
| 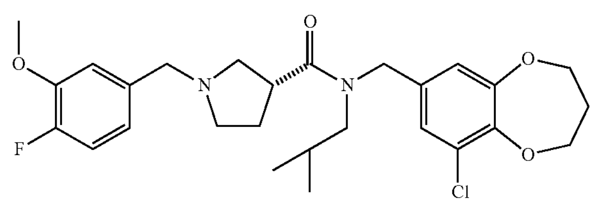 | (−)-(3R)-1-(4-Fluoro-3-methoxybenzyl)-N-(9-chloro-3,4-dihydro-2H-1,5-benzodioxepin-7-ylmethyl)-N-isobutylpyrrolidine-3-carboxamide | 505.2 | | 9.66 |
| 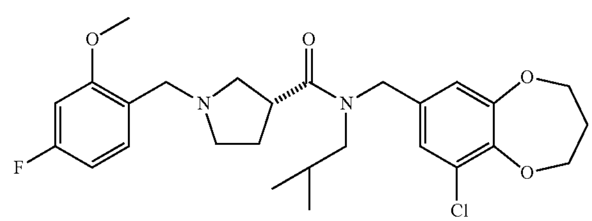 [SMILES: COc1cc(F)ccc1CN1CC[C@@H](C(=O)N(Cc2cc(Cl)c3c(c2)OCCCO3)CC(C)C)C1] | (−)-(3R)-1-(4-Fluoro-2-methoxybenzyl)-N-(9-chloro-3,4-dihydro-2H-1,5-benzodioxepin-7-ylmethyl)-N-isobutylpyrrolidine-3-carboxamide | 505.2 | | 7.72 |
| 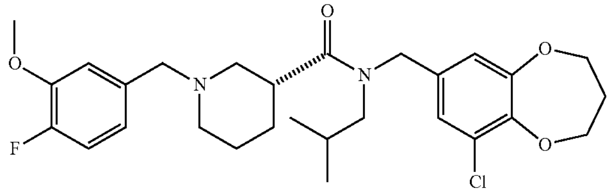 | (−)-(3R)-1-(4-Fluoro-3-methoxybenzyl)-N-(9-chloro-3,4-dihydro-2H-1,5-benzodioxepin-7-ylmethyl)-N-isobutylpiperidine-3-carboxamide | 519.2 | | 8.68 |

-continued

| Structure | Compound Name | Mass Ion (M + 1) | Ki for PKR2 (nM) | Ki for PKR1 (nM) |
|---|---|---|---|---|
| 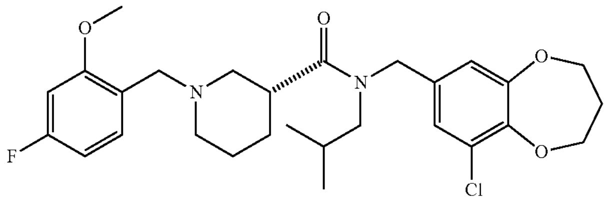 | (−)-(3R)-1-(4-Fluoro-2-methoxybenzyl)-N-(9-chloro-3,4-dihydro-2H-1,5-benzodioxepin-7-ylmethyl)-N-isobutylpiperidine-3-carboxamide | 519.2 | | 65.2 |
| 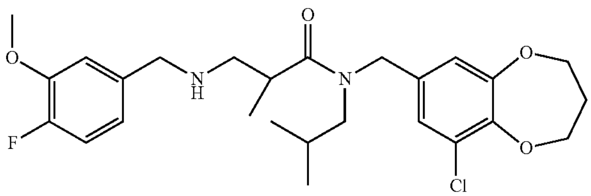 [SMILES: COc1cc(CNCC(C)C(=O)N(Cc2cc(Cl)c3c(c2)OCCCO3)CC(C)C)ccc1F] | (±)-2-Methyl-3-((3-methoxy-4-fluoro)benzylamino)-N-(9-chloro-3,4-dihydro-2H-1,5-benzodioxepin-7-ylmethyl)-N-isobutylpropanamide | 493.2 | | 11.6 |
| 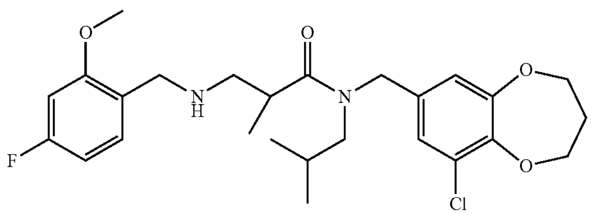 [SMILES: COc1cc(F)ccc1CNCC(C)C(=O)N(Cc1cc(Cl)c2c(c1)OCCCO2)CC(C)C] | (±)-2-Methyl-3-((2-methoxy-4-fluoro)benzylamino)-N-(9-chloro-3,4-dihydro-2H-1,5-benzodioxepin-7-ylmethyl)-N-isobutylpropanamide | 493.2 | | 50.0 |
| 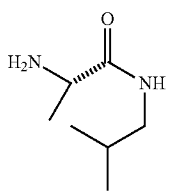 | (−)-(2R)-2-Amino-N-isobutylpropanamide | 145.1 | >10,000 | |
| 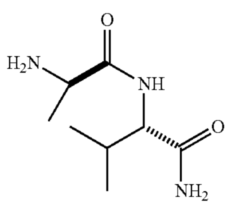 | N-[(2S)-2-Aminopropanoyl]-(2R)-valylamide | 188.2 | >10,000 | |
| 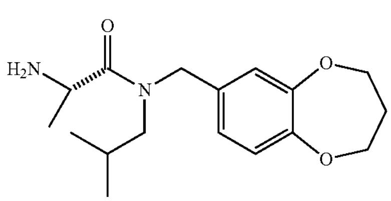 | (−)-(2R)-2-Amino-N-(3,4-dihydro-2H-1,5-benzodioxepin-7-ylmethyl)-N-isobutylpropanamide | 307.1 | >10,000 | |
| 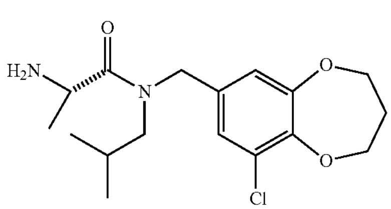 | (−)-(2R)-2-Amino-N-(9-chloro-3,4-dihydro-2H-1,5-benzodioxepin-7-ylmethyl)-N-isobutylpropanamide | 341.1 | >10,000 | |

-continued

| Structure | Compound Name | Mass Ion (M + 1) | Ki for PKR2 (nM) | Ki for PKR1 (nM) |
|---|---|---|---|---|
| 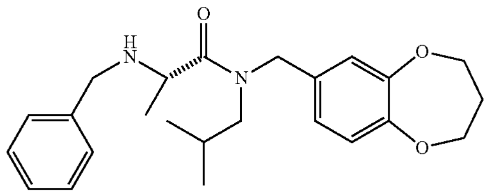 [SMILES: CC(C)CN(Cc1ccc2c(c1)OCCCO2)C(=O)[C@H](C)NCc1ccccc1] | (−)-(2R)-2-Benzylamino-N-(3,4-dihydro-2H-1,5-benzodioxepin-7-ylmethyl)-N-isobutylpropanamide | 397.3 | >10,000 | |
| 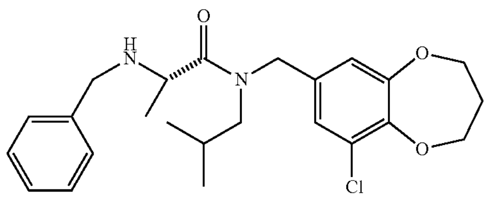 [SMILES: CC(C)CN(Cc1cc(Cl)c2c(c1)OCCCO2)C(=O)[C@H](C)NCc1ccccc1] | (−)-(2R)-2-Benzylamino-N-(9-chloro-3,4-dihydro-2H-1,5-benzodioxepin-7-ylmethyl)-N-isobutylpropanamide | 431.3 | >10,000 | |
| 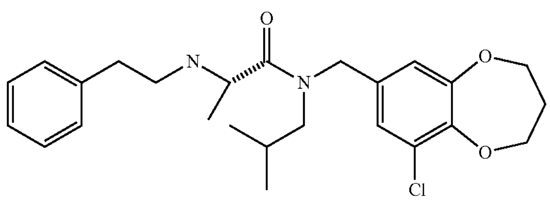 [SMILES: CC(C)CN(Cc1cc(Cl)c2c(c1)OCCCO2)C(=O)[C@H](C)NCCc1ccccc1] | (−)-(2R)-N-(9-Chloro-3,4-dihydro-2H-1,5-benzodioxepin-7-ylmethyl)-N-isobutyl-2-(phenethylamino)propanamide | 445.2 | >10,000 | |
| 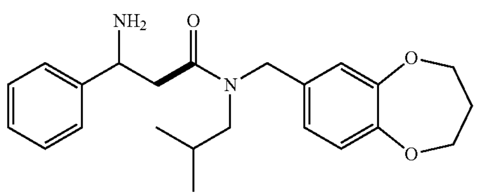 | (−)-(2S)-N-(3,4-dihydro-2H-1,5-benzodioxepin-7-ylmethyl)-N-isobutyl-3-amino-3-phenyl propanamide | 382.3 | >10,000 | |
| 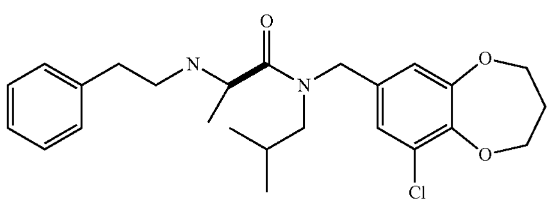 | (−)-(2S)-N-(9-Chloro-3,4-dihydro-2H-1,5-benzodioxepin-7-ylmethyl)-N-isobutyl-2-(phenethylamino)propanamide | 445.2 | >10,000 | |
| 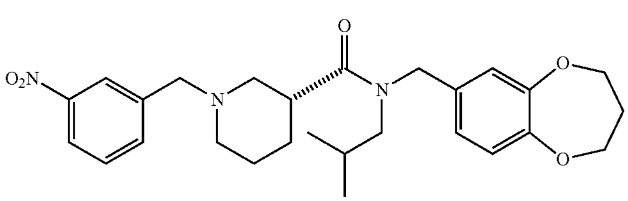 | (−)-(3R)-1-(3-Nitrobenzyl)-N-(3,4-dihydro-2H-1,5-benzodioxepin-7-ylmethyl)-N-isobutylpiperidine-3-carboxamide | 482.4 | >10,000 | |
| 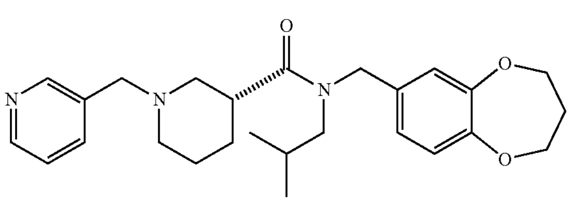 | (−)-(3R)-N-(3,4-dihydro-2H-1,5-benzodioxepin-7-ylmethyl)-N-isobutyl-1-(pyridin-3-ylmethyl)piperidine-3-carboxamide | 438.5 | >10,000 | |

-continued

| Structure | Compound Name | Mass Ion (M + 1) | Ki for PKR2 (nM) | Ki for PKR1 (nM) |
|---|---|---|---|---|
| 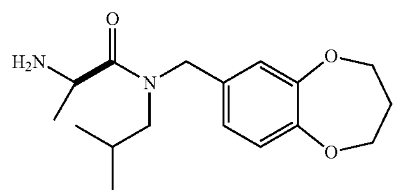 | (+)-(2S)-2-Amino-N-(3,4-dihydro-2H-1,5-benzodioxepin-7-ylmethyl)-N-isobutylpropanamide | 307.1 | >10,000 | |
| 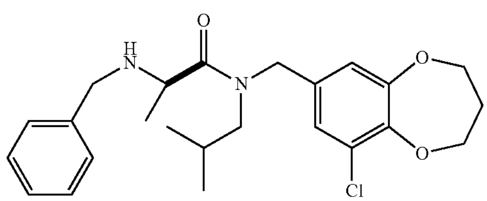 [SMILES: CC(C)CN(Cc1cc(Cl)c2c(c1)OCCCO2)C(=O)[C@@H](C)NCc1ccccc1] | (+)-(2S)-2-Benzylamino-N-(3,4-dihydro-2H-1,5-benzodioxepin-7-ylmethyl)-N-isobutylpropanamide | 397.3 | >10,000 | |
| 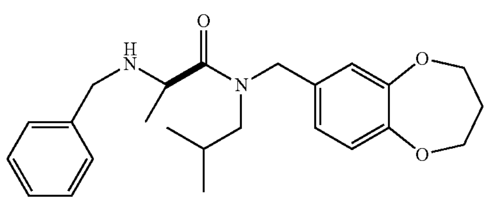 [SMILES: CC(C)CN(Cc1ccc2c(c1)OCCCO2)C(=O)[C@@H](C)NCc1ccccc1] | (+)-(2S)-2-Benzylamino-N-(9-chloro-3,4-dihydro-2H-1,5-benzodioxepin-7-ylmethyl)-N-isobutylpropanamide | 431.3 | >10,000 | |
| 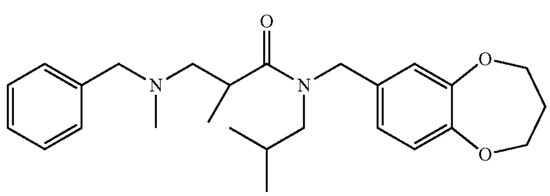 [SMILES: CC(C)CN(Cc1ccc2c(c1)OCCCO2)C(=O)C(C)CN(C)Cc1ccccc1] | (±)-2-Methyl-3-(benzyl(methyl)amino)-N-(9-chloro-3,4-dihydro-2H-1,5-benzodioxepin-7-ylmethyl)-N-isobutylpropanamide | 425.2 | >10,000 | |
| 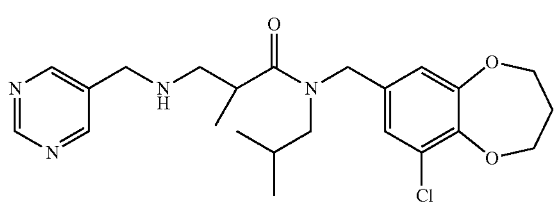 [SMILES: CC(C)CN(Cc1cc(Cl)c2c(c1)OCCCO2)C(=O)C(C)CNCc1cncnc1] | (±)-2-Methyl-3-(pyrimidine-3-ylmethylamino)-N-(9-chloro-3,4-dihydro-2H-1,5-benzodioxepin-7-ylmethyl)-N-isobutylpropanamide | 447.4 | >10,000 | >10,000 |
| 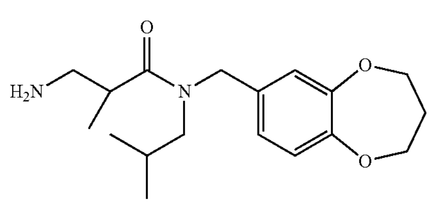 [SMILES: CC(C)CN(Cc1ccc2c(c1)OCCCO2)C(=O)C(C)CN] | (±)-2-Methyl-3-amino-N-(3,4-dihydro-2H-1,5-benzodioxepin-7-ylmethyl)-N-isobutylpropanamide | 321.2 | >10,000 | |
| 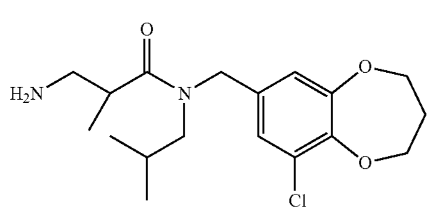 [SMILES: CC(C)CN(Cc1cc(Cl)c2c(c1)OCCCO2)C(=O)C(C)CN] | (±)-2-Methyl-3-amino-N-(9-chloro-3,4-dihydro-2H-1,5-benzodioxepin-7-ylmethyl)-N-isobutylpropanamide | 355.5 | >10,000 | |

-continued

| Structure | Compound Name | Mass Ion (M + 1) | Ki for PKR2 (nM) | Ki for PKR1 (nM) |
|---|---|---|---|---|
| 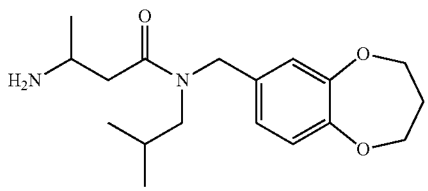 [SMILES: CC(C)CN(Cc1ccc2c(c1)OCCCO2)C(=O)CC(C)N] | (±)-3-Methyl-3-amino-N-(3,4-dihydro-2H-1,5-benzodioxepin-7-ylmethyl)-N-isobutylpropanamide | 321.2 | >10,000 | |
| 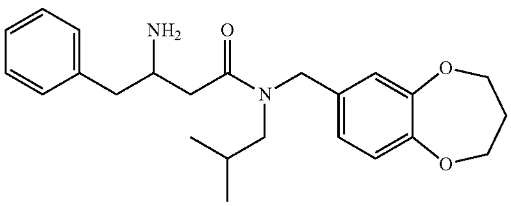 [SMILES: CC(C)CN(Cc1ccc2c(c1)OCCCO2)C(=O)CC(N)Cc1ccccc1] | (±)-N-(3,4-dihydro-2H-1,5-benzodioxepin-7-ylmethyl)-N-isobutyl-3-amino-4-phenylbutanamide | 397.5 | >10,000 | |
| 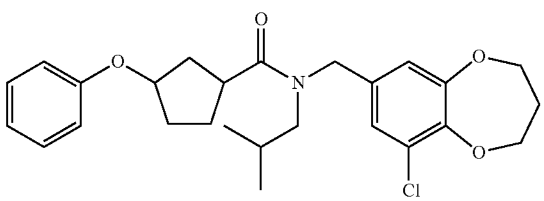 [SMILES: CC(C)CN(Cc1cc(Cl)c2c(c1)OCCCO2)C(=O)C1CCC(Oc2ccccc2)C1] | (±)-N-(9-Chloro-3,4-dihydro-2H-1,5-benzodioxepin-7-ylmethyl)-N-isobutyl-3-phenoxycyclopentanecarboxamide | 458.3 | >10,000 | |
| 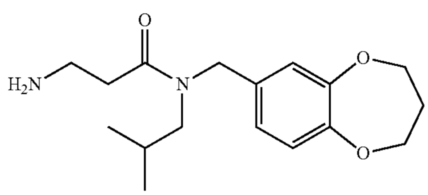 [SMILES: CC(C)CN(Cc1ccc2c(c1)OCCCO2)C(=O)CCN] | 3-Amino-N-(3,4-dihydro-2H-1,5-benzodioxepin-7-ylmethyl)-N-isobutylpropanamide | 307.2 | >10,000 | |
| 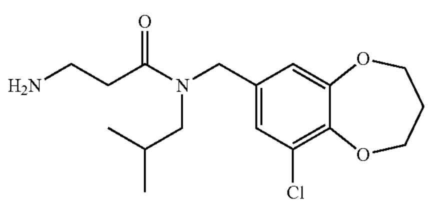 [SMILES: CC(C)CN(Cc1cc(Cl)c2c(c1)OCCCO2)C(=O)CCN] | 3-Amino-N-(9-chloro-3,4-dihydro-2H-1,5-benzodioxepin-7-ylmethyl)-N-isobutylpropanamide | 341.3 | >10,000 | |
| 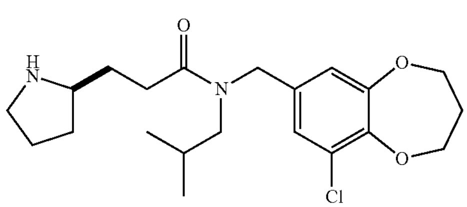 | N-(9-Chloro-3,4-dihydro-2H-1,5-benzodioxepin-7-ylmethyl)-N-isobutyl-3-(pyrrolidin-2-yl)propanamide | 381.2 | >10,000 | |
| 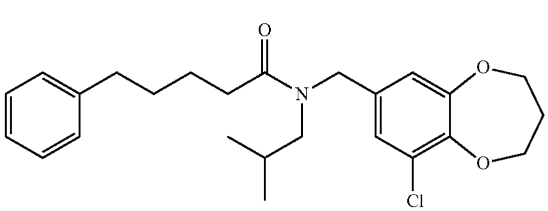 [SMILES: CC(C)CN(Cc1cc(Cl)c2c(c1)OCCCO2)C(=O)CCCCc1ccccc1] | N-(9-Chloro-3,4-dihydro-2H-1,5-benzodioxepin-7-ylmethyl)-N-isobutyl-5-phenylpentanamide | 430.3 | >10,000 | |

| Structure | Compound Name | Mass Ion (M + 1) | Ki for PKR2 (nM) | Ki for PKR1 (nM) |
|---|---|---|---|---|
| 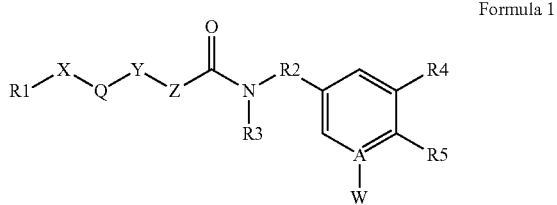 | (±)-2-Methyl-3-(benzylamino)-N-(6-chloro-2,3,4,5-tetrahydro-1-benzoxepin-8-ylmethyl)-N-isobutylpropanamide | 443.3 | >10,000 | |

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A compound having a structure according to Formula 1

Formula 1 wherein
R1 is an optionally substituted aryl, optionally substituted heteroaryl, or an optionally substituted aryl with a fused heterocyclic ring;
X is CH2 and Y is lower alkyl;
Q is NH or NR6, wherein R6 is lower alkyl;
Z is CH2 or CHR7, wherein R7 is lower alkyl; or Q and Z are covalently coupled to each other to form a heterocyclic 4- to 6-membered ring in which Q is N and Z is CH, with the proviso that the heterocyclic ring is not a morpholine ring;
R2 is CH2;
R3 is H, lower alkyl, or alkaryl;
A is N or C;
W is H, or halogen, or W is null where A is N; and
R4 and R5 are independently alkoxy, or are covalently coupled to each other to form an optionally substituted heterocyclic 6- or 7-membered ring with at least one oxygen atom.

2. The compound of claim 1 wherein R1 is optionally substituted phenyl, optionally substituted indolyl, or optionally substituted indolinyl.

3. The compound of claim 1 wherein X and Y are CH2.

4. The compound of claim 1 wherein X and Y are covalently coupled to each other to form a pyrrolidine ring, a piperidine ring, a piperazine ring, a thiomorpholine ring, or a morpholine ring.

5. The compound of any one of claim 3 or claim 4 wherein R3 is optionally branched lower alkyl.

6. The compound of claim 1 wherein R4, R5, W, and the phenyl ring to which R4, R5, and W are covalently coupled form an optionally halogenated benzodioxepin ring.

7. The compound of claim 1 wherein W is Cl or F.

8. A pharmaceutical composition for treatment of type II diabetes, comprising a compound according to claim 1, and a pharmaceutically acceptable carrier.

9. The pharmaceutical composition of claim 8 wherein the compound is present in a dosage unit for oral administration in an amount effective to treat type II diabetes.

10. A method of treating type II diabetes, comprising a step of administering a prokineticin antagonist according to claim 1 at a concentration effective to treat type II diabetes.

11. A method of inhibiting a prokineticin receptor, comprising a step of contacting prokineticin receptor with a compound according to claim 1.

12. The method of claim 11 wherein the step of contacting in performed in vivo.

* * * * *